(12) United States Patent
Gil et al.

(10) Patent No.: US 6,276,798 B1
(45) Date of Patent: Aug. 21, 2001

(54) SPECTRAL BIO-IMAGING OF THE EYE

(75) Inventors: Tamir Gil, Kibbuz Givat Haim Meuchad; Dario Cabib, Timrat; Mike Adel, Zichron Yaakov; Robert A. Buckwald, Ramat Yishai; Eli Horn, Kyriat Motzkin, all of (IL)

(73) Assignee: Applied Spectral Imaging, Ltd., Migdal Haemek (IL)

( * ) Notice: Subject to any disclaimer, the term of this patent is extended or adjusted under 35 U.S.C. 154(b) by 0 days.

(21) Appl. No.: 09/307,569

(22) Filed: May 10, 1999

Related U.S. Application Data

(63) Continuation-in-part of application No. 09/194,196, filed on Nov. 20, 1998.

(30) Foreign Application Priority Data

Sep. 29, 1998 (WO) .................................. PCT/US98/20442

(51) Int. Cl.$^7$ ............................................ A61B 3/14
(52) U.S. Cl. ............................................ 351/206
(58) Field of Search .................................. 351/205, 206, 351/221; 348/262, 263, 264, 393; 356/345, 346

(56) References Cited

U.S. PATENT DOCUMENTS 5,539,517 * 7/1996 Cabib et al. ........................ 356/346
5,784,162 * 7/1998 Cabib et al. ........................ 348/264

* cited by examiner

Primary Examiner—George Manuel

(57) ABSTRACT

A spectral bio-imaging method for enhancing pathologic, physiologic, metabolic and health related spectral signatures of an eye tissue, the method comprising the steps of (a) providing an optical device for eye inspection being optically connected to a spectral imager; (b) illuminating the eye tissue with light via the iris, viewing the eye tissue through the optical device and spectral imager and obtaining a spectrum of light for each pixel of the eye tissue; and (c) attributing each of the pixels a color or intensity according to its spectral signature, thereby providing an image enhancing the spectral signatures of the eye tissue.

56 Claims, 28 Drawing Sheets

(12 of 28 Drawing Sheet(s) Filed in Color)

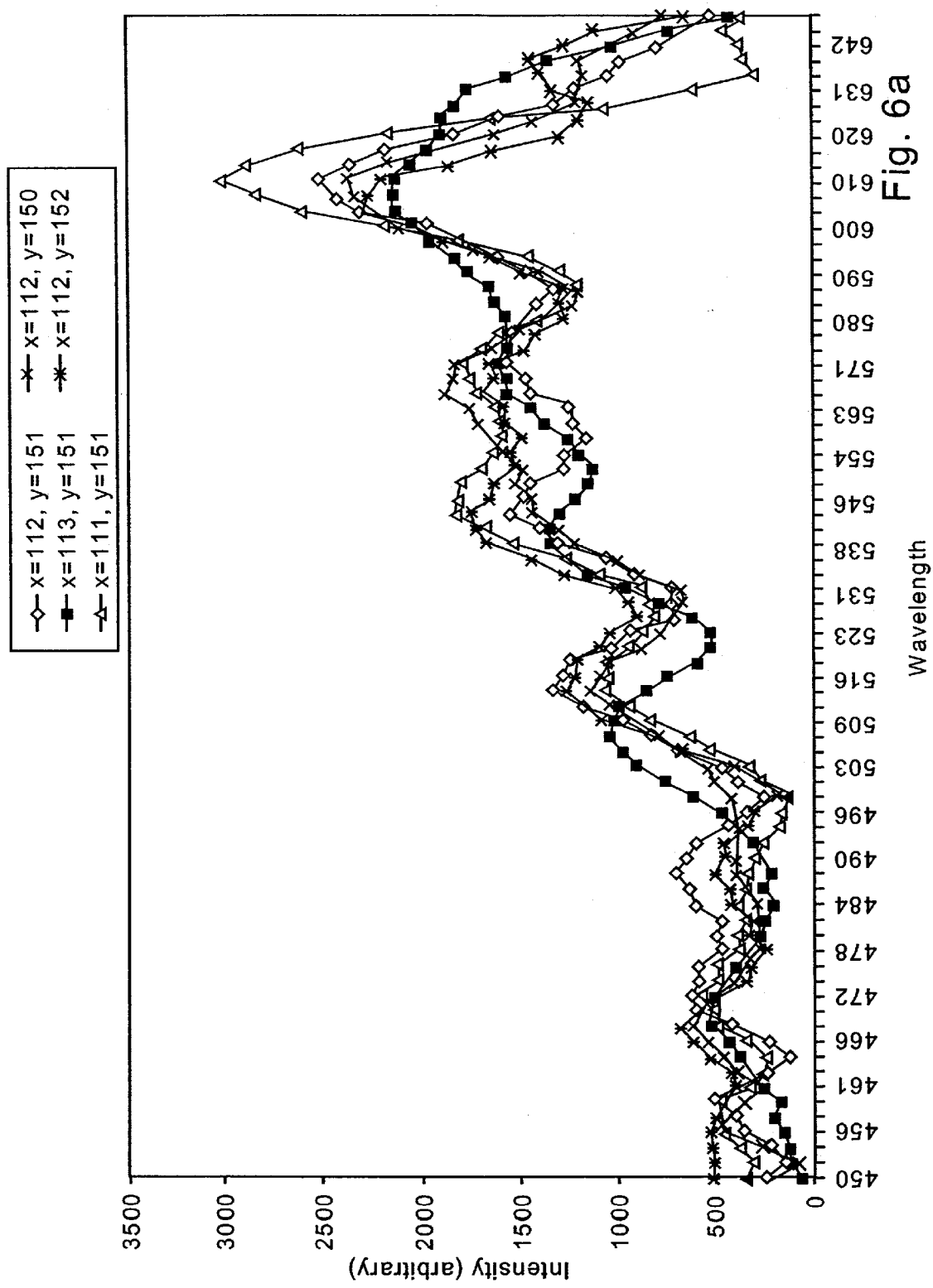

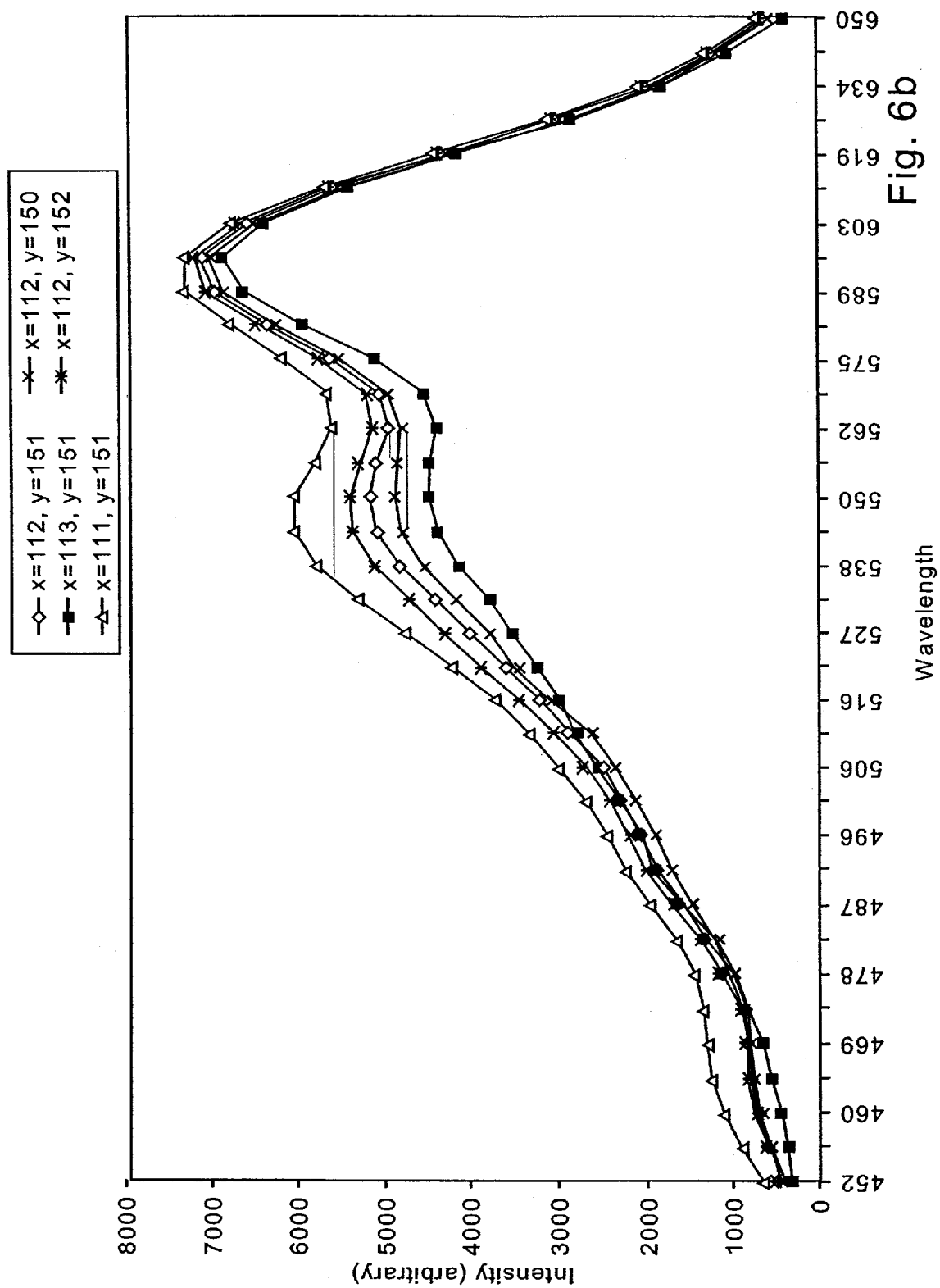

RGB Image

Spectrally enhanced RGB 610 nm 564 nm

Hemoglobin oxygenation

RGB Image 610 nm 564 nm

Hemoglobin concentration

FIG. 19a
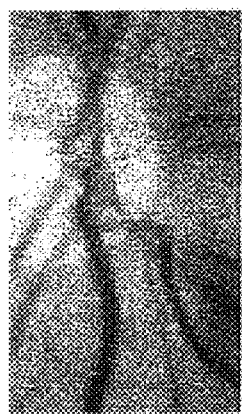
RGB Image
FIG. 19b
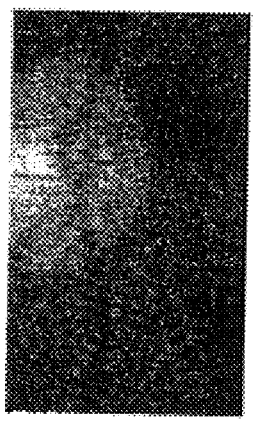
610 nm
FIG. 19c
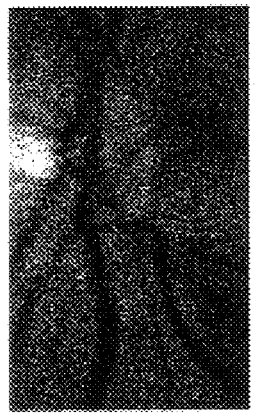
564 nm
FIG. 19d
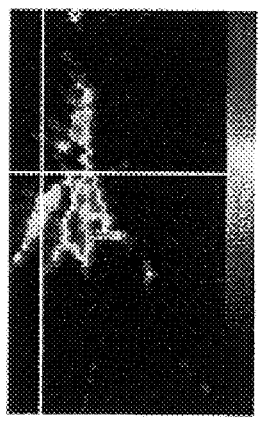
Hemoglobin concentration
FIG. 19e
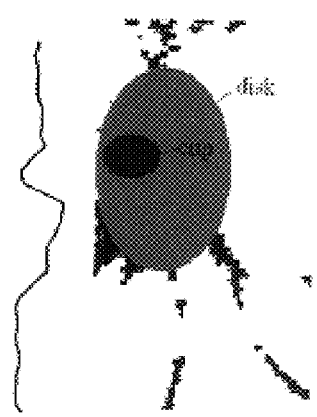
Image key

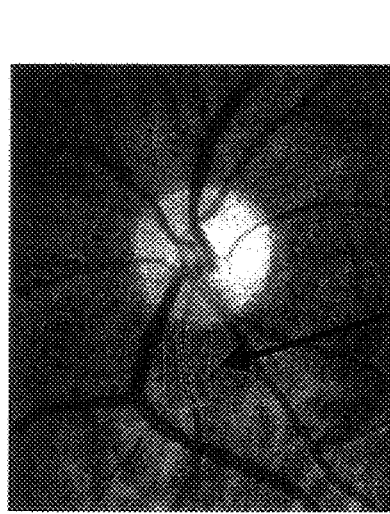 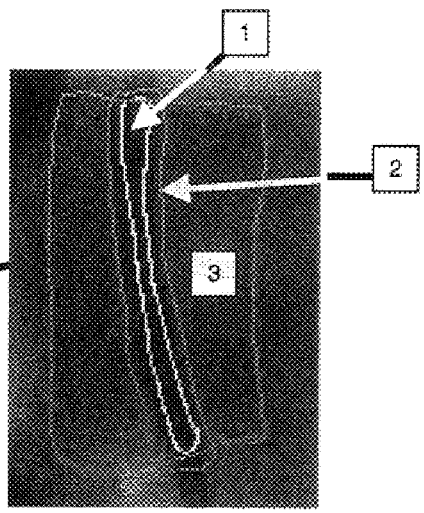
Fig. 30a        Fig. 30b
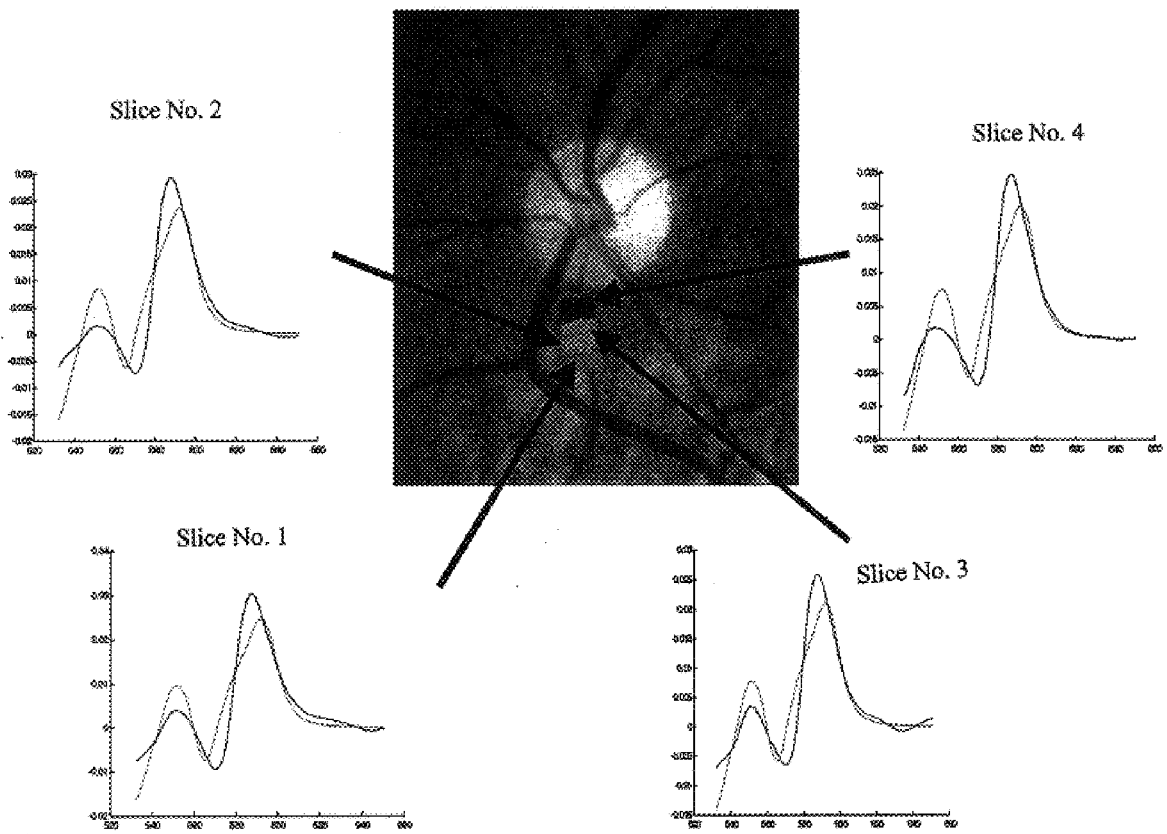
Fig. 31

SPECTRAL BIO-IMAGING OF THE EYE

This is a continuation-in-part of U.S. patent application No. 09/194,196, filed Nov. 20, 1998.

FIELD AND BACKGROUND OF THE INVENTION

The present invention relates to spectral imaging in general and, more particularly, to spectral bio-imaging of the eye which can be used for non-invasive early detection and diagnosis of eye diseases and for detection of spatial organization, distribution and quantification of cellular and tissue natural constituents, structures and organelles, tissue vitality, tissue metabolism, tissue viability, etc., using light reflection, scattering and emission, with high spatial and spectral resolutions.

A spectrometer is an apparatus designed to accept light, to separate (disperse) it into its component wavelengths and measure a spectrum, that is the intensity of the light as a function of its wavelength. An imaging spectrometer (also referred to hereinbelow as a spectral imager) is one which collects incident light from a scene and measures the spectra (in part or in full) of each pixel or picture element thereof.

Spectroscopy is a well known analytical tool which has been used for decades in science and industry to characterize materials and processes based on the spectral signature of chemical constituents. The physical basis of spectroscopy is the interaction of light with matter. Traditionally, spectroscopy is the measurement of the light intensity emitted, transmitted, scattered or reflected from a sample, as a function of wavelength, at high spectral resolution, but without any spatial information.

Spectral imaging, on the other hand, is a combination of high resolution spectroscopy and high resolution imaging (i.e., spatial information). The closest work so far described with respect to the eye concerns either obtaining high spatial resolution information, yet providing only limited spectral information, for example, when high spatial resolution imaging is performed with one or several discrete band-pass filters [see, for example, Patrick J. Saine and Marshall E. Tyler, Ophthalmic Photography, A textbook of retinal photography, angiography, and electronic imaging, Butterworth-Heinemann, Copyright 1997, ISBN 0-7506-9793-8, p. 72], or alternatively, obtaining high spectral resolution (e.g., a full spectrum), yet limited in spatial resolution to a small number of points of the eye or averaged over the whole sample [See for example, Delori F. C., Pflibsen K. P., Spectral reflectance of the human ocular fundus, Applied Optics Vol. 28, pp. 1061–1077, 1989].

Conceptually, a spectral imaging system consists of (i) a measurement system, and (ii) an analysis software. The measurement system includes all of the optics, electronics, illumination source, etc., as well as calibration means best suited for extracting the desired results from the measurement. The analysis software includes all of the software and mathematical algorithms necessary to analyze and display important results in a meaningful way.

Spectral imaging has been used for decades in the area of remote sensing to provide important insights in the study of Earth and other planets by identifying characteristic spectral absorption features. However, the high cost, size and configuration of remote sensing spectral imaging systems (e.g., Landsat, AVIRIS) has limited their use to air and satellite-born applications [See, Maymon and Neeck (1988) Proceedings of SPIE—Recent Advances in Sensors, Radiometry and Data Processing for Remote Sensing, 924, pp. 10–22; Dozier (1988) Proceedings of SPIE—Recent Advances in Sensors, Radiometry and Data Processing for Remote Sensing, 924, pp. 23–30]

There are three basic types of spectral dispersion methods that might be considered for a spectral bio-imaging system: (i) spectral grating and/or prism, (ii) spectral filters and (iii) interferometric spectroscopy.

In a grating/prism (i.e., monochromator) based systems, also known as slit-type imaging spectrometers, such as for example the DILOR system: [see, Valisa et al. (Sep. 1995) presentation at the SPIE Conference European Medical Optics Week, BiOS Europe '95, Barcelona, Spain], only one axis of a CCD (charge coupled device) array detector (the spatial axis) provides real imagery data, while a second (spectral) axis is used for sampling the intensity of the light which is dispersed by the grating as function of wavelength. The system also has a slit in a first focal plane, limiting the field of view at any given time to a line of pixels. Therefore, a full image can only be obtained after scanning the grating or the incoming beam in a direction parallel to the spectral axis of the CCD in a method known in the literature as line scanning. The inability to visualize the two-dimensional image before the whole measurement is completed makes it impossible to choose, prior to making a measurement, a desired region of interest from within the field of view and/or to optimize the system focus, exposure time, etc. Grating based spectral imagers are popular in use for remote sensing applications, because an airplane (or satellite) flying over the surface of the Earth provides the system with a natural line scanning mechanism.

It should be further noted that slit-type imaging spectrometers have a major disadvantage since most of the pixels of one frame are not measured at any given time, even though the fore- optics of the instrument actually collects incident light from all of them simultaneously. The result is that either a relatively large measurement time is required to obtain the necessary information with a given signal-to-noise ratio, or the signal-to-noise ratio (sensitivity) is substantially reduced for a given measurement time. Furthermore, slit-type spectral imagers require line scanning to collect the necessary information for the whole scene, which may introduce inaccuracies to the results thus obtained.

Filter based spectral dispersion methods can be further categorized into discrete filters and tunable filters. In these types of imaging spectrometers the spectral image is built by filtering the radiation for all the pixels of the scene simultaneously at a different wavelength at a time by inserting in succession narrow band filters in the optical path, or by electronically scanning the bands using AOTF or LCTF (see below).

Similarly to the slit type imaging spectrometers equipped with a grating, as described above, while using filter based spectral dispersion methods, most of the radiation is rejected at any given time. In fact, the measurement of the whole image at a specific wavelength is possible because all the photons outside the instantaneous wavelength measured are rejected and do not reach the CCD.

Tunable filters, such as acousto-optic tunable filters (AOTFs) and liquid-crystal tunable filter (LCTFs) have no moving parts and can be tuned to any particular wavelength in the spectral range of the device in which they are implemented. One advantage of using tunable filters as a dispersion method for spectral imaging is their random wavelength access; i.e., the ability to measure the intensity of an image at a number of wavelengths, in any desired sequence without the use of a mechanical filter wheel. However, AOTFs and LCTFs have the disadvantages of (i) limited spectral range (typically, $\lambda_{max}=2\lambda_{min}$) while all other radiation that falls outside of this spectral range must be blocked, (ii) temperature sensitivity, (iii) poor transmission, (iv) polarization sensitivity, and (v) in the case of AOTFs an effect of shifting the image during wavelength scanning.

All these types of filter and tunable filter based systems have not been used successfully and extensively over the years in spectral imaging for any application, because of their limitations in spectral resolution, low sensitivity, and lack of easy-to-use and sophisticated software algorithms for interpretation and display of the data.

No literature has been found by the inventors of the present invention describing high resolution spectroscopy combined with high resolution imaging applied to the eye.

A method and apparatus for spectral analysis of images which have advantages in the above respects were disclosed in U.S. Pat. Nos. 5,539,517 and 5,835,214 to Cabib et al., which are incorporated by reference as if fully set forth herein, with the objective to provide methods and apparatuses for spectral analysis of images which better utilizes all the information available from the collected incident light of the image to substantially decrease the required frame time and/or to substantially increase the signal-to-noise ratio, as compared to the conventional slit- or filter type imaging spectrometers and do not involve line scanning.

According to this invention, there is provided a method of analyzing an optical image of a scene to determine the spectral intensity of each pixel thereof by collecting incident light from the scene; passing the light through an interferometer which outputs modulated light corresponding to a predetermined set of linear combinations of the spectral intensity of the light emitted from each pixel; focusing the light outputted from the interferometer on a detector array, scanning the optical path difference (OPD) generated in the interferometer for all pixels independently and simultaneously and processing the outputs of the detector array (the interferograms of all pixels separately) to determine the spectral intensity of each pixel thereof.

This method may be practiced by utilizing various types of interferometers wherein the OPD is varied to build the interferograms by moving the entire interferometer, an element within the interferometer, or the angle of incidence of the incoming radiation. In all of these cases, when the scanner completes one scan of the interferometer, the interferograms for all pixels of the scene are completed.

Apparatuses in accordance with the above features differ from the conventional slit- and filter type imaging spectrometers by utilizing an interferometer as described above, therefore not limiting the collected energy with an aperture or slit or limiting the incoming wavelength with narrow band interference or tunable filters, thereby substantially increasing the total throughput of the system.

Thus, interferometer based apparatuses better utilize all the information available from the incident light of the scene to be analyzed, thereby substantially decreasing the measuring time and/or substantially increasing the signal-to-noise ratio (i.e., sensitivity).

Consider, for example, the "whisk broom" design described in John B. Wellman (1987) Imaging Spectrometers for Terrestrial and Planetary Remote Sensing, SPIE Proceedings, Vol. 750, p. 140. Let n be the number of detectors in the linear array, m×m the number of pixels in a frame and T the frame time. The total time spent on each pixel in one frame summed over all the detectors of the array is $nT/m^2$. By using the same size array and the same frame rate in a method according to the invention described in U.S. Pat. No. 5,539,517, the total time spent summed over all the detectors on a particular pixel is the same, $nT/m^2$.

However, whereas in the conventional grating method the energy seen by every detector at any given time is of the order of 1/n of the total, because the wavelength resolution is 1/n of the range, in a method according to the invention described in U.S. Pat. No. 5,539,517 the energy is of the order of unity because the modulating function is an oscillating function (e.g., sinusoidal (Michelson) or a similar periodic function, such as the low finesse Airy function with Fabry-Perot) whose average over a large OPD range is 50%. Based on the standard treatment of the Fellgett advantage (or multiplex advantage) described in interferometry textbooks [for example, see, Chamberlain (1979) The principles of interferometric spectroscopy, John Wiley and Sons, pp. 16–18 and p. 263], it is possible to show that devices according to this invention have measurement signal-to-noise ratios which are improved by a factor of $n^{0.5}$ in the cases of noise limitations in which the noise level is independent of signal (system or background noise limited situations) and by the square root of the ratio of the signal at a particular wavelength to the average signal in the spectral range, at wavelengths of a narrow peak in the cases the limitation is due to signal photon noise.

Thus, according to the invention described in U.S. Pat. No. 5,539,517, all the required OPDs are scanned simultaneously for all the pixels of the scene in order to obtain all the information required to reconstruct the spectrum, so that the spectral information is collected simultaneously with the imaging information.

Spectral bio-imaging systems are potentially useful in all applications in which subtle spectral differences exist between chemical constituents whose spatial distribution and organization within an image are of interest. The measurement can be carried out using virtually any optical system attached to the system described in U.S. Pat. No. 5,539,517, for example, an upright or inverted microscope, a fluorescence microscope, a macro lens, an endoscope or a fundus camera. Furthermore, any standard experimental method can be used, including light transmission (bright field and dark field), autofluorescence and fluorescence of administered probes, light transmission, scattering and reflection.

Fluorescence measurements can be made with any standard filter cube (consisting of a barrier filter, excitation filter and a dichroic mirror), or any customized filter cube for special applications, provided that the emission spectra fall within the spectral range of the system sensitivity.

Spectral bio-imaging can also be used in conjunction with any standard spatial filtering method such as dark field and phase contrast, and even with polarized light microscopy. The effects on spectral information when using such methods must, of course, be understood to correctly interpret the measured spectral images.

Reflection of visible light from the ocular fundus has been used for many years for research and for routine eye inspection by ophthalmologists. It is also the basis for recording the eye status of a patient for disease and treatment follow up, both as pictures on a camera film and as digital images in the computer memory.

In contrast, the spectral dependence of the light reflection from different regions of the fundus has been relegated only to research work. The reasons for these facts are (i) images are a very direct means of presenting information to a human being, because they are easily interpreted, compared and remembered by the human brain; (ii) spectral data are much less direct, are not immediately understandable, and to be useful they must usually undergo several layers of mathematical processing before they are related to the bio-physiological properties of the tissue in question; and (iii) there has been so far no affordable instrumentation available to collect and analyze spectral data from the fundus, which is easy to use, fast, and reliable for a research or clinical setting.

As a result, at present, the use of spectral information in many fields, and in particular in ophthalmology, is lagging enormously behind the imaging techniques.

Recently, Applied Spectral Imaging Ltd. of Migdal Haemek, Israel, has developed the SPECTRACUBE technology. The SPECTRACUBE technology is based on an interferometer based spectral imager and as such it combines spectroscopy and imaging to use the advantages of both. It collects spectral data from all the pixels of an image simultaneously so that, after appropriate processing, the important chemical composition of the studied object (related to its bio-physiological properties) can be mapped and visualized.

The SPECTRACUBE technology was employed for spectral (color) karyotyping which simplifies and improves the detection capability of chromosomal aberrations using fluorescence emission [see, Multicolor spectral karyotyping of human chromosomes. E. Schroeck et al., Science, 273, 494–497, 1996; Multicolor spectral karyotyping of mouse chromosomes. Marek Liyanage et al. Nature Genetics p. 312–315, 1996; Spectral Karyotyping. Yuval Garini, et al. Bioimaging 4, p. 65–72, 1996; Hidden chromosome abnormalities in haemotological malignancies detected by multicolor spectral Karyotyping. Tim Veldman, Christine Vignon, Evelin Schrock, Janet D. Rowley & Thomas Ried. Nature Genetics, April, 1997: 406–410.; Spectral Karyotyping: Chromosomes in Color. Turid Knutsen, Tim Veldman, Hesed Padilla-Nash, Evelin Schrock, Morek Liyanage, Thomas Ried. Applied Cytogenetics, 23(2) 1997, pp. 26–32.; and Early Experiences with SKY: A Primer for the Practicing Cytogenetic Technologist. Michele Shuster, Ulrike Bockmuhl, Susanne M. Gollin. Applied Cytogenetics, 23(2) 1997, pp. 33–37].

Diabetic retinopathy is a potentially devastating condition of the human vision system, that, in most cases, can be controlled with timely laser treatment [Ferris (1993) (commentary) JAMA 269:1290–1291]. The American Academy of Ophthalmology has suggested screening schedules to detect when patients develop clinical conditions which should be treated [Diabetic Retinopathy: American Academy of Ophthalmology Preferred Practice Patterns. San Francisco, Ca.: American Academy of Ophthalmology Quality of Care Committee Retinal Pane, American Academy of Ophthalmology, 1989].

However the suggested screening schedule is expensive, and for some individuals even the current expensive screening is not sufficient because patients occasionally develop severe retinopathy between scheduled examinations. In spite of this, it has been shown that this screening is cost effective [Javitt et al. (1989) Ophthalmology 96:255–64]. This work shows that a large amount of money could be saved in health care follow up, if high and low risk patients could be more effectively identified. Therefore, any method that could increase the accuracy and reduce the cost of screening for diabetic retinopathy would be of high clinical value.

Currently, the recommended screening evaluation for diabetic retinopathy includes a detailed retinal evaluation and, in selected cases, color retinal photography [Diabetic Retinopathy: American Academy of Ophthalmology Preferred Practice Patterns. San Francisco, Ca.: American Academy of Ophthalmology Quality of Care Committee Retinal Pane, American Academy of Ophthalmology, 1989]. Fluorescein angiography of the retina is routinely performed today, but it is invasive, unpleasant, and causes occasional deaths. Furthermore, the additional information obtained by fluorescein angiography does not help categorize patients into those who may benefit from immediate laser treatment and those who will not [Ferris (1993) (commentary) JAMA 269:1290–1].

The oxygen supply of the retina is provided by both the choroidal and retinal circulation. The choroid serves as the oxygen source for the photoreceptors in the avascular outer retina, whereas the retinal circulation plays a crucial role in maintaining the oxygen supply to the neural elements and nerve fibers in the inner retina. Because of the high oxygen needs of the retina, any alteration in circulation such as seen in diabetic retinopathy, hypertension, sickle cell disease, and vascular occlusive diseases results in functional impairment and extensive retinal tissue.

Noninvasive measurements of the oxygen saturation of blood in retinal vessels was first proposed by Hickham et al. [Hickham et al. (1963) Circulation 27:375] using a two-wavelength photographic technique (560 and 640 nm) for retinal vessels crossing the optic disk (the region where the optic nerve connects to the retina). A more advanced approach based on the three wavelength method of Pittman and Duling is presented in Delori (1988) Applied Optics 27:1113–1125.

The present invention is the first step towards showing the usefulness of spectral imaging in general and the SPECTRACUBE technology in particular, as a new tool for the analysis of the physiological state of various structures of the human ocular fundus and enhance the accuracy of diagnosis and prognosis of certain diseases which affect the eye.

The ability to collect data of physiological importance in a spatially organized way, to store them for later retrieval and to display them in an enhanced image mode for easy interpretation provides a new horizon in ophthalmology.

In recent years, optical imaging methods and instrumentation for analyzing the ocular fundus have been making important progress. In particular, the integration of the optical techniques with sophisticated image processing by computer, are becoming more and more popular, because they contribute to the visualization of the pathology in vivo and to the quantification of the structure and functions or dysfunction involved therewith. In addition, it improves comparisons across time and can prevent loss of information (see Practical Atlas of Retinal Disease and Therapy, edited by William R. Freeman, Raven press, New York, 1993, p.19). Besides digital imaging by CCD cameras in conjunction with a fundus camera, the modem instrumentation includes Scanning Laser Ophthalmoscope (SLO), Laser Tomographic Scanner (LTS) (see Practical Atlas of Retinal Disease and Therapy, edited by William R. Freeman, Raven press, New York, 1993, p.19), Optic Nerve Analysis systems (Ophthalmic Photography, edited by Patrick J. Saine and Marshall E. Tyler, Butterworth-Heinemann, 1997, p. 269) and others, each of which employs a different and unique technology.

Different imaging modes are also used, such as "Confocal Imaging" and "Indirect Imaging" modes, to highlight and emphasize different features of the ocular fundus (see Practical Atlas of Retinal Disease and Therapy, edited by William R. Freeman, Raven press, New York, 1993, pp. 20 and 21).

It is also well known that imaging at specific wavelengths of visible light and the use of infrared light yields different types of information on the ocular fundus because different wavelengths are absorbed and scattered differently by the various fundus layers, anatomic structures (retina, choroid, vessels, pigment epithelium, sclera, etc.) and different depths (see Practical Atlas of Retinal Disease and Therapy, edited by William R. Freeman, Raven press, New York, 1993, p. 23, and Ophthalmic Photography, edited by Patrick J. Saine and Marshall E. Tyler, Butterworth-Heinemann, 1997, p. 71–73; see also U.S. Pat. application No. 08/942, 122, which is incorporated by reference as if fully set forth herein).

Fluorescein and Indocyanine Green Angiography are standard techniques used by the ophthalmologists for the analysis of vessels, blood flow, and related pathologies, and provide information critical to the diagnosis and treatment of eye diseases (Ophthalmic Photography, edited by Patrick J. Saine and Marshall E. Tyler, Butterworth-Heinemann, 1997, p. 261–263, and pp. 273–279 and Practical Atlas of Retinal Disease and Therapy, edited by William R. Freeman, Raven press, N.Y., 1993, pp. 25–29). Both of these tests use the intravenous injection of fluorescent dyes, which circulate in the blood, and allow the documentation of ocular vasculature and blood flow. Fluorescein Angiography (FA) is used for retinal vessels, while Indocyanine Green Angiography (ICG) has advantages for imaging the choroidal vessels, for example choroidal neovascularization (Ophthalmic Photography, edited by Patrick J. Saine and Marshall E. Tyler, Butterworth-Heinemann, 1997, p. 264, FIG. 7–34). Disadvantages of FA and ICG are that they require injection of a dye, which sometimes is dangerous, for example there is a requirement for screening patients for iodine allergy, and since the effect of the dye is dynamic, several images must be recorded between 2 and 60 minutes after injection.

Blood is a worse absorbent of infrared light than of visible light, so it is also useful to image features which are in the posterior layers or behind vessels or thin hemorrhages (see Ophthalmic Photography, edited by Patrick J Saine and Marshall E Tyler, Butterworth-Heinemann, 1997, p. 263, and the study by Elsner A E et al., Infrared imaging of sub-retinal structures in the human ocular fundus, Vision Res. 1996 Jan; 36(1): 191–205.).

In spite of what is known today on the wavelength dependence of fundus imaging of reflected white light, there is no commercial instrumentation which is used for imaging of choroidal vasculature and other features at or near the choroidal depth, based on the reflection of white light.

There is thus a widely recognized need for, and it would be highly advantageous to have methods of spectral bio-imaging of the eye which can be used for non-invasive early detection and diagnosis of eye associated diseases.

In particular, there is a widely recognized need for, and it would be highly advantageous to have an instrumentation and method capable of high quality imaging of choroidal vessels and similar tissues at or near the depth of the choroid, using high throughput spectral imaging instrumentation of white light reflection, or reflection imaging of successive monochromatic light illumination. Among the results of high throughput are that the system can be built with a reasonably small size and can measure at reasonably high speed, so that it is more efficient and therefore suitable for sale in larger quantities and as a consequence, at lower cost.

Another important advantage of the present invention over present methods of choroidal imaging is the avoidance of systemic dye injection and all related complications, for the clinic performing the test and for the patient receiving it.

SUMMARY OF THE INVENTION

According to the present invention there is provided a method for spectral imaging of an eye tissue, which can be used for non-invasive early detection and diagnosis of eye associated diseases and for detection of spatial organization, distribution and quantification of cellular and tissue natural constituents, structures and organelles, tissue vitality, tissue metabolism, tissue viability, etc., using light reflection, scattering and emission, with high spatial and spectral resolutions.

According to further features in preferred embodiments of the invention described below, there is provided a spectral bio-imaging method for enhancing spectral signatures of an eye tissue, the method comprising the steps of (a) providing an optical device for eye inspection being optically connected to a spectral imager; (b) illuminating the eye tissue with light via the iris, viewing the eye tissue through the optical device and spectral imager and obtaining a spectrum (e.g., full or portions thereof) of light for each pixel of the eye tissue; and (c) attributing each of the pixels a color or intensity according to its spectral signature (e.g., full or portions thereof), e.g., in a predefined spectral range, thereby providing an image enhancing the spectral signatures of the eye tissue. The optical device can be integrally formed with the spectral imager.

According to still further features in the described preferred embodiments there is provided a spectral bio-imaging method for extracting a spectral signature of a first portion of a layer of an object including at least two layers, each of the at least two layers has different spectral characteristics, the method comprising the steps of (a) providing an optical device being optically connected to a spectral imager; (b) illuminating the object with light, viewing the object through the optical device and spectral imager and obtaining a continuous spectrum of light for each pixel of the object; (c) using the continuous spectrum of light of each pixel of the object for generating a spectral image of the object in which the first portion is identifiable; (c) identifying in the spectral image the first portion of the layer and a second portion being adjacent to the first portion; and (d) accounting for spectral characteristics of the second layer, extracting the spectral signature of the first portion.

According to still further features in the described preferred embodiments the object is an ocular fundus, the at least two layers include a retinal layer and a choroidal layer and the first portion is selected from the group consisting of a retinal blood vessel and a choroidal blood vessel.

According to still further features in the described preferred embodiments the spectral signature is indicative of an oxygenation state of the first portion.

According to still further features in the described preferred embodiments the method further comprising the step of marking a mark indicative of the oxygenation state of the first portion on the spectral image in context of the first portion.

According to still further features in the described preferred embodiments the mark is a numerical value.

According to still further features in the described preferred embodiments the step of extracting the spectral signature of the first portion includes averaging over a plurality of the pixels.

According to still further features in the described preferred embodiments there is provided a method of evaluating a medical condition of a patient comprising the step of extracting a spectral signature of a retinal or choroidal blood vessel of a retina or choroid of an eye by (a) providing an optical device being optically connected to a spectral imager; (b) illuminating the eye with light, viewing the eye through the optical device and spectral imager and obtaining a continuous spectrum of light for each pixel of the eye; (c) using the continuous spectrum of light of each pixel of the eye for generating a spectral image of the eye in which the retinal or choroidal blood vessel is identifiable; (c) identifying in the spectral image the retinal or choroidal blood vessel and a tissue being adjacent to the retinal or choroidal blood vessel; (d) accounting for spectral characteristics of the tissue, extracting the spectral signature of the retinal or choroidal blood vessel; and (e) using the spectral signature to evaluate the medical condition of the patient.

According to still further features in the described preferred embodiments there is provided an apparatus for providing a display of an image presenting an eye tissue and a marking of an oxygenation state of at least one blood vessel therein, the apparatus comprising (a) an optical device for eye inspection being optically connected to a spectral imager; (b) an illumination source for illuminating the eye tissue with light via the iris; and (c) an image display device for displaying the image; wherein the image is realized by viewing the eye tissue through the optical device and spectral imager and obtaining a spectrum of light for each pixel of the eye tissue; by attributing each of the pixels a color or intensity according to its spectral signature, thereby providing the image enhancing the spectral signatures of the eye tissue; and further by marking in context of the at least one blood vessel the oxygenation state thereof.

According to still further features in the described preferred embodiments the spectral imager is selected from the group consisting of a filters based spectral imager, a monochromator based spectral imager (including successively monochromatic illumination spectral imaging) and an interferometer based spectral imager.

According to still further features in the described preferred embodiments the spectral imager is a high throughput spectral imager is selected from the group consisting of a wideband filters based spectral imager, decorrelation matched filters based spectral imager and an interferometer based spectral imager.

According to still further features in the described preferred embodiments step (b) includes (i) collecting incident light simultaneously from all pixels of the eye using collimating optics; (ii) passing the incident collimated light through an interferometer system having a number of elements, so that the light is first split into two coherent beams which travel in different directions inside the interferometer and then the two coherent beams recombine to interfere with each other to form an exiting light beam; (iii) passing the exiting light beam through a focusing optical system which focuses the exiting light beam on a detector having a two-dimensional array of detector elements; (iv) rotating or translating (scanning) one or more of the elements of the interferometer system, so that an optical path difference between the two coherent beams generated by the interferometer system is scanned simultaneously for all the pixels; and (v) recording signals of each of the detector elements as function of time using a recording device to form a spectral cube of data.

According to still further features in the described preferred embodiments the optical device is selected from the group consisting of a fundus camera and a funduscope.

According to still further features in the described preferred embodiments the spectrum of light represents light selected from the group consisting of, light reflected from the eye tissue, light scattered from the eye tissue and light emitted from the eye tissue.

According to still further features in the described preferred embodiments the light emitted from the eye tissue is selected from the group consisting of administered probe fluorescence, administered probe induced fluorescence and auto-fluorescence.

According to still further features in the described preferred embodiments the light used for illuminating the eye tissue is selected from the group consisting of coherent light, white light, filtered light, ultraviolet light, infrared light and a light having a small wavelength range.

According to still further features in the described preferred embodiments the two-dimensional array is selected from the group consisting of a video rate CCD, a cooled high dynamic range CCD, an intensified CCD and a time gated intensified CCD.

According to still further features in the described preferred embodiments the eye tissue is selected from the group consisting of eye retina, a retinal blood vessel an optic disk, an optic cup, eye macula, fovea, cornea, iris, lens, nerve fiber layer, choroid, choroidal layer, choroidal blood vessel, pigment epithelium and Bruch's membrane, or any combination thereof.

According to still further features in the described preferred embodiments the eye tissue includes a blood vessel, the method is for detecting and mapping the oxygenation level of hemoglobin along the blood vessel.

According to still further features in the described preferred embodiments step (c) is effected using a mathematical algorithm which computes a Red-Green-Blue color image using predefined wavelength ranges.

According to still further features in the described preferred embodiments step (c) is effected using a mathematical algorithm which computes a gray scale image using predefined wavelength ranges.

According to still further features in the described preferred embodiments the spectral signature and, as a result, the color is affected by a substance selected from the group consisting of hemoglobin, cytochromes, oxidases, reductases, flavins, nicotinamide adenine dinucleotide, nicotinamide adenine dinucleotide phosphate, collagen, elastin, xanthophyll and melanin.

According to still further features in the described preferred embodiments enhancing the spectral signatures of the eye tissue includes an enhancement selected from the group consisting of enhancing arteries, enhancing veins, enhancing hemoglobin concentration, enhancing hemoglobin oxygen saturation level and melanoma and hemangioma lesions.

According to still further features in the described preferred embodiments the method further comprising the step of correcting spatial and spectral information for movements of the eye tissue via a spatial registration and spectral correction procedures.

According to still further features in the described preferred embodiments there is provided a method of evaluating a medical condition of a patient comprising the step of enhancing spectral signatures of an eye tissue of the patient by (a) providing an optical device for eye inspection being optically connected to a spectral imager, e.g., a high throughput spectral imager; (b) illuminating the eye tissue of the patient with light via the iris, viewing the eye tissue through the optical device and spectral imager and obtaining a light spectrum for each pixel of the eye tissue; (c) attributing each of the pixels a color or intensity according to its spectral signature, e.g., in a predefined spectral range, thereby providing an image enhancing the spectral signatures of the eye tissue; and (d) using the image to evaluate the medical condition of the patient. The optical device can be integrally formed with the spectral imager.

According to still further features in the described preferred embodiments the medical condition is selected from the group consisting of diabetic retinopathy, ischemia of the eye, glaucoma, macular degeneration, CMV eye infection, melanoma lesions, hemangioma lesions, retinitis, choroidal ischemia, acute sectorial choroidal ischemia, ischemic optic neuropathy, and corneal and iris problems.

Further according to the present invention there is provided an apparatus for providing a display of an image presenting an eye tissue, wherein each pixel in the image is assigned a color or intensity according to a spectral signature of a tissue element from which it is derived, thereby enhancing the spectral signature of the eye tissue comprising (a) an optical device for eye inspection being optically connected to a spectral imager, e.g., a high throughput spectral imager; (b) an illumination source for illuminating the eye tissue with light via the iris; and (c) an image display device for displaying the image; wherein the image is realized by viewing the eye tissue through the optical device and spectral imager and obtaining a spectrum of light for each pixel of the eye tissue; and further by attributing each of the pixels a color or intensity according to its spectral signature, e.g., in a predefined spectral range, thereby providing the image enhancing the spectral signatures (e.g., in full or parts thereof) of the eye tissue.

According to still further features in the described preferred embodiments there is provided a spectral bio-imaging method for obtaining a spectrum of a region (corresponding to a pixel or few pixels in the image) of an eye tissue, the method comprising the steps of (a) providing an optical device for eye inspection being optically connected to a spectral imager, e.g., a high throughput spectral imager; (b) illuminating the eye tissue with light via the iris, viewing the eye tissue through the optical device and spectral imager and obtaining a spectrum of light for each pixel of the eye tissue; and (c) displaying a spectrum (a spectrum of a single pixel or an average spectrum of several pixels) associated with the region of interest. Spectra of specific regions in the eye are known in the art, however using the above method enables a practitioner to precisely select a region of interest, such that the spectrum obtained is the spectrum of interest. The optical device can be integrally formed with the spectral imager.

Further according to the present invention there is provided a spectral bio-imaging method for enhancing spectral signatures of at least two eye tissues, each of a different spectral signature, the method comprising the steps of (a) providing an optical device for eye inspection being optically connected to a spectral imager; (b) illuminating the eye tissue with light via the iris, viewing the eye tissue through the optical device and spectral imager and obtaining a spectrum of light for each pixel of the eye tissue; and (c) selecting spectral ranges highlighting the different spectral signatures of each of the at least two eye tissues; and (d) generating an image enhancing the different spectral signatures of the at least two eye tissues. The optical device can be integrally formed with the spectral imager.

Further according to the present invention there is provided a spectral bio-imaging method for enhancing blood vessels of an eye tissue, the method comprising the steps of (a) providing an optical device for eye inspection being optically connected to a spectral imager; (b) illuminating the eye tissues with light via the iris, viewing the eye tissue through the optical device and spectral imager and obtaining a spectrum of light for each pixel of the eye tissue; (c) employing an algorithm highlighting a spectral signature of blood vessels; and (d) generating an image enhancing the blood vessels. The optical device can be integrally formed with the spectral imager.

Further according to the present invention there is provided an apparatus for providing a display of an image presenting an eye tissue in which blood vessels are enhanced by a color or intensity according to a spectral signature specific thereto, the apparatus comprising (a) an optical device for eye inspection being optically connected to a spectral imager; (b) an illumination source for illuminating the eye tissue with light via the iris; and (c) an image display device for displaying the image; wherein the image is realized by viewing the eye tissue through the optical device and spectral imager and obtaining a spectrum of light for each pixel of the eye tissue; and further by attributing each of the pixels a color or intensity according to its spectral signature, thereby enhancing the spectral signature of blood vessels in the eye tissue.

The present invention successfully addresses the shortcomings of the presently known configurations by providing an image of the eye which enhances spectral signatures of constituents thereof, characterized by high spatial and spectral resolutions.

BRIEF DESCRIPTION OF THE DRAWINGS

The file of this patent contains at least one drawing executed in color. Copies of this patent with color drawings will be provided by the Patent and Trademark Office upon request and payment of the necessary fee.

The invention herein described, by way of example only, with reference to the accompanying drawings, wherein:

FIG. 5a presents a portion of an interferogram function of a given pixel derived from the spectral image of FIG. 4a.

FIG. 6a presents spectra of five adjacent pixels derived from the spectral image of FIG. 4a, the position of each pixel is indicated.

FIG. 6b presents spectra of five adjacent pixels derived from the spectral image of FIG. 4b, the position of each pixel is indicated.

FIGS. 19a–e present an RGB image, a 610 and 564 nm images, a hemoglobin concentration image and an image of an optic disk of a glaucoma patient.

FIGS. 30a–b demonstrates the user interface in which three regions (marked 1–3) are used: 1 —region of interest; 2 —region including the boundaries of region 1; and 3 —region including the surroundings.

FIG. 31 demonstrates the process of slicing the region of interest with its surrounding into slices along the equator of the region of interest. A collection of measured—$\ln(I_N/I_{N-1})$ is obtained (blue curves). A model fitting (red curves) to the measured $d\ln(I_N/I_{N-1})Id\lambda$ is done for each slice separately according to Equation 39.

DESCRIPTION OF THE PREFERRED EMBODIMENTS

Figure 1:
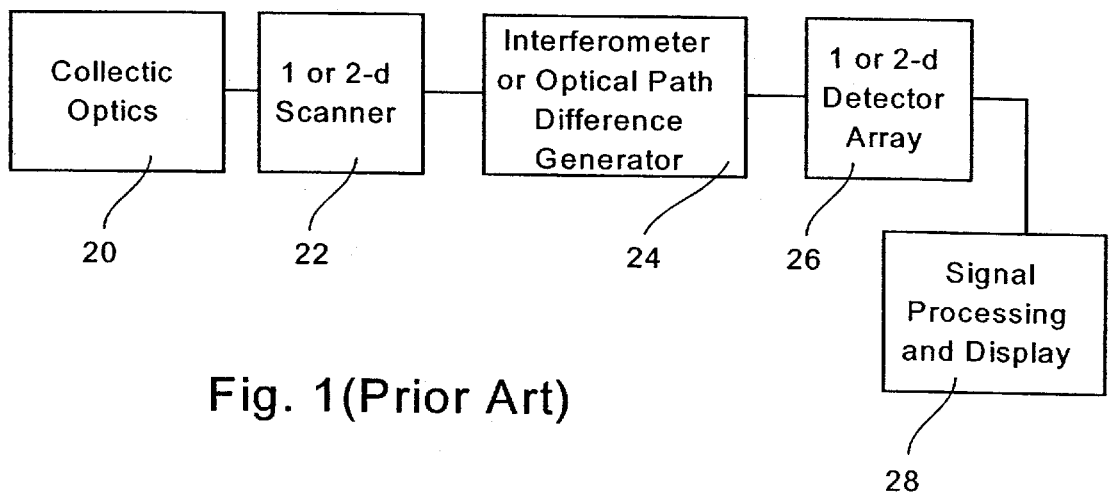
FIG. 1 is a block diagram illustrating the main components of an imaging spectrometer constructed in accordance with U.S. Pat. No. 5,539,517 (prior art).

The present invention is of a method for spectral bio-imaging of the eye which can be used for non-invasive early detection and diagnosis of eye diseases. Specifically, the present invention can be used for detection of spatial organization, distribution and quantification of cellular and tissue natural constituents, structures and organelles, tissue vitality, tissue metabolism, tissue viability, etc., using light reflection, scattering and emission, with high spatial and spectral resolutions.

The principles and operation of a method according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

The present invention is of a spectral bio-imaging method for enhancing spectral signatures of an eye tissue (e.g., ocular fundus tissue, choroidal tissue, etc.). The method is effected executing the following method steps. First, an optical device for eye inspection, such as, but not limited to, a funduscope or a fundus camera, which is optically connected to a spectral imager, e.g., a high throughput spectral imager, is provided. Second, the eye tissue is illuminated with light via the iris, the eye tissue is viewed through the optical device and spectral imager and a light spectrum for each pixel of the eye tissue is obtained.

Third, each of the pixels is attributed a color or intensity according to its spectral signature, e.g., in a predefined spectral range, thereby an image enhancing the spectral signatures of the eye tissue is provided. As used herein the term "spectral range" also refers to a single wavelength. As further described hereunder, it is sometimes advantageous to highlight different portions or tissues of the eye by using different spectral regions for different tissues or portions.

For many of the embodiments according to the present invention any spectral imager may be used to perform the measurement. Suitable spectral imagers include, for example, a filters based spectral imager, a monochromator (grating/prism) based spectral imager and or an interferometer based spectral imager. A description concerning the operation and construction advantages and disadvantages of each of these spectral imagers is provided in the Background section above and the Examples section that follows.

However, some embodiments according to the present invention can be efficiently realized only with a high throughput spectral imager (see example 5 and the rational therein).

As used herein in the specification and in the claims section below, the term "high throughput" refers to an ability of a spectral imaging device to efficiently utilize available photons. It is based on an optical light collection concept which in order to provide spectral information, does not need to do either of the following: (i) filter out photons outside each wavelength of the spectral range of interest, as done by spectral imagers employing a plurality of narrow band filters; (ii) block the light coming from pixels outside a narrow region of the image, as done by a spectral imager employing a grating or prism, by a limiting slit. Thus, as used herein, the term refers to the ability of the part of the imager that provides the spectral information (e.g., wide band filters, decorrelation filters, interferometer) to collect at least about 30%, preferably at least about 40%, more preferably a least about 50%, most preferably at least about 60%, ideally, above about 60%, say between 60% and the theoretical value of 100%, of the photons to which the collection optics of the imager is exposed to.

Examples of high throughput spectral imagers useful at implementing the method according to the present invention are provided in the Examples section below (see Example 1)

According to a preferred embodiment of the invention the spectral imager includes an interferometer. In this case, step (b) above includes, for example, the following: (i) collecting incident light simultaneously from all pixels of the eye using collimating optics; (ii) passing the incident collimated light through an interferometer system having a number of elements, so that the light is first split into two coherent beams which travel in different directions inside the interferometer and then the two coherent beams recombine to interfere with each other to form an exiting light beam; (iii) passing the exiting light beam through a focusing optical system which focuses the exiting light beam on a detector having a two-dimensional array of detector elements; (iv) rotating or translating (scanning) one or more of the elements of the interferometer system, so that an optical path difference between the two coherent beams generated by the interferometer system is scanned simultaneously for all the pixels; and (v) recording signals of each of the detector elements as function of time using a recording device to form a spectral cube of data.

According to a preferred embodiment of the invention the two-dimensional array is selected from the group consisting of a video rate CCD, a cooled high dynamic range CCD, an intensified CCD and a time gated intensified CCD.

Be it an interferometer based spectral imager or any other spectral imager, the light analyzed to derive a spectrum of each of the pixels of the eye tissue may be light reflected from the eye tissue, light scattered from the eye tissue and/or light emitted from the eye tissue. The light emitted from the eye tissue may be due to administered probe fluorescence, administered probe induced fluorescence and/or autofluorescence of the eye tissue.

Depending on the specific application and the spectral imager, the light used for illuminating the eye tissue is, for example, coherent light (e.g., laser), white light, filtered light, ultraviolet light, infrared light and a light having a small wavelength range (e.g., LED produced light).

Any eye tissue is suitable for examination using the method of the present invention, including, but not limited to, eye retina, a retinal blood vessel, an optic disk, an optic cup, eye macula, fovea, cornea, iris, lens, nerve fiber layer, choroid, choroidal layer, choroidal blood vessel, pigment epithelium and Bruch's membrane. In many cases, the eye tissue includes blood vessels and the method serves for enhancing the vessels or for detecting and mapping the oxygenation level and/or concentration of hemoglobin along any of the blood vessel, veins and/or arteries.

Effecting step (c) above may be accomplished in many ways, for example, using any of the algorithms described under Example 2 below. However, in a preferred embodiment step (c) is effected using a mathematical algorithm which computes a Red-Green-Blue color image or a gray level (scale) image using predefined wavelength ranges, all as further described in the Examples section below. Thus, as used herein the term "color" refers also to black, gray and white.

In a preferred embodiment of the invention, the spectral signature of the eye tissue and, as a result, the color of each pixel is affected by a substance such as hemoglobin, cytochromes, oxidases, reductases, flavins, nicotinamide adenine dinucleotide, nicotinamide adenine dinucleotide phosphate, collagen, elastin, xanthophyll and/or melanin. The color of each pixel represents the content or concentration of any one or more of these materials or, except for collagen, elastin, xanthophyll and melanin, the ratio between their oxidized (e.g., oxygenated, dehydrogenated) and reduced (e.g., hydrogenated, deoxygenated) forms.

According to the present invention enhancing the spectral signatures of the eye tissue may include enhancement of physiological structures such as arteries and veins and/or levels of biological substances such as melanoma lesions, hemangioma lesions, hemoglobin concentration and oxygen saturation level, which is indicative to the level of metabolism and/or vitality of the tissue.

According to another preferred embodiment of the invention the spectral imager employed includes an interferometer and a module for effecting a procedure for correcting spatial and spectral information for movements of the eye tissue via spatial registration and spectral correction. For other imagers, spatial registration, as well known in the art, can be employed, if so required. Mechanically and/or chemically fixating the analyzed eye obviates the need for these procedures.

As is evident from the examples below, the method according to the present invention can be used for evaluating a medical condition of a patient. The medical evaluation method includes steps (a)-(c), substantially as described hereinabove and further includes a medical evaluation procedure using the image obtained. The medical condition may be any condition that affects the eye, including, but not limited to, diabetic retinopathy, ischemia of the eye, glaucoma, macular degeneration, CMV eye infection (cytomegalovirus eye infection of AIDS patients), CMV eye infection, melanoma lesions, hemangioma lesions, retinitis, choroidal ischemia, acute sectorial choroidal ischemia, ischemic optic neuropathy, and corneal and iris problems.

Further according to the present invention there is provided an apparatus for generating a display which includes an image presenting an eye tissue, wherein each pixel in the image has a color or intensity according to a spectral signature of a tissue element (part of a tissue which is equivalent to a pixel in the image, depending on spatial resolution) from which it is derived, thereby enhancing the spectral signatures of the eye tissue. The term "display" as used herein refers to any visual presentation such as, but not limited to, a photograph, a print, screen display or a monitor display, which can be materialized by a camera, a printer, a screen and a monitor, respectively.

The apparatus thus includes (a) an optical device for eye inspection being optically connected to a spectral imager, e.g., a high throughput spectral imager; (b) an illumination source for illuminating the eye tissue with light via the iris; and (c) an image display device for displaying the image. The image is realized by viewing the eye tissue through the optical device and spectral imager and obtaining a spectrum of light for each pixel of the eye tissue, and further by attributing each of the pixels a color or intensity according to its spectral signature, e.g., in a predefined spectral range, thereby providing the image enhancing the spectral signatures of the eye tissue.

Still further according to the present invention there is provided a spectral bio-imaging method for obtaining a spectrum of a region (corresponding to a pixel or few pixels in the image) of an eye tissue. The method is effected by executing the following method steps.

First, an optical device for eye inspection, such as, but not limited to, a funduscope or a fundus camera, which is optically connected to a spectral imager is provided.

Second, the eye tissue is illuminated with light via the iris, the eye tissue is viewed through the optical device and spectral imager and a light spectrum for each pixel of the eye tissue is obtained.

And third, a spectrum (a spectrum of a single pixel or an average spectrum of several pixels) associated with the region of interest is displayed.

Yet, still further according to the present invention there is provided a spectral bio-imaging method for enhancing spectral signatures of at least two eye tissues, each of a different spectral signature. The method is effected by (a) providing an optical device for eye inspection being optically connected to a spectral imager; (b) illuminating the eye tissue with light via the iris, viewing the eye tissue through the optical device and spectral imager and obtaining a spectrum of light for each pixel of the eye tissue; and (c) selecting spectral ranges highlighting the different spectral signatures of each of the at least two eye tissues; and (d) generating an image enhancing the different spectral signatures of the at least two eye tissues. The applicability of this method is demonstrated in Example 5 below. The optical device can be integrally formed with the spectral imager.

Further according to the present invention there is provided a spectral bio-imaging method for enhancing blood vessels of an eye tissue. The method is effected by (a) providing an optical device for eye inspection being optically connected to a spectral imager; (b) illuminating the eye tissues with light via the iris, viewing the eye tissue through the optical device and spectral imager and obtaining a spectrum of light for each pixel of the eye tissue; (c) employing an algorithm highlighting a spectral signature of blood vessels; and (d) generating an image enhancing the blood vessels. The applicability of this method is demonstrated in Example 6 below. The optical device can be integrally formed with the spectral imager.

Further according to the present invention there is provided an apparatus for providing a display of an image presenting an eye tissue in which blood vessels are enhanced by a color or intensity according to a spectral signature specific thereto. The apparatus includes (a) an optical device for eye inspection being optically connected to a spectral imager; (b) an illumination source for illuminating the eye tissue with light via the iris; and (c) an image display device for displaying the image; wherein the image is realized by viewing the eye tissue through the optical device and spectral imager and obtaining a spectrum of light for each pixel of the eye tissue; and further by attributing each of the pixels a color or intensity according to its spectral signature, thereby enhancing the spectral signature of blood vessels in the eye tissue. The applicability of this apparatus is demonstrated in Example 6 below.

Further according to the present invention there is provided a spectral bio-imaging method for extracting a spectral signature of a first portion of a layer of an object which includes at least two layers, wherein each of the two layers has different spectral characteristics. The method according to this aspect of the present invention is effected by implementing the following method steps, in which, in a first step, an optical device which is optically connected to a spectral imager is provided. Then, the object is illuminated with light and is viewed through the optical device and spectral imager. Thereby, a continuous spectrum of light for each pixel of the object is obtained. The continuous spectrum of light of each pixel of the object are then used for generating a spectral image of the object in which the first portion is identifiable. Thereafter, the first portion of the layer and a second portion which is adjacent to the first portion in the spectral image are identified. Finally, taking into account the spectral characteristics of the second layer, spectral signature of the first portion is extracted.

The above method can be employed, as further detailed hereunder for evaluating the oxygenation state of a blood vessel. In one example, the object is an ocular fundus, the at least two layers include a retinal layer and a choroidal layer and the first portion is a retinal blood vessel and a choroidal blood vessel.

According to a preferred embodiment the method further includes a step of marking a mark indicative of the oxygenation state of the first portion on the spectral image in context of the first portion. The mark can be an indicative color and/or a numerical value.

In addition, according to preferred embodiments and for better and more accurate results, the step of extracting the spectral signature of the first portion includes averaging over a plurality of the pixels.

Further according to the present invention there is provided a method of evaluating a medical condition of a patient. The method is effected by implementing the following method steps, in which, a spectral signature of a retinal or choroidal blood vessel of a retina or choroid of an eye is extracted by (a) providing an optical device being optically connected to a spectral imager; (b) illuminating the eye with light, viewing the eye through the optical device and spectral imager and obtaining a continuous spectrum of light for each pixel of the eye; (c) using the continuous spectrum of light of each pixel of the eye for generating a spectral image of the eye in which the retinal or choroidal blood vessel is identifiable; (c) identifying in the spectral image the retinal or choroidal blood vessel and a tissue being adjacent to the retinal or choroidal blood vessel; (d) accounting for spectral characteristics of the tissue, extracting the spectral signature of the retinal or choroidal blood vessel; and (e) using the spectral signature to evaluate the medical condition of the patient.

The implementation and use of the last two methods according to the present invention are further described and exemplified in Example 7 below.

Further according to the present invention there is provided an apparatus for providing a display of an image presenting an eye tissue and a marking of an oxygenation state of at least one blood vessel therein. The apparatus according to this aspect of the present invention includes an optical device for eye inspection which is optically connected to a spectral imager. The apparatus further includes an illumination source for illuminating the eye tissue with light via the iris. The apparatus further includes an image display device for displaying the image. The image itself is realized by viewing the eye tissue through the optical device and spectral imager and obtaining a spectrum of light for each pixel of the eye tissue; attributing each of the pixels a color or intensity according to its spectral signature, thereby providing the image enhancing the spectral signatures of the eye tissue; and further by marking in context of the blood vessel(s) the oxygenation state thereof.

Reference in now made to the following examples, which together with the above descriptions, illustrate the invention.

EXAMPLE 1

THE MEASUREMENT APPARATUS

FIG. 1 is a block diagram illustrating the main components of a prior art imaging spectrometer disclosed in U.S. Pat. No. 5,539,517. This imaging spectrometer is constructed highly suitable to implement the method of the present invention as it has high spectral (Ca. 4–14 nm depending on wavelength) and spatial (Ca. 30/M $\mu$m where M is the effective microscope or fore optics magnification) resolutions.

Thus, the prior art imaging spectrometer of FIG. 1 includes: a collection optical system, generally designated 20; a one-dimensional scanner, as indicated by block 22; an optical path difference (OPD) generator or interferometer, as indicated by block 24; a one-dimensional or two-dimensional detector array, as indicated by block 26; and a signal processor and display, as indicated by block 28.

A critical element in system 20 is the OPD generator or interferometer 24, which outputs modulated light corresponding to a predetermined set of linear combinations of the spectral intensity of the light emitted from each pixel of the scene to be analyzed. The output of the interferometer is focused onto the detector array 26.

Thus, all the required optical phase differences are scanned simultaneously for all the pixels of the field of view, in order to obtain all the information required to reconstruct the spectrum. The spectra of all the pixels in the scene are thus collected simultaneously with the imaging information, thereby permitting analysis of the image in a real-time manner.

The apparatus according to U.S. Pat. No. 5,539,517 may be practiced in a large variety of configurations. Specifically, the interferometer used may be combined with other mirrors as described in the relevant Figures of U.S. Pat. No. 5,539,517.

Thus, according to U.S. Pat. No. 5,539,517 alternative types of interferometers may be employed. These include (i) a moving type interferometer in which the OPD is varied to modulate the light, namely, a Fabry-Perot interferometer with scanned thickness; (ii) a Michelson type interferometer which includes a beamsplitter receiving the beam from an optical collection system and a scanner, and splitting the beam into two paths; (iii) a Sagnac interferometer optionally combined with other optical means in which interferometer the OPD varies with the angle of incidence of the incoming radiation, such as the four-mirror plus beamsplitter interferometer as further described in the cited U.S. patent (see FIG. 14 there).

Figure 2:
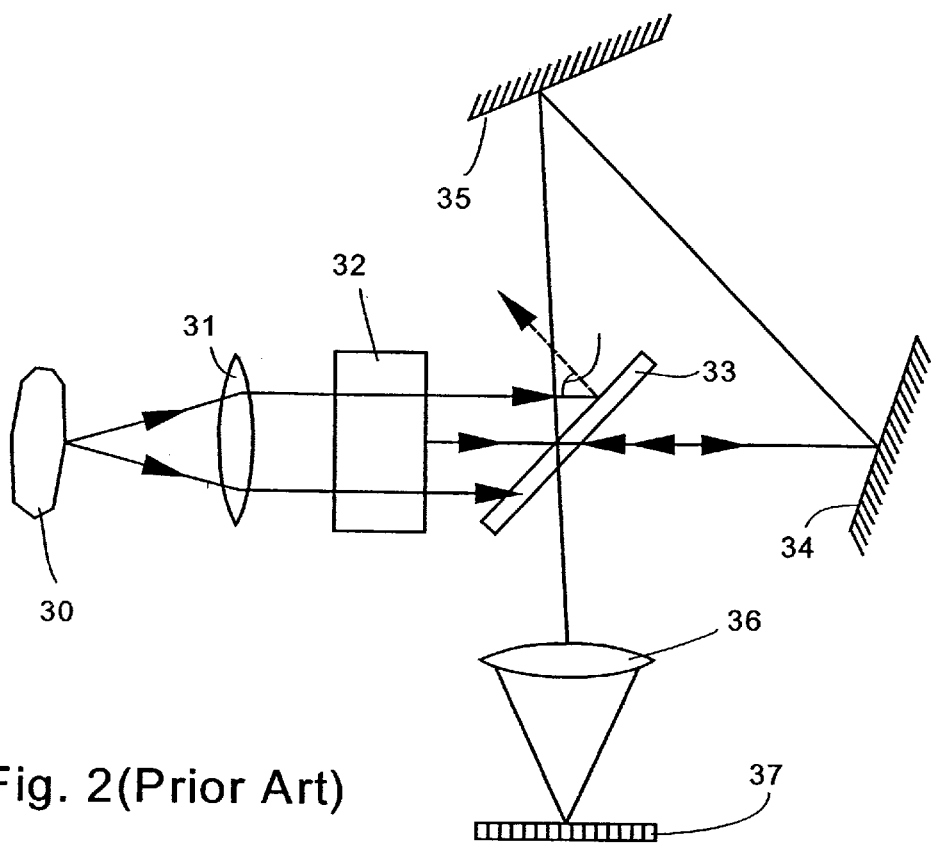
FIG. 2 illustrates a Sagnac interferometer, as used in an imaging spectrometer in accordance with U.S. Pat. No. 5,539,517 (prior art).

FIG. 2 illustrates an imaging spectrometer constructed in accordance with U.S. Pat. No. 5,539,517, utilizing an interferometer in which the OPD varies with the angle of incidence of the incoming radiation. A beam entering the interferometer at a small angle to the optical axis undergoes an OPD which varies substantially linearly with this angle.

In the interferometer of FIG. 2, all the radiation from source 30 in all the pixels, after being collimated by an optical collection system 31, is scanned by a mechanical scanner 32. The light is then passed through a beamsplitter 33 to a first reflector 34 and then to a second reflector 35, which reflects the light back through the beamsplitter 33 and then through a focusing lens 36 to an array of detectors 37 (e.g., a CCD). This beam interferes with the beam which is reflected by 33, then by second reflector 35, and finally by first reflector 34.

At the end of one scan, every pixel has been measured through all the OPD's, and therefore the spectrum of each pixel of the scene can be reconstructed by Fourier transformation. A beam parallel to the optical axis is compensated, and a beam at an angle ($\theta$) to the optical axis undergoes an OPD which is a function of the thickness of the beamsplitter 33, its index of refraction, and the angle $\theta$. The OPD is proportional to $\theta$ for small angles. By applying the appropriate inversion, and by careful bookkeeping, the spectrum of every pixel is calculated.

In the configuration of FIG. 2 the ray which is incident on the beamsplitter at an angle $\beta$ ($\beta=45°$ in FIG. 2) goes through the interferometer with an OPD=0, whereas a ray which is incident at a general angle $\beta-\theta$ undergoes an OPD given by the following:

$$OPD(\beta,\theta,t,n)=t[(n^2-\sin^2(\beta+\theta))^{0.5}-(n^2-\sin^2(\beta-\theta))^{0.5}+2\sin\beta \sin\theta] \quad (1)$$

where $\beta$ is the angle of incidence of the ray on the beamsplitter; $\theta$ is the angular distance of a ray from the optical axis or interferometer rotation angle with respect to the central position; t is the thickness of the beamsplitter; and n is the index of refraction of the beamsplitter.

It follows from Equation 1 that by scanning both positive and negative angles with respect to the central position, one gets a double-sided interferogram for every pixel, which helps eliminate phase errors giving more accurate results in the Fourier transform calculation. The scanning amplitude determines the maximum OPD reached, which is related to the spectral resolution of the measurement. The size of the angular steps determines the OPD step which is, in turn, dictated by the shortest wavelength to which the system is sensitive. In fact, according to the sampling theorem [see, Chamberlain (1979) The principles of interferometric spectroscopy, John Wiley and Sons, pp. 53–55], this OPD step must be smaller than half the shortest wavelength to which the system is sensitive.

Another parameter which should be taken into account is the finite size of a detector element in the matrix. Through the focusing optics, the element subtends a finite OPD in the interferometer which has the effect of convolving the interferogram with a rectangular function. This brings about, as a consequence, a reduction of system sensitivity at short wavelengths, which drops to zero for wavelengths equal to or below the OPD subtended by the element. For this reason, one must ensure that the modulation transfer function (MTF) condition is satisfied, i.e., that the OPD subtended by a detector element in the interferometer must be smaller than the shortest wavelength at which the instrument is sensitive.

Thus, imaging spectrometers constructed in accordance with the invention disclosed in U.S. Pat. No. 5,539,517 do not merely measure the intensity of light coming from every pixel in the field of view, but also measure the spectrum of each pixel in a predefined wavelength range. They also better utilize all the radiation emitted by each pixel in the field of view at any given time, and therefore permit, as explained above, a significant decrease in the frame time and/or a significant increase in the sensitivity of the spectrometer. Such imaging spectrometers may include various types of interferometers and optical collection and focusing systems, and may therefore be used in a wide variety of applications, including medical diagnostic and therapy and biological research applications, as well as remote sensing for geological and agricultural investigations, and the like.

As mentioned above, an imaging spectrometer in accordance with the invention disclosed in U.S. Pat. No. 5,539, 517 was developed by Applied Spectral Imaging Ltd., Industrial Park, Migdal Haemek, Israel and is referred herein as SPECTRACUBE.

The SPECTRACUBE system optically connected to a microscope is used to implement the method for chromosome classification of the present invention. The SPECTRACUBE system has the following or better characteristics, listed hereinbelow in Table 1 below.

The prior art SPECTRACUBE system was used, in accordance with the present invention, to acquire spatially organized spectral data from the eye.

The prior art SPECTRACUBE system was used, in accordance with the present invention, to acquire spatially organized spectral data from the eye. However, it will be appreciated that any spectral imager, i.e., an instrument that measures and stores in memory for later retrieval and analysis the spectrum of light emitted by every point of an object which is placed in its field of view, including filter (e.g., acousto-optic tunable filters (AOTF) or liquid-crystal tunable filter (LCTF)) and dispersive element (e.g., grating or prism) based spectral imagers, or other spectral data or multi-band collection devices (e.g., a device in accordance with the disclosure in Speicher R. M., Ballard S. G. and Ward C. D. (1996) Karyotyping human chromosomes by combinatorial multi-flour FISH. Nature genetics, 12:368–375) can be used to acquire the required spectral data. Therefore, it is intended not to limit the scope of the present invention for use of any specific type of spectral data collection devices, nor any specific type of spectral imager.

TABLE 1

| Parameter | Performance |
|---|---|
| Spatial resolution: | 30/M μm (M = effective microscope or fore optics magnification) |
| Field of View: | 15/M millimeters |
| Sensitivity: | 20 milliLux (for 100 msec integration time, increases for longer integration times linearly with √T) |
| Spectral range: | 400–1000 nm |
| Spectral resolution: | 4 nm at 400 nm (16 nm at 800 nm) |
| Acquisition time: | 5–50 sec, typical 25 sec |
| FFT processing time: | 20–180 sec, typical 60 sec |

As mentioned above, the SPECTRACUBE system easily attaches to any microscope or macro lens with, for example, C-mount or F-mount connectors, and can stand in any orientation during the measurement. The system may as well be connected to other magnification means and to various types of endoscopes and cameras including funduscopes and fundus cameras. Therefore, spectral images of the eye tissue in various magnification and lighting may be obtained.

For some applications according to the present invention (see Example 4) a high throughput spectral imager is required.

Thus, various possible configurations of a high throughput spectral imager based on Fourier Transform interferometry have been described in U.S. Pat. No. 5,539, 517, of which the imager based on a Sagnac interferometer has been commercialized by Applied Spectral Imaging Ltd., and sold as the SPECTRACUBE™ models SD 200 and 300. Many other publications describing the SPECTRACUBE and several of its applications have been published during the last three years (see above). The feature distinguishing high throughput spectral imagers from other types, such as those based on filtering the reflected, transmitted or emitted light with narrow band filters or dispersing it with a grating or a prism, is that the former type makes a more efficient use of the photons available for measurement, especially when the origin of noise is random and is independent of signal (see R. J. Bell, *Introductory Fourier Transform Spectroscopy*, Academic Press 1972, pp. 23–25 and J. Chamberlain, *The Principles of Interferometric Spectroscopy*, John Wiley & Sons 1979, pp. 305–306, in reference to Fourier Transform Spectroscopy versus filters or grating spectroscopy), and in certain cases of photon shot noise limitations.

Another high throughput Fourier transform spectral imaging system is distributed by BioRad Laboratories under the trade name of STINGRAY 6000. This system is described in "Fourier Transform Spectroscopic Imaging Using an Infrared Focal-Plane Array Detector", by E. Neil Lewis et al., Analytical Chemistry, Vol. 67, No. 19, Oct. 1, 1995, pp. 3377–3381. Its histopathological applications are described in Infrared Spectroscopic Imaging as a Tool for Pathology, by Linda H. Kidder et al., SPIE Proceedings Vol. No. 3257, pp.178–186. Both references are incorporated by reference as if fully set forth herein.

Other types of high throughput spectral imagers are described in U.S. Pat. No. 5,719,024, which is incorporated by reference as if fully set forth herein and relates to matched decorrelation filters of wide spectral coverage.

As taught by U.S. Pat. application No. 08/917,213, which is incorporated by reference as if fully set forth herein, other types of high throughput spectral imagers are based on different sets of wide band filters whose spectral transmission characteristics are chosen according to predetermined criteria, suitable for each specific application. The technology on which these filters are based can be of many types, e.g., interference filters, multilayer interference filters, narrow band and wide band filters, Liquid Crystal Filters, Acousto-Optic Tunable Filters, stained glasses, cut-ons, cut-offs, and others, and all the combinations thereof.

U.S. Pat. application 09/143,964, filed Aug. 30, 1998, which is incorporated by reference as if fully set forth herein, teaches monochromatic illumination of the sample by an array of LED sources combined with dispersion by grating.

All of the these high throughput spectral imagers are suitable or readily adapted for use in combination with a fundus camera as described in U.S. Pat. application Nos. 08/942,122 and 09/143,964.

It will be appreciated that researchers have tried the use of narrow band filters for monochromatic imaging of the retina and/or ocular fundus in the past, without success. It is assumed that the photon rejection of such instrumentation is so high that the measurement time at each wavelength is too long for a meaningful result to be obtained in a reasonable time, due to eye movement and other practical constraints. In principle, these difficulties may be overcome using specially designed algorithms or other solutions, but because of their complexity, development time, etc., the barriers encountered have been discouraging enough that no commercial instrumentation of this type is available today.

In any case, to conduct the present study the SPECTRACUBE system was mounted on the CCD port of a fundus camera (Zeiss Model RC-310) and the combined system was situated such that the optical path was substantially horizontal. This facilitates eye inspection, wherein the patient is seated. A white light source was used for illumination of the eye and reflected light was collected and analyzed.

EXAMPLE 2

DISPLAY AND ANALYSIS OF SPECTRAL IMAGES a. General

As mentioned above, a spectral image is a three dimensional array of data, $I(x,y,\lambda)$, that combines spectral information with spatial organization of the image.

As such, a spectral image is a set of data called a spectral cube, due to its dimensionality, which enables the extraction of features and the evaluation of quantities that are difficult, and in some cases even impossible, to obtain otherwise.

Since both spectroscopy and digital image analysis are well known fields that are covered by an enormous amount of literature [see, for example, Jain (1989) Fundamentals of Digital Image Processing, Prentice-Hall International], the following discussion will focus primarily on the benefit of combining spectroscopic and imaging information in a single data set i.e., a spectral cube.

One possible type of analysis of a spectral cube is to use spectral and spatial data separately, i.e., to apply spectral algorithms to the spectral data and two-dimensional image processing algorithms to the spatial data.

As an example for a spectral algorithm consider an algorithm computing the similarity between a reference spectrum and the spectra of all pixels (i.e., similarity mapping) resulting in a gray (or other color) scale image (i.e., a similarity map) in which the intensity at each pixel is proportional to the degree of 'similarity'.

This gray scale image can then be further analyzed using image processing and computer vision techniques (e.g., image enhancement, pattern recognition, etc.) to extract the desired features and parameters.

In other words, similarity mapping involves computing the integral of the absolute value of the difference between the spectrum of each pixel of the spectral image with respect to a reference spectrum (either previously memorized in a library, or belonging to a pixel of the same or other spectral image), and displaying a gray level or pseudocolor (black and white or color) image, in which the bright pixels correspond to a small spectral difference, and dark pixels correspond to a large spectral difference, or vice versa.

Similarly, classification mapping perform the same calculation as described for similarity mapping, yet takes several spectra as reference spectra, and paints each pixel of the displayed image with a different predetermined pseudocolor, according to its classification as being most similar to one of the several reference spectra.

It is also possible to apply spectral image algorithms based on non-separable operations; i.e., algorithms that include both local spectral information and spatial correlation between adjacent pixels (one of these algorithms is, as will be seen below, a principal component analysis).

One of the basic needs that arise naturally when dealing with any three-dimensional (3D) data structure such as a spectral cube (i.e., $I(x,y,\lambda)$), is visualizing that data structure in a meaningful way. Unlike other types of 3D data such as topographic data, $D(x,y,z)$, obtained, for example, by a confocal microscope, where each point represents, in general, the intensity at a different locations $(x,y,z)$ in tree-dimensional space, a spectral image is a sequence of images representing the intensity of the same two-dimensional plane (i.e., the sample) at different wavelengths. For this reason, the two most intuitive ways to view a spectral cube of data is to either view the image plane (spatial data) or the intensity of one pixel or a set of pixels as function of wavelength in a three-dimensional mountain-valley display. In general, the image plane can be used for displaying either the intensity measured at any single wavelength or the gray scale image that results after applying a spectral analysis algorithm, over a desired spectral region, at every image pixel. The spectral axis can, in general, be used to present the resultant spectrum of some spatial operation performed in the vicinity of any desired pixel (e.g., averaging the spectrum).

It is possible, for example, to display the spectral image as a gray scale image, similar to the image that might be obtained from a simple monochrome camera, or as a multicolor image utilizing one or several artificial colors to highlight and map important features. Since such a camera simply integrates the optical signal over the spectral range (e.g., 400 nm to 760 nm) of the CCD array, the 'equivalent' monochrome CCD camera image can be computed from the 3D spectral image data base by integrating along the spectral axis, as follows:

$$\text{gray\_scale}(x, y) = \int_{\lambda_2}^{\lambda_1} w(\lambda) \cdot I(x, y, \lambda) d\lambda \quad (2)$$

Figure 3:
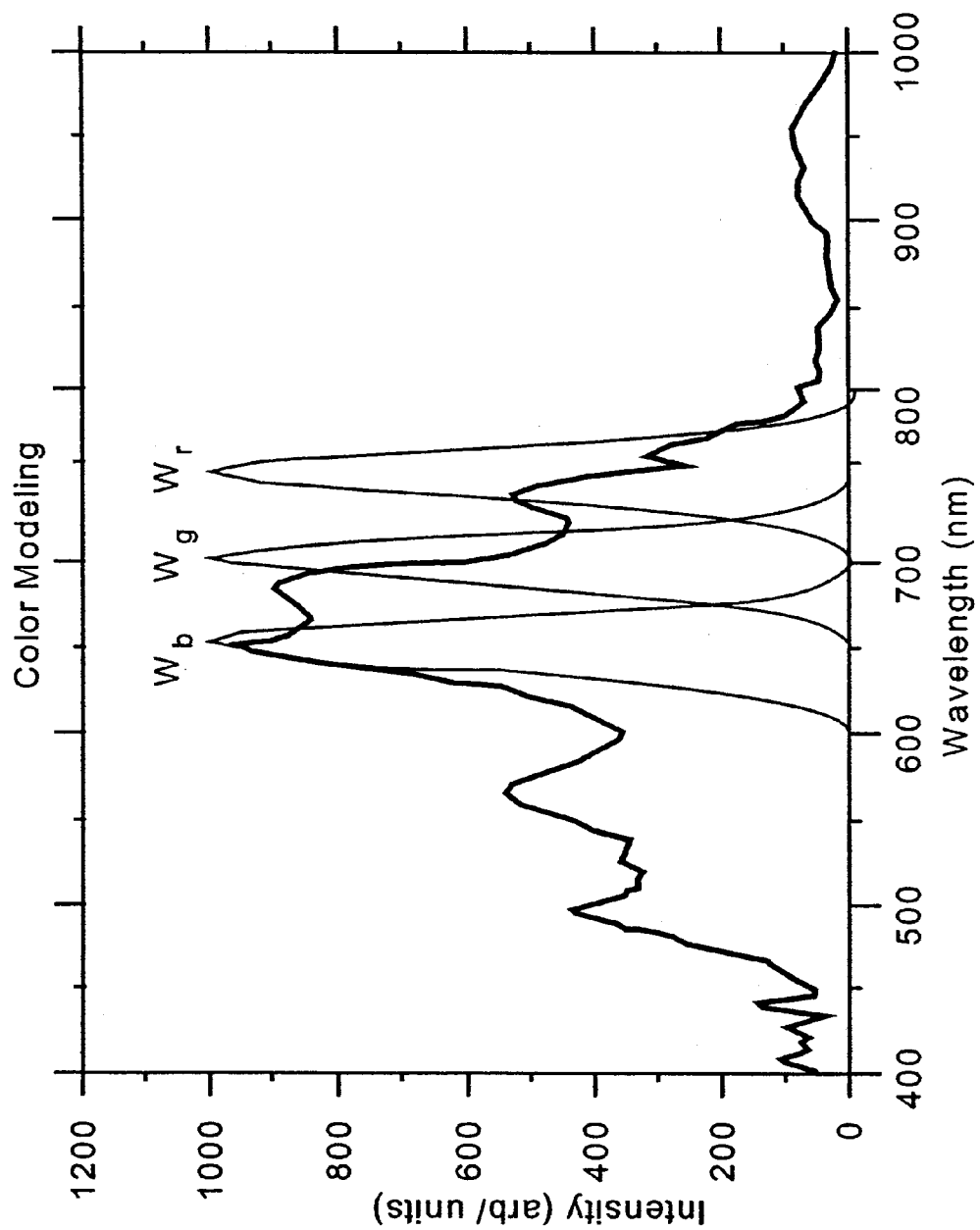
FIG. 3 shows a definition of pseudo-RGB (Red, Green and Blue) colors for emphasizing chosen spectral ranges. The intensity for each pseudo-color is calculated by integrating the area under the curve, after multiplying it by one of the curves.

In equation 2, $w(\lambda)$ is a general weighting response function that provides maximum flexibility in computing a variety of gray scale images, all based on the integration of an appropriately weighted spectral image over some spectral range. For example, by evaluating equation (2) with three different weighting functions, $\{w_r(\lambda), w_g(\lambda), w_b(\lambda)\}$, corresponding to the tristimulus response functions for red (R), green (G) and blue (B), respectively, it is possible to display a conventional RGB color image. It is also possible to display meaningful non-conventional color images, wherein the weighting functions differ from RGB. FIG. 3 presents an example of the power of this simple algorithm. Consider choosing $\{w_r, w_g, w_b\}$ to be Gaussian functions distributed "inside" a spectrum of interest, the resulting pseudo-color image that is displayed in this case emphasizes only data in the spectral regions corresponding to the weighting functions, enabling spectral differences in these three regions to be detected more clearly.

b. Point operations

Point operations are defined as those that are performed on single pixels, (i.e., do not involve more than one pixel at a time). For example, in a gray scale image, a point operation can be one that maps the intensity of each pixel (intensity function) into another intensity according to a predetermined transformation function. A particular case of this type of transformation is the multiplication of the intensity of each pixel by a constant.

The concept of point operations can also be extended to spectral images: here each pixel has its own intensity function (spectrum), i.e., an n-dimensional vector $V_1(\lambda)$; $\lambda \in [\lambda_1, \lambda_n]$. A point operation applied to a spectral image can be defined as one that maps the spectrum of each pixel into a scalar (i.e., an intensity value) according to a transformation function:

$$v_2 = g(V_1(\lambda)); \lambda \in [\lambda_1, \lambda_n] \tag{3}$$

Building a gray scale image according to Equation 3 is an example of this type of point operation. In the more general case, a point operation maps the spectrum (vector) of each pixel into another vector according to a transformation function:

$$V_2(l) = g(V_1(\lambda)); l \in [1, N], \lambda \in [\lambda_1, \lambda_n] \tag{4}$$

where $N \leq n$.

In this case a spectral image is transformed into another spectral image.

One can now extend the definition of point operations to include operations between corresponding pixels of different spectral images. An important example of this type of algorithm is optical density analysis. Optical density is employed to highlight and graphically represent regions of an object being studied spectroscopically with higher dynamic range than the transmission spectrum. The optical density is related to transmission by a logarithmic operation and is therefore always a positive function. The relation between the optical density and the measured spectra is given by Lambert Beer law:

$$OD(\lambda) = -\log_{10} \frac{I(\lambda)}{I_0(\lambda)} = -\log_{10} \tau(\lambda) \tag{5}$$

where $OD(\lambda)$ is the optical density as a function of wavelength, $I(\lambda)$ is the measured spectrum, $I_O(\lambda)$ is a measured reference spectrum, and $\tau(\lambda)$ is the spectral transmitance of the sample. Equation 5 is calculated for every pixel for every wavelength where $I_O(\lambda)$ is selected from (i) a pixel in the same spectral cube for which OD is calculated; (ii) a corresponding pixel in a second cube; and (iii) a spectrum from a library.

Note that the optical density does not depend on either the spectral response of the measuring system or the non-uniformity of the CCD detector. This algorithm is useful to map the relative concentration, and in some cases the absolute concentration of absorbers in a sample, when their absorption coefficients and the sample thickness are known. It should thus be noted that the term "level" as used hereinbelow in the claims section also refers to the terms "amount", "relative amount", "absolute concentration" and "relative concentration".

Additional examples include various linear combination analyses, such as for example: (i) applying a given spectrum to the spectrum of each of the pixels in a spectral image by an arithmetical function such as addition, subtraction, multiplication, division and combinations thereof to yield a new spectral cube, in which the resulting spectrum of each pixel is the sum, difference, product ratio or combination between each spectrum of the first cube and the selected spectrum; and (ii) applying a given scalar to the spectra of each of the pixels of the spectral image by an arithmetical function as described above.

Such linear combinations may be used, for example, for background subtraction in which a spectrum of a pixel or, preferably, the average spectrum of some or all of the pixels located in the background region is subtracted from the spectrum of each of the other (non-background) pixels; and for a calibration procedure in which a spectrum measured prior to sample analysis is used to divide the spectrum of each of the pixels in the spectral image.

Another example includes a ratio image computation and display as a gray level image. This algorithm computes the ratio between the intensities at two different wavelengths for every pixel of the spectral image and paints each of the pixels in a lighter or darker artificial color accordingly. For example, it paints the pixel bright for high ratio, and dark for low ratio (or the opposite), to display distributions of spectrally sensitive materials.

c. Spatial-spectral combined operations

In all of the spectral image analysis methods mentioned above, algorithms are applied solely to the spectral data. The importance of displaying the spectrally processed data as an image is mostly qualitative, providing the user with a useful image. It is also possible, however, depending on the application, to use the available imaging data in even more meaningful ways by applying algorithms that utilize the spatial-spectral correlation that is inherent in a spectral image. Spatial-spectral operations represent the most powerful types of spectral image analysis algorithms. As an example, consider the following situation:

A sample contains k cell types stained with k different fluorophores (the term 'cell' here is used both for a biological cell, and also as 'a region in the field of view of the instrument'). Each fluorophore has a distinct fluorescence emission spectrum and binds to only one of the k cell types. It is important to find the average fluorescence intensity per cell for each one of the k cell types. To achieve this task the following procedure can be used: (i) each pixel in the image is classified as belonging to one of k+1 classes (k cell types plus a background) according to its spectrum; (ii) the image is segmented into the various cell types and the number of cells from each type is counted; and (iii) the fluorescence energy contributed by each class is summed and divided by the total number of cells from the corresponding class.

This procedure makes use of both spectral and spatial data. The relevant spectral data takes the form of characteristic cell spectra (i.e., spectral "signatures"), while the spatial data consists of data about various types of cells (i.e., cell blobs) many of which appear similar to the eye. The ideal type of measurement for this type of situation is a spectral image. In the above situation, cells can be differentiated by their characteristic spectral signature. Hence, a suitable point operation will be performed to generate a synthetic image in which each pixel is assigned one of k+1 values. Assuming that the fluorescence emission spectra of the different cell types are known to be $s_i(\lambda)$; i=1, 2 . . . , k, $\lambda\in[\lambda_1, \lambda_n]$, and the measured spectrum at each pixel (x, y) is $s_{x,y}(\lambda)$, $\lambda\in[\lambda_1, \lambda_n]$, then the following algorithm is a possible method of classification (step 1 above):

Let $e^2_i$ be the deviation of the measured spectrum from the known spectrum of the fluorophore attached to cell type i. Then, adopting a least-squares "distance" definition, one can write:

$$e_i^2 = \sum_{\lambda \in R_\lambda} (s(\lambda) - s_i(\lambda))^2 \qquad (6)$$

where $R_\lambda$ is the spectral region of interest. Each point [pixel (x, y)] in the image can then be classified into one of the k+1 classes using the following criterion:

point(xy) ∈ class k+1 if $e^2 i$>threshold for all i∈[1,k], whereas point(x,y) ∈ class p if $e^2 i$ <threshold, and ρ is such that min[$e^2_i$]= $e^2_\rho$ (7)

Steps ii and iii above (image segmentation and calculation of average fluorescence intensity) are now straightforward using standard computer vision operations on the synthetic image created in accordance with the algorithm described in equations 6 and 7.

Another approach is to express the measured spectrum $S_{x,y}(\lambda)$ at each pixel as a linear combination of the k known fluorescence spectra $s_i(\lambda)$; i=1, 2 . . . , k. In this case one would find the coefficient vector $C=[c_1, c_2, \ldots c_k]$ that solves:

$$F = \min \sum_{\lambda \in R_\lambda} (s(\lambda) - \hat{s}(\lambda))^2 \qquad (8)$$

where $\hat{s}(\lambda) = \sum_{i=1}^{k} c_i \cdot s_i(\lambda)$,

Solving for $$\frac{dF}{dc_i} = 0;$$

for i=1, 2, . . . ,k(i.e., find values of $c_i$ which minimize F) yields the matrix equation $C=A^{-1}B$ (9), where A is a square matrix of dimension k with elements $$a_{m,n} = \left[ \sum_{\lambda \in R_\lambda} s_m(\lambda) \cdot s_n(\lambda) \right], \qquad (10)$$

and B is a vector defined as $$b_m = \left[ \sum_{\lambda \in R_\lambda} s_m(\lambda) \cdot s(\lambda) \right], m, n = 1, 2, \ldots, k. \qquad (11)$$

Arithmetic operations may similarly be applied to two or more spectral cubes and/or spectra of given pixels or from a library. For example consider applying an arithmetic operations between corresponding wavelengths of corresponding pairs of pixels belonging to a first spectral cube of data and a second spectral cube of data to obtain a resulting third spectral cube of data for the purpose of, for example, averaging two spectral cubes of data, time changes follow-up, spectral normalization, etc.

In many cases objects present in a spectral image differ from one another in chemical constituents and/or structure to some degree. Using a principal component analysis by producing covariance or correlation matrices enhances these small differences.

A brief description of the principal component analysis using a covariance matrix is given below. For further details regarding the principal component analysis, the reader is referred to Martens and Naes (1989) Multivariate Calibration, John Wiley & Sons, Great Britain; and to Esbensen et al., Eds. (1994) Multi variance analysis—in practice. Computer-aided modeling as CAMO, and the Unscrambler's User's guide, Trondheim, Norway.

Thus, the intensities of the pixels of the image at wavelength $\lambda_i$(i=1, . . . N) are now considered a vector whose length is equal to the number of pixels q. Since there are N of these vectors, one for every wavelength of the measurement, these vectors can be arranged in a matrix B' with q rows, and N columns:

$$B' = \text{No. of pixels} \begin{array}{c} \text{No. of wavelengths} \\ \begin{pmatrix} B'_{11} & \cdots & B'_{1N} \\ \vdots & & \vdots \\ B'_{q1} & \cdots & B'_{qN} \end{pmatrix} \end{array} \qquad (12)$$

For each of the columns of matrix B' defined is an average:

$$M_i = \frac{1}{q}\sum_{i=1}^{q} B'_{ji}; i = 1 \ldots N \qquad (13)$$

and a second normalized matrix B defined as:

$$B = \text{No. of pixels} \begin{array}{c} \text{No. of wavelengths} \\ \begin{pmatrix} \frac{B'_{11}}{M_1} & \cdots & \frac{B'_{1N}}{M_N} \\ \vdots & & \vdots \\ \frac{B'_{q1}}{M_1} & \cdots & \frac{B'_{qN}}{M_N} \end{pmatrix} \end{array} \qquad (14)$$

A covariance matrix C is defined for the matrix B: $C=B^T \cdot B$ of dimensions N×N. C is diagonalized, and eigenvectors and eigenvalues related by: $C \cdot V_i = \mu_i V_i$ where Vi are N orthogonal unit vectors and $\mu_i$ are the eigenvalues representing the variance in the direction of the i-th unit vector $V_i$. In general, the lowest components represent the highest variability as a function of pixels.

The products $BV_i$ (i=1, . . .N) are the projections of the spectral image onto the elements of the orthogonal basis, and can be displayed separately as black and white images. These images may reveal features not obvious from a regular black and white image filtered at a certain wavelength.

EXAMPLE 3

SPECTRAL IMAGING OF MOVING OBJECTS

According to the present invention provided are spectral images of the eye collected preferably by an interferometer based spectral imager.

Since, in order to perform a measurement, an interferometer based spectral imager must collect several frames of an examined object in a period of time that varies from ca. 5 to 60 seconds, a considerably longer period of time as compared with a camera or video camera snapshot, spectral imaging of moving objects, like the eye results in blurring of the image of the object and in disrupting the algorithm used to calculate the spectrum of each pixel thereof.

Indeed, while using the apparatus disclosed in U.S. Pat. No. 5,539,517 one should ensure that the examined object is substantially stationary for best results.

This is indeed the case in many applications, such as when spectral imaging is used for color karyotyping and color banding of chromosomes as disclosed in Schroeck et al. (1996) Multicolor spectral karyotyping of human chromosomes. Science 273:494–497. However, in other applications spectral imaging of a moving object is required. This is the case for example when the examined object is an organ of a living creature (e.g., a human eye or a specific region or tissue thereof).

Any attempt to measure a spectral image of a living organ, which organ is not motionless, will result in artifacts and a distorted or particularly noisy spectral image data. If such an image is acquired using filter or grating based spectral imagers, a spatial image registration procedure will be required for best results. Nevertheless, these spectral imagers suffer limitations as described in the background section and are therefore less preferred.

On the other hand, should such an image be acquired by an interferometer based spectral imager which have numerous advantages over other spectral imaging systems, not only spatial registration but also spectral correction is required.

PCT/US97/08153, filed May 12, 1997, which is incorporated by reference as if fully set forth herein, teaches spatial registration and spectral correction for interferometer based spectral imaging.

U.S. Pat. No. 5,539,517 and other publications [e.g., (i) Schroeck et al. (1996) Multicolor spectral karyotyping of human chromosomes. Science 273:494–497; (ii) Malik et al. (1996) Fourier transform multipixel spectroscopy for quantitative cytology. J. of Microscopy 182:133–140; (iii) Malik and Dishi (1995) ALA mediated PDT of melanoma tumors: light-sensitizer interactions determined by a novel spectral imaging system. Proceedings of optical methods for tumor treatment and detection: Mechanisms and techniques in photodynamic therapy IV, Feb. 4–5, 1995, San Jose, Ca., SPIE Vol. 2392, pp. 152–158; (iii) Malik et al. (1994) A novel spectral imaging system combining spectroscopy with imaging—application for biology. Proceedings of optical and imaging techniques in biomedicine, Sep. 8–9, 1994, Lille, France, SPIE Vol. 2329, pp. 180–184; (iv) Malik et al. (1996) Fourier transform multiplex spectroscopy and spectral imaging of photoporphyrin in single melanoma cells. Photochemistry and photobiology 63:608–614; and (v) Soenksen et al. (1996) Use of novel bio-imaging system as an imaging oximeter in intact rat brain. Proceedings of advances in laser and light spectroscopy to diagnose cancer and other diseases III, Jan. 29–30, 1996, San Jose Ca., SPIE Vol. 2679, pp. 182–189] teach spectral imaging devices and methods, in which the light from a surface of an examined object is collected by an optical aperture or field lens, passed through an interferometer, in which it is split into two coherent rays, and then it is focused by focusing optics onto a two-dimensional detector array device (e.g. a CCD in the UV to visible range) having a surface of detector elements, such that the detector's surface represents a real image of the object's surface.

The signals from each and all detector elements of the detector array, as obtained from many successive frames of the detector array, are recorded, while the interferometer is scanned in synchronization with the detector frames.

Since at each position of the interferometer, the optical path difference (OPD) between the two split beams through which a detector element sees its corresponding picture element (pixel) varies in a known way, at the end of the scan, the signals collected for each pixel form a function called interferogram, which is the intensity of light as function of the optical path difference (OPD) for that particular pixel. Because the interferometer speed is constant, the CCD frame time is constant and the OPD is proportional to the interferometer angular position, the OPD samples are equally spaced.

According to the well known teachings of the Fourier transform spectroscopy, the mathematical Fourier transform operation applied to this interferogram function yields a spectrum, i.e., the intensity of light in every wavelength emitted by the pixel in question.

Since interferogram functions are known for every pixel of the object's surface, spectra can be calculated and known for every pixel thereof, by applying the Fourier transformation to all of the interferograms thus collected.

U.S. Pat. No. 5,539,517 teach several embodiments of spectral imaging devices and methods, each is capable of measuring a spectral image of an object, which devices differ from one another in the type of interferometer used therein.

It is well known that, in general, no matter what interferometer is used, at any one position of the interferometer scan, the OPD is different for an on-axis and an off-axis ray, and as a consequence, the OPD differs from pixel to pixel in the same frame.

For example, as explained in "The principles of interferometric spectroscopy" by John Chamberlain, John Wiley & Sons, 1979, page 217, Equations 8.1a and 8.1b, in a Michelson interferometer the OPD varies according to the following Equation:

$$OPD_\alpha = OPD \times \cos\alpha \qquad (15)$$

where $\alpha$ is the angle between the on-axis and the off-axis rays.

According to Equation 15, the OPD dependence on the specific pixel is relatively low. In fact, in Equation 15, $\alpha$ is a small angle, and therefore the term ($\cos\alpha$) varies slowly as $\alpha^2$.

However, in a triangular interferometer such as that shown in FIG. 2, the OPD varies faster, i.e., linearly with the projection of the angle of incidence of the ray in the horizontal direction (equivalent to the projection of the distance of the corresponding pixel from the center of the image in the horizontal direction) as shown in Equation 31 in column 13 of U.S. Pat. No. 5,539,517.

This fact has two important consequences for an interferometer based spectral imager:

First, one has to keep track of the OPD for every pixel and every detector frame, so that at the end of the scan, it is possible to reconstruct the spectrum through the Fourier Transform algorithm. This is done by knowing (i) the interferometer position for every frame and (ii) the pixel position in the image.

Second, should the examined object move during the measurement, the spatial registration of the various frames is lost, and the actual OPD of each pixel in each frame is different than it would have been should the object be still. Thus, if a spectral image of that object is calculated while neglecting its movements during the measurement, and the object is displayed using the collected data, for example via a Red-Green-Blue (RGB) function defined over some or all the spectral range, then (i) the image will look blurred due to loss of spatial registration during the measurement, and (ii) the calculated spectra will not represent the actual spectra, these spectra will look very noisy and not consistent due to the use of incorrect (i.e., non-registered) OPDs in the Fourier transformation.

Before turning to the description of the method for spatial registration and spectral correction for interferometer based spectral imaging which can be used to obtain spectral images of moving objects, the prior art method for measurement of a stationary object will be described.

Thus, a measurement of a stationary objects include the following steps.

First, the spectral imaging device is aligned and focused with respect to the examined object.

Second, the interferometer is scanned in equally spaced OPD steps, while acquiring and storing successive frames of the object by the CCD.

Third, the data is ordered (e.g., by a software) into an interferogram function for every pixel of the object's image.

Fourth, preferably some well known preprocessing steps called windowing or apodization (see, Chamberlain (1979) The principles of interferometric spectroscopy, John Wiley and Sons, pp. 131 and following pages) are performed, in order to regularize the data such that the data of the measurement, which is a discrete and finite set of data, can be used instead of a theoretical continuous interferogram function.

Fifth, "zero filling" procedure is typically performed, such that the number of data for each interferogram is completed to a number of points which equals a power of two of the original number of data, in order to fill-in the spectrum with more interpolated points and to use fast Fourier transform algorithms (see, Chamberlain (1979) The principles of interferometric spectroscopy, John Wiley and Sons, pp. 311 and following pages).

Sixth, the complex (real and imaginary parts) Fourier transforms are calculated by applying the fast Fourier transform algorithm on each of the interferograms. Alternatively, yet less preferably, a straight Fourier transform algorithm is applied. In the latter case "zero filling" is not required.

Seventh, the spectrum of every pixel is calculated as the module (length) of the complex function so obtained, a function defined on discrete values of a conjugate parameter to the OPD, the wavenumber $\rho$, which in turn is the reciprocal of the wavelength: $\sigma = 1/\lambda$.

The fast Fourier transform algorithm reduces very considerably the calculation time but it can be used only when the OPD's are equally spaced and when the number of points in which the interferogram is defined equals to a power of two. For this reason the straightforward Fourier transform algorithm is generally not used.

The method for spatial registration and spectral correction for interferometer based spectral imaging which can be used to obtain spectral images of moving objects is described hereinafter.

The following description concerns an object that moves rigidly and linearly on a plane substantially perpendicular to the line of sight of the imager in a random or non-random movement. In other words the object moves in such a way that all of its parts keep their shape and size, and their relative distances, as seen through the spectral imager.

Thus, in the case of a rigidly moving object in random directions without changing plane, (i.e., without getting closer or farther from the instrument, so that the object remains in focus), the measurement steps according to the method of the present invention are as follows.

First, the spectral imaging device is aligned and focused with respect to the examined object.

Second, the interferometer is scanned in synchronization with the CCD frames and constant speed, while acquiring and storing successive frames of the object by the CCD. However, contrary to the above prior art description, due to the object's movements, the resulting OPD steps are inherently not equally spaced as described above. The difference between successive OPD's is now random: it is the result of the combined motion of the interferometer and of the object, it can increase or decrease depending on the instantaneous position and velocity of the object with respect to the position and velocity of the interferometer, it can even be negative (meaning decreasing OPD from a data point to the next) and, if the movement is larger than the field of view, or the movement is a sudden displacement larger than the field of view with immediate return to the previous position, a data point can be missing altogether. In some regions of the OPD axes the data points will be dense, in others they will be sparse.

Third, the data is ordered (e.g., by a software) into an interferogram function for every pixel of the image. However, now the book-keeping is more complicated. In order to accomplish this step one must first find the spatial translation vector of all the frames measured, with respect to a frame taken as reference. This way the actual OPD for every pixel in each frame can be found. Since this is a crucial step of the method according to the present invention it is described in more detail hereinbelow.

Fourth, preferably some well known preprocessing steps called windowing or apodization are performed, in order to regularize the data such that the data of the measurement which is a discrete data can be used instead of a theoretical continuous interferogram function.

Fifth, here the method splits into two alternative branches. According to the first, the measured interferogram of each pixel is not further interpolated and will be used with a straightforward Fourier transform algorithm to calculate its corresponding Fourier transform, whereas, according to the second, the measured interferogram of each pixel is interpolated to achieve OPD values which are equally spaced, and will be used with a fast Fourier transform algorithm to calculate its Fourier transform. Each alternative has advantages and disadvantages. Speed is higher in the latter but, as interpolation introduces errors, reliability of the data is higher in the former.

Sixth, a complex (real and imaginary) Fourier transform for each pixel is calculated by applying the straightforward or fast Fourier transform algorithms to each of the interferograms, depending on alternative choice made under the fifth step above.

Seventh, the spectrum of every pixel is calculated as the module (length) of the complex function so obtained, a function defined on discrete values of the conjugate parameter to the OPD, the wavenumber a.

For further details about the theory of Fourier transformation and the mathematical steps for computing the mathematical spectrum as an approximation to the real physical spectrum, starting from the measured interferogram, the reader is referred to textbooks such as Chamberlain (1979) The principles of interferometric spectroscopy, John Wiley and Sons, which is incorporated by reference as if fully set forth herein.

In some highlights of chapters 2, 4, 5 and 6 of Chamberlain (1979) the following basics of the Fourier transform manipulation and relevant considerations are described. The Fourier integral relation between a function f(k) and its Fourier transform F(x) is shown on page 31. In principle, f(k) and F(x) are continuous functions of their variable, but in practice they are always known for discrete values, so that the Fourier integral is approximated by an infinite sum as shown on page 55. The infinite sum is in turn substituted with a finite sum as shown on page 57. The perfect and practical interference functions in the case of electromagnetic radiation are derived as shown on pages 96 and 104. The relation between the physical spectrum and the mathematical spectrum is shown on page 127, and the theory of sampling and correction of phase errors are shown in sections 6.7 to 6.11. Finally, the Fast Fourier Transform algorithm is detailed in chapter 10, and is shown to operate only when the discrete intervals are all equal, yet this operation is faster than the straight Fourier summation.

It will be appreciated by one ordinarily skilled in the art that the third step of the method described hereinabove can be accomplished in many alternative ways. One of these alternatives is as follows.

First, one of the frames is defined as a reference frame. In principle it is not important which frame is selected as the reference. In practice, however, it is better to select a frame which is roughly centered with respect to the set of translation vectors, so that the overall spatial overlap between the selected frame and all the other frames is maximized. Thus selecting the reference frame assists in finding the translation vectors for each of the frames measured.

Second, a subtraction image which is the difference in intensity between a first frame and the reference frame is displayed.

Third, the first frame is moved in small steps to the right-left and up-down directions while always displaying the intensity difference, until a position in which the displayed subtraction image is substantially zero everywhere, or has substantially no features, is found. In the ideal case, in which the movement is completely rigid, the subtraction image equals zero at all pixels of overlap. In practice, however, there will always be a slight pattern, and then the best position is the one in which this pattern is minimized in intensity. Experience proved that it is quite easy to find the substantially zero position by eye, because a slight lack of spatial registration emphasizes the differences between two frames, which are therefore easy to detect. This procedure can be automated using various known algorithms, see for example Anil K. Jain (1989) Fundamentals of digital image processing. Prentice-Hall International and system sciences science, pp. 400–402. However, due to the presence of fringes superimposed on the frames, it is preferred that a fringe suppression algorithm is employed prior to automatic spatial registration of the frames.

Fourth, the translation vector for the first frame is recorded.

Fifth, the procedure is repeated for all additional frames of the measurement.

And finally, knowing the OPD dependence on position (it is a specific dependence for every interferometer), the OPD vector for every pixel in every frame is calculated and stored.

Problems which may arise during measurement and which affect the final results are mostly associated with the amplitude of the object's movement. For the method to be useful, the amplitude of the movement is preferably not too large. In particular, a number of possible problems may arise.

First, entire regions of the interferogram maybe missing, making it very difficult to interpolate (in the case of interpolation).

Second, if the central portion of the interferogram is completely missing, the Fourier transform cannot be calculated.

And finally, if due to the movement of the examined object the actual OPD steps (after correction for the movement) are larger than the Nyquist condition (one half the lowest wavelength of sensitivity of the instrument), spurious results may be introduced.

Nevertheless, corrective actions may be undertaken, some of which are listed hereinbelow.

First, in a case where the central portion is present, it is usually easy to find the center of the interferogram. In this case, if the interferogram is symmetric, data points on one side of it can be reflected to the other side, filling holes in the process.

Second, take the smallest OPD steps compatible with the needed spectral resolution and measurement time. This again will have the tendency of not allowing large holes in the interferogram.

Third, repeat the interferometer scan two or three times and then join the data as if measured in one measurement. Thus, if an OPD is missing in one of the scans, chances are (for random movement) that it will not be missing in another.

Fourth, in an interferometer in which the OPD in a frame varies in one direction only (e.g., horizontal), and if the movement of the object is in one direction only (e.g., the human eye displays preferentially involuntary horizontal movements), make sure the instrument is rotated around the optical axis, so that the OPD gradient is perpendicular to the direction of the object movements. This way the movements affect only the spatial registration of the frames and the interferograms stay almost unaffected, reducing significantly one source for errors.

Fifth, in the case of a featureless object, it is expected that a movement will not affect the results significantly, since all pixels are equivalent in any case.

And finally, the following distinctions should be made: (i) an object that moves rigidly and linearly on a plane, i.e., the object moves such that all of its parts keep their shape and size, and their relative distances remain constant as seen through the spectral imager, and (ii) an object that moves linearly on a plane, such that all of its parts keep their shape and size, but the relative distances of the parts may vary in time. Obviously, the former case is simpler than the latter. In addition, once an acceptable solution is found for the former, the latter can in general be solved by segmenting the object into individual areas which may move with respect to one another, although each one separately moves rigidly, and then applying to the individual areas the solution of the former case.

It should be noted that the considerations described hereinabove are valid for certain type of movements, in particular rigid linear movements (both random or not). However, it will be evident that some of the considerations described hereinabove can be generalized to other types of movements, e.g., non-rigid and/or non-linear movements. In any case, a rotation of the object around an axis which is perpendicular to the line of sight of the instrument cannot be addressed in principle, because parts of the object will change shape and disappear from view during the measurement, and obviously then the measurement will be incomplete.

As is appreciated by one ordinarily skilled in the art, solving the problem of the moving object is equivalent to calculating the Fourier transform of an interferogram defined for values which are inherently not equally spaced. This problem is known in radio astronomy (see, Synthesis Imaging (1986) Perley, Schwab and Bridle, Report of Summer School of the National Radio Astronomy Observatory, p. 72, Greenbank W. Virginia), where there is clumping of data in the low OPD range, and this introduces large undulations in image intensity which make it difficult to detect weak point sources.

Obviously, in the cases of a living tissue, it is generally difficult, if not impossible, to keep the analyzed tissue completely motionless. This is due to respiration, heart beat, involuntary movements of the patient, etc. Even when the tissue itself is forced to be stationary by external mechanical means (for example special holders to keep an eye stationary during corneal surgery), the mere fact that blood is circulating in the vessels induces a small movement in the examined tissue. In this case, especially when the object is magnified through a microscope, the movement of the analyzed area is also magnified.

An interferometer based spectral imager as taught in U.S. Pat. No. 5,539,517, combined with the described for spatial registration and spectral correction, or in other words compensating both spatially and spectrally for movements of the examined object, based on the spectral information that it provides, not only may enable noninvasive evaluation of the oxygen saturation level of hemoglobin in retinal blood vessels and hemoglobin concentration thereat, but also, because of the imaging information that it provides, it may be used for the detection and mapping of retinal ischemia. Joined to advanced spectral analysis algorithms such as but not limited to principal component or neural network algorithms, it may also prove useful for classification of the different retinopathy stages, and treatment categorization of for example diabetic patients.

Many chemicals in the living tissue are related to the functioning of the vessels and to metabolism. Therefore, even though the primary element for retinal ischemia is oxygen, which can be measured through the concentration of hemoglobin in the oxy- and deoxy forms, important information can be obtained also by measuring the concentration of other constituents, such as $NAD^+$, NADH, flavin, cytochromes, oxidases, reductases, etc.

Considering the large amount of prior art that has been described for spectral detection of such chemical constituents of tissue, correlating the absorption peaks in reflectance, and the fluorescence peaks in UV or blue light, single or multiple wavelengths excitation, to their concentrations, it is conceived that an interferometer based spectral imager as taught by U.S. Pat. No. 5,539,517, combined with the described method may be used to map concentrations of one or more of such constituents simultaneously in living non-motionless organs/tissues. The particular hardware configuration in which the imager will be operated, will dictate the type and amount of information obtained.

For example, the simplest and most straightforward configuration is when the imager is attached to the CCD port of a fundus camera, so that the retina is imaged, and the same wide band white light source of the fundus camera is used to measure the reflected light from the retina. In this case oxygen concentrations can be measured using Delori's algorithm [Delori (1995) Appl. Optics 27:1113–1188, and Appl Optics, Vol. 28, 1061; and, Delori et al. (1980) Vision Research 20:1099], or similar, extended to all pixels of the imaged retina. More complicated systems based on interferometer based spectral imagers are: (i) auto-fluorescence spectral imaging; (ii) spectral imaging using UV or blue light fluorescence excitation; (iii) spectral imaging using laser excited fluorescence, singly, simultaneously, or in succession, at the following wavelengths: 650, 442, 378, 337, 325, 400, 448, 308, 378, 370, 355, or any other equivalent wavelengths which give similar information.

These configurations can be built in several ways, either separately or combined in any number of combinations in the same instrument: the instrument is made of the light source(s), the fundus camera and the spectral imager, including a computer and software to interpret the data and display it in a useful way for the ophthalmologist.

In all cases of white light reflection, auto-fluorescence, single wavelength continuous wave laser excitation fluorescence, or multiple wavelength laser excitation fluorescence, the sample is illuminated and a spectral image is measured.

In the case of pulsed laser illumination, the method of work of the spectral imager is slightly modified and requires some hardware changes which are not basic and substantial, but important for the instrument to operate. These changes are the following.

For single pulsed laser excited fluorescence spectral imaging, the laser pulses and the frame grabbing of the CCD of the imager are synchronized with the scanning angle of the interferometer, so that at each pulse the interferometer performs a step, and a new frame is collected by the computer (several pulses can also be used in general for each frame, as long as this number does not change from frame to frame). In this way, at each OPD value, the interferogram value corresponds to the same number of pulses of the laser. This is necessary to ensure that each frame is taken with the same total illumination intensity, otherwise, each frame measures the fluorescence resulting from a different number of laser pulses and the interferogram will be distorted.

For several pulsed lasers induced fluorescence spectral imaging, the method of work can be in two ways: (i) collect a whole spectral cube for each laser separately as above, in succession; this means that during a measurement only one laser is activated, and at the end there is one spectral cube measured for each laser wavelength; and, (ii) pulse each laser in succession in synchronization with the interferometer and the frame grabbing, so that all the lasers are switched in succession before the next step of the interferometer and the next frame is taken; in this case, at the end, only one spectral cube is measured.

All the information must be analyzed and interpreted. The most important algorithms are going to be of a type that compares the resulting intensities between different wavelengths and between different pixels of the image. These algorithms should consider variations of intensities, and ratios between different regions in the tissue and between different wavelengths. The method will be very sensitive, and may replace slit lamp imaging (white light or filtered light), because it will provide a large quantitative information.

Other applications will be apparent to one ordinarily skilled in the art. These include visual loss due to choroidal ischemia, acute sectorial choroidal ischemia, ischemic optic neuropathy, corneal and iris problems, etc., and many others which are analyzed today by imaging techniques, either using white light or fluorescence of different origins.

Since the spectral imagers according to U.S. Pat. No. 5,539,517 can be attached to any imaging optics including endoscopes and laparoscopes, it may be used as an aid to the surgeon before, during or after surgery to accurately define the diseased tissue to be removed, to aid in the decision where to start cutting, where to stop, and to judge whether all diseased tissue has been removed during an operation procedure. These spectral imagers are intrinsically suitable to analyze the nature of the tissue through the chemical composition, related in turn to its spectral characteristics, and to provide a visual map (usually enhanced), for a user to grasp, take decisions and act.

In the case of cancerous tissues detection in vivo, both the hardware configurations and the types of analysis and display algorithms involved are very similar to the above described ophthalmologic examples. The differences are in the collecting optics (endoscopes of different types instead of for example a fundus camera), in the types of some basic molecular components involved in the detection: some of these are probably common, such as oxygen concentration, additional others are collagen and elastin, genetic material in the cell nuclei, such as DNA chromatin, etc. The illumination and synchronization requirements in the case of multiple wavelengths or pulsed excitation are similar as well [Pitris et al., Paper presented at European Biomedical Optics Week by SPIE, 12–16 September 1995, Barcelona Spain].

In all these examples spatial registration and spectral correction are required and are provided by the described method.

The power of the spatial registration and of the spectral correction method is further described and exemplified hereinbelow.

Figure 4A:
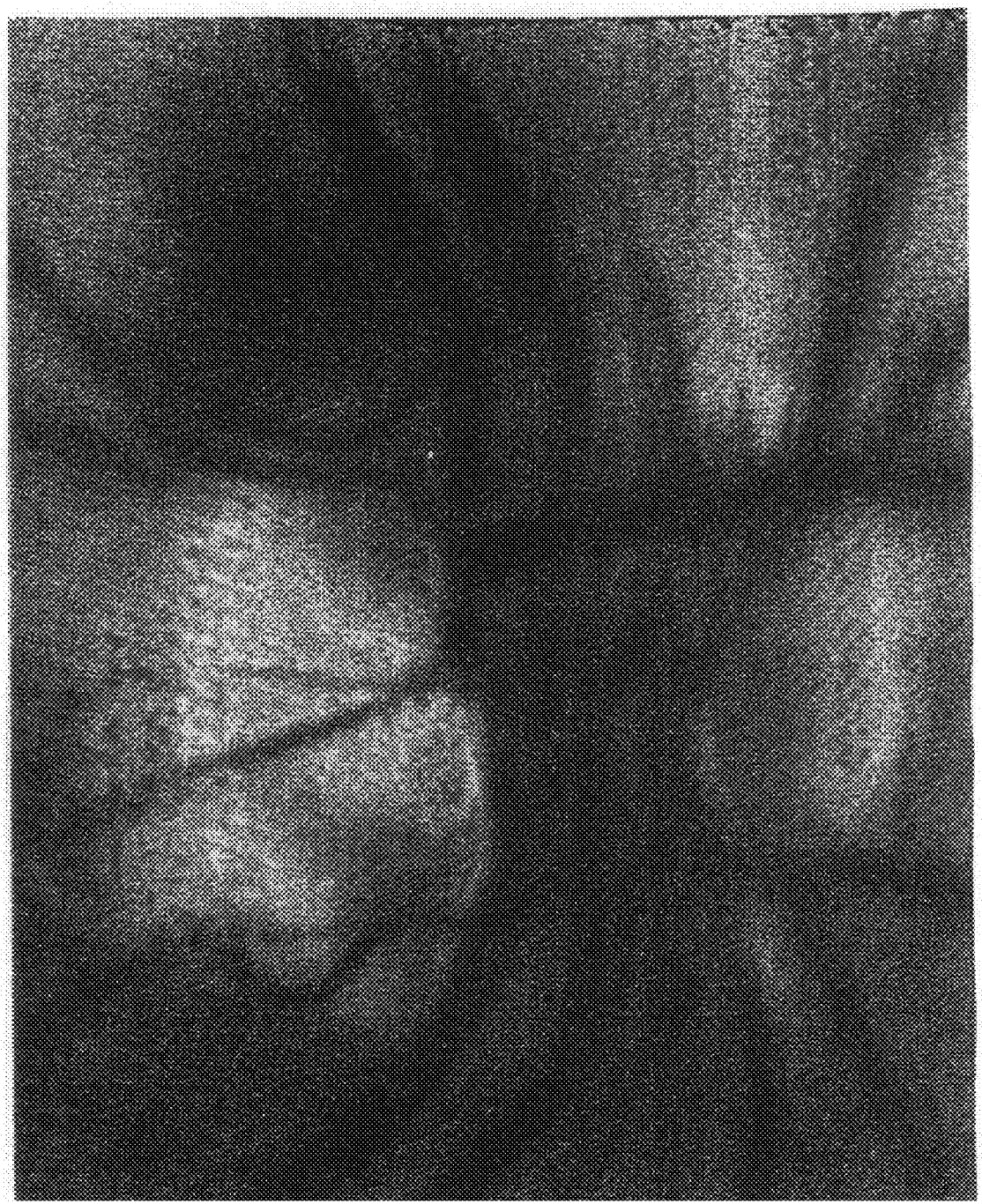
FIG. 4a is a spectral image of a human right eye acquired using the SPECTRACUBE system.
Figure 4B:
FIG. 4b is a spectral image of the human right eye of FIG. 4a after spatial registration and spectral correction.

Spatial Registration and Spectral Correction—the effect on the image: FIG. 4a presents a spectral image of the optic disk of the retina of a right eye of a healthy individual using the SPECTRACUBE system, while not employing spatial registration and spectral correction procedures as described in accordance with the method of the present invention. FIG. 4b, on the other hand, presents the very same image after spatial registration and spectral correction procedures according to the present invention.

In both images the optic disk appears lighter in the middle portion of the image along with blood vessels nourishing the optical nerve with oxygen and other nutrients (arterioles) and removing waste and carbon dioxide generated during metabolism (veins). However, as is clearly evident comparing the two images, due to movements of the eye during measurement, the image of FIG. 4a is highly is blurred. Corrective action according to the method of the present invention, in which spatial registration and spectral correction were applied, resulted in a much clearer image as shown in FIG. 4b.

Furthermore, the images presented in FIGS. 4a and 4b show not only the spatial organization of the tissue, as they also present spectral information, although not in a direct fashion. In other words, the different colors present in the images result from the application of an RGB algorithm to the spectrum of each pixel of the image such that each pixel, according to its spectrum and according to the preselected RGB function is presented by RGB colors in corresponding intensities. It is clear that as a result of the distorted spectra associated with pixels of the image shown in FIG. 4a, as is further demonstrated hereinbelow, the RGB function yields different results when applied to either image.

This Example emphasizes the importance of spatial registration and spectral correction to obtain clear and informative image of the examined moving object, the eye in the present case.

The following examples demonstrate specifically the importance of spectral correction to obtain meaningful spectral information from selected regions of the examined object, which information may be employed to achieve information about the metabolic condition of an examined tissue, etc.

Figure 5A:
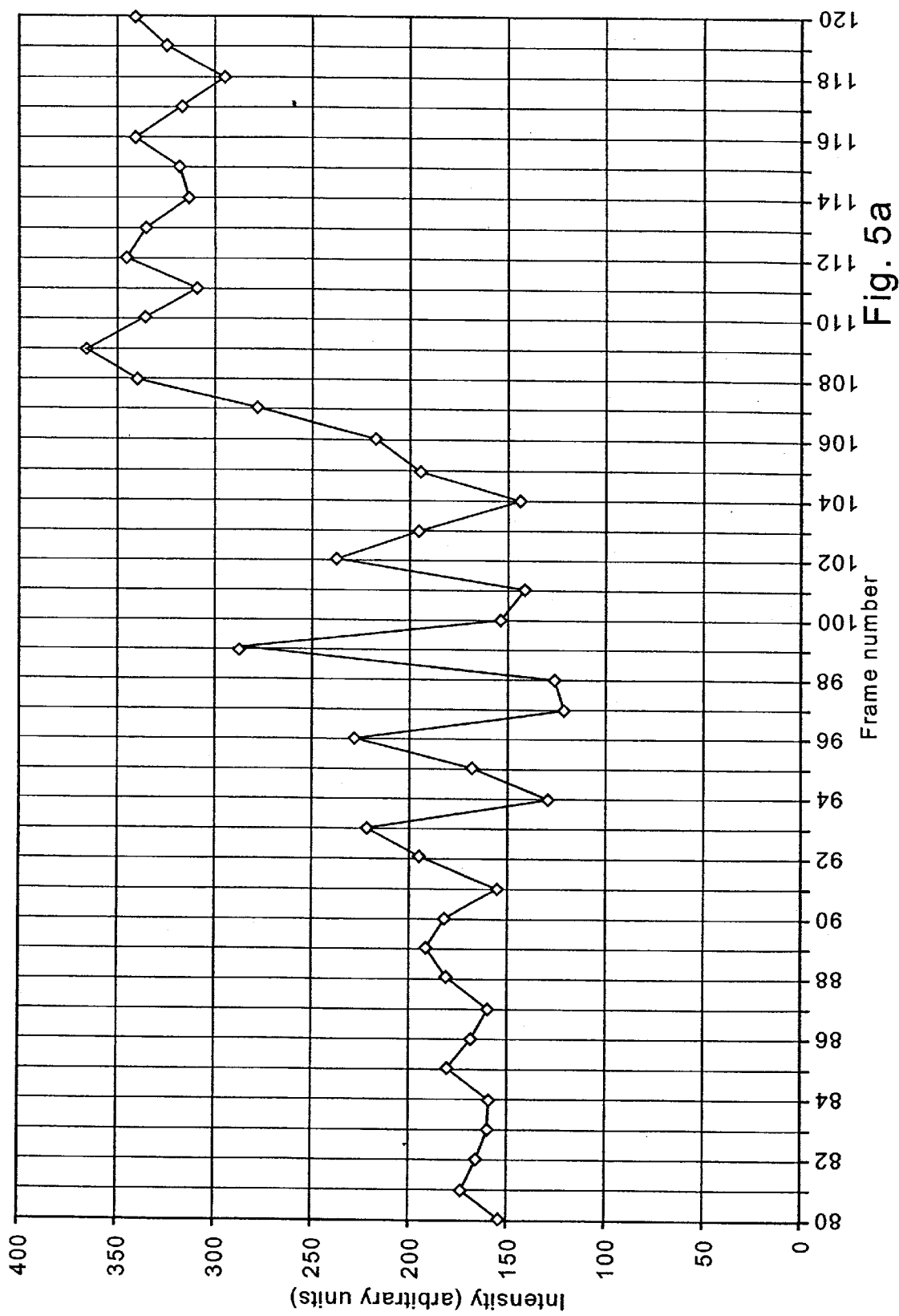

Spectral Correction—the effect on the interferogram: FIG. 5a presents a portion of an interferogram calculated for a single pixel (x=112, y=151) of the image presented in FIG. 4a, i.e., while not employing spatial registration and spectral correction procedures as described in accordance with the method of the present invention. FIG. 4b, on the other hand, presents the corresponding portion of an interferogram of the very same pixel after spatial registration and spectral correction procedures according to the present invention.

Examining the interferogram of FIG. 4a reveals that the left and central parts of the function (measured in equal intervals of time) resembles a typical interferogram, whereas the right portion of the function, is totally atypical. The local maximum indicated by an arrow is due to sudden motion of the examined object (e.g., a saccadic motion of the eye). The uncharacteristic increase of signal is due to the fact that a different point in the object being measured suddenly appeared not in its original place, giving a different value for the interferogram function, as compared with a situation wherein the object remains stationary.

Figure 5B:
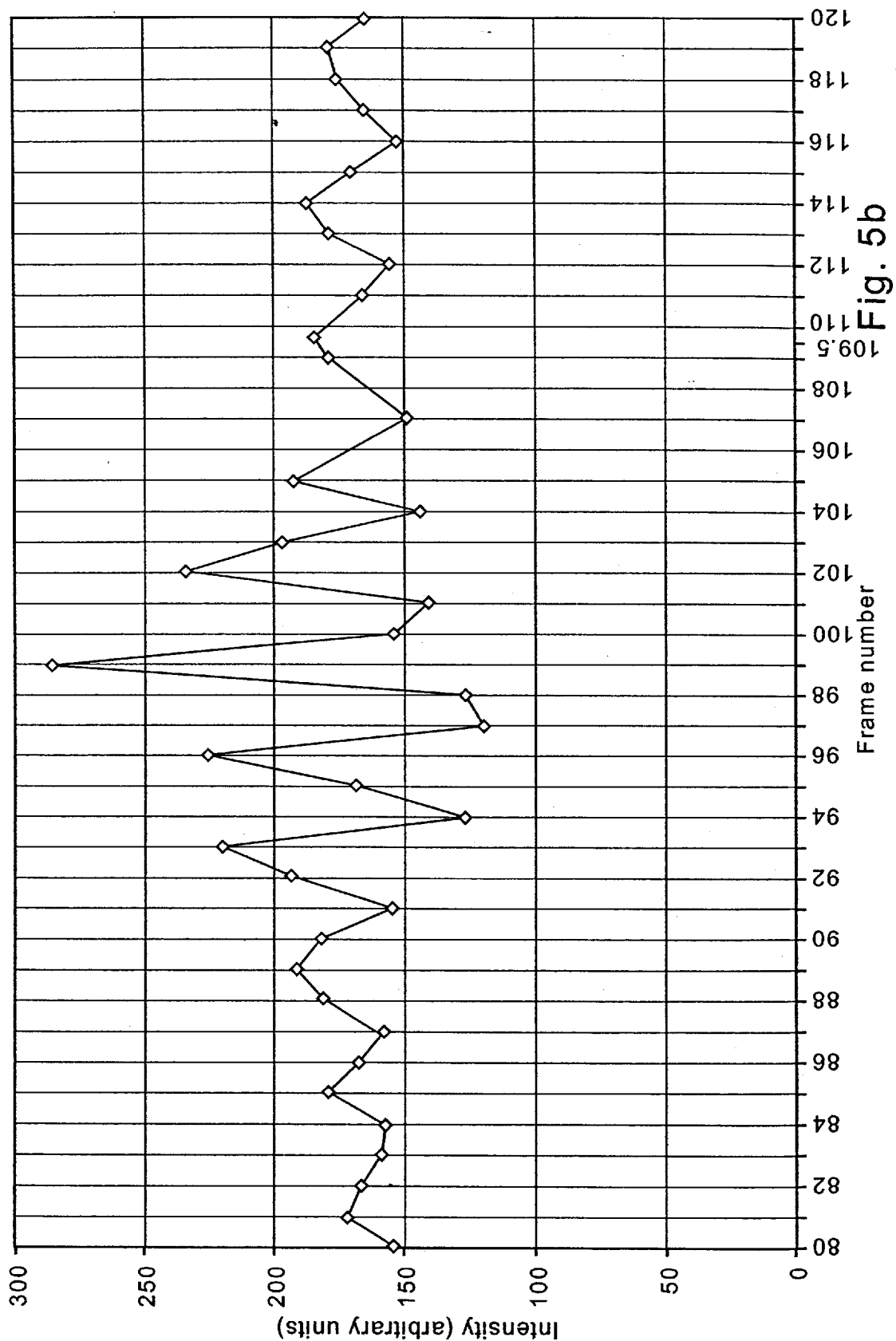
FIG. 5b presents a portion of an interferogram function of the same pixel of FIG. 5a, which pixel is derived from the spectral image of FIG. 4b.

Nevertheless after spatial registration and spectral correction procedures according to the present invention are applied, as shown in FIG. 5b, the interferogram function of the same pixel appears typical.

As can be seen in FIG. 5b, the corrected interferogram is well behaved. It does not have spurious discontinuities or uncharacteristic portions characterizing the non-corrected interferogram of FIG. 5a.

However, the corrected interferogram of FIG. 5b is now defined in nonuniform intervals. For example one notices that around frame number 107 the density of data is low, meaning that the eye moved in a direction opposite to the scanning direction of the interferometer, increasing the OPD intervals around it, whereas around frame number 109.5, which is an artificial frame number formed due to the magnitude of movement of the eye in the same direction as the scanning direction of the interferometer, the density of data is higher, decreasing the OPD intervals around it.

There are therefore, several routes by which one can perform the Fourier integral to approximate the physical spectrum of the specific pixel. According to one route one can interpolate between the given OPD values and then define a new interferogram having equally spaced OPD values, thus allowing use of a fast Fourier transform algorithm to approximate the physical spectrum of that pixel. According to another route, one can calculate the Fourier integral as the sum of the interferogram values weighted according to their own intervals using Equation (16):

$$f(\sigma)=1/K \cdot \Sigma F(x_i) \Delta_i e(i\sigma x_i) \tag{16}$$

where K is a constant, f(σ) is the value of the spectrum at wavelength λ=1/σ, and $\Delta_i$ is the difference between the OPD at $x_i$ and the OPD at $x_{i+}$1. It will be apparent to one ordinarily skilled in the art, that there may be additional ways to approximate the physical spectrum, such as methods as described in Synthesis Imaging (1986) Perley, Schwab and Bridle, Report of Summer School of the National Radio Astronomy Observatory, p. 72, Greenbank W. Va.

Spectral Correction—the effect on the spectrum: FIG. 6a presents spectra of five adjacent pixels derived from the image of FIG. 4a, while not employing spatial registration and spectral correction procedures as described in accordance with the method of the present invention. Four of these pixels are centered around the fifth which is the pixel whose interferogram is shown in FIG. 5a. FIG. 6b, on the other hand, presents spectra of the same five pixels after application of the spatial registration and spectral correction procedures according to the present invention. The dip around 575 nm is characteristic of oxyhemoglobin absorption.

Comparing the spectra of FIGS. 6a and 6b, one notices two phenomena. First, corresponding spectra are much noisier in FIG. 6a as compared with FIG. 6b. Second, when implementing the method of the present invention, as shown in FIG. 6b, from pixel to pixel the spectra change in a uniform pattern presenting an expected smooth behavior over the entire spectral range, whereas none such behavior can be seen in the spectra of FIG. 6a.

Thus, these examples emphasize the importance of spectral correction to obtain meaningful interferograms and spectra derived from an examined moving object.

Spatial registration of Frames assisted by Fringe suppression: The raw data of a randomly moving object as measured by an interferometric spectral imager, should be preprocessed before the Fourier Transform is calculated on the pixels interferograms to obtain the best final spectral cube.

This is due to the fact that in a spectral imager based on a Sagnac or similar type interferometer as herein described, the instantaneous Optical Path Difference (OPD) corresponding to an interferogram data point depends not only on the specific CCD frame but also on the specific pixel to which that data point refers.

As a result, if the object moves during the measurement, the pixel occupied by a point on the object is different than if the object is stationary, and if no correction is used, the Fourier Transform algorithm uses the wrong OPD for that data point. The resultant spectral image cube can be significantly corrected if by some means the algorithm is made to use the appropriate OPD for each data point instead of the inappropriate one. Finding the appropriate OPD for each interferogram data point requires (i) spatial registration of each acquired frame and recording of its registration vector; and (ii) calculation of the actual OPD for each data point, based on the registration vectors and on the OPD dependence on position.

Figure 7A:
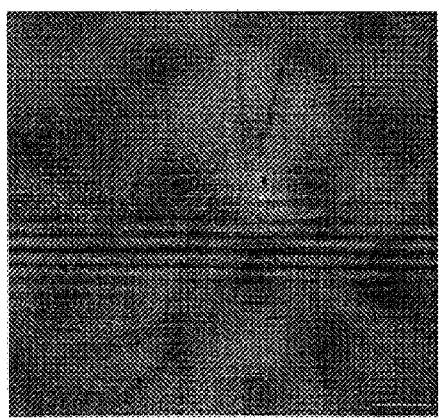
FIGS. 7a–f present the operation of a fringes suppression algorithm.

However, there is one physical phenomenon, the appearance of fringes, which makes the frame registration more difficult, yet not impossible, when performing this registration automatically. As shown in FIG. 7a, fringes are straight line stripes of intensity modulation superimposed on the frame, which slightly change position, with respect to the frame on which they appear, depending on the scanning position of the interferometer. The origin of the stripes is due to constructive (light stripes) and destructive (dark stripes) interference of the light rays while passing through the interferometer, and their shape (vertical or horizontal straight lines, depending on optical alignment) is due to the fact that all the pixels on a vertical line (or horizontal, respectively) go through the same OPD for every scanned frame, so that they undergo the same amount of interference (for the same wavelength of light). The change in position from frame to frame is due to the fact that the constructive or destructive level of interference for a certain pixel changes according to the interferometer position while scanning. The stripes are not very bothersome when registering the scanned frames by eye one on top of the other, because despite the fringes, the other features (e.g., patterns of blood vessels in the eye) are well visible in each frame, and the appearance of the stripes does not prevent an observer, when superimposing one frame over the other, from deciding the best spatial registration.

However, when using an automatic algorithm, these stripes may introduce a difficulty, because they represent a nonuniform light intensity change, superimposed on the features of the frame. As already mentioned, the fringes are vertical (or horizontal) stripes which travel in position from frame to frame in a direction perpendicular to the stripes, in unison with the interferometer mirror(s) rotation.

The input of the fringe suppression algorithm is the cube of interferogram frames with fringes and the output a cube of frames without fringes, as further described hereinbelow.

Few assumptions are made concerning the operation of the fringes suppression algorithm.

One assumption is that the fringe "frequency" is approximately known. In other words, it is assumed that the distance in pixels between adjacent fringes is approximately known. One may gain this knowledge from previous experience on a certain type of sample, from each of the frames of the interferogram cubes themselves, or from a calibration process.

As seen in FIG. 7a, the fringe information is very compactly located in the frequency domain. The center frequency of the fringe can be easily found and the width of the fringe information in the frequency domain is assumed to be constant or nearly constant for all of the scanned frames.

The fringes suppression algorithm therefore suppresses the fringes by artificially zeroing or interpolating out the signal in the frequency range of the spatial frequency domain where the fringes information lies, for each scanned frame.

Figure 7B:
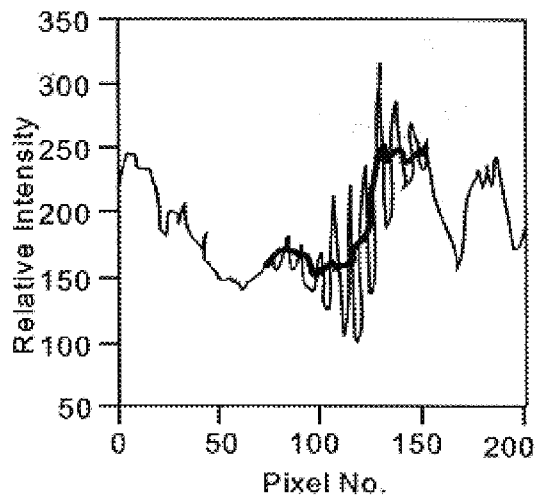
Figure 7C:
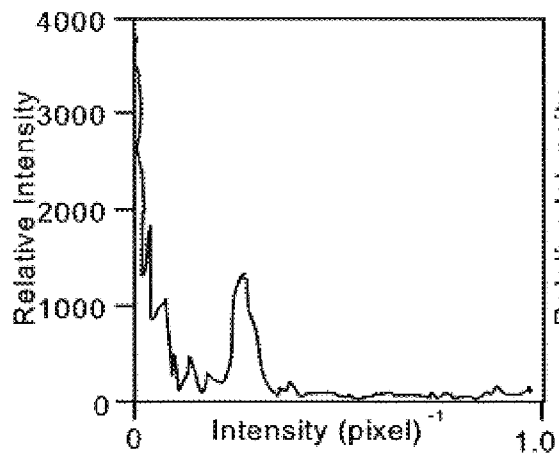
Figure 7D:
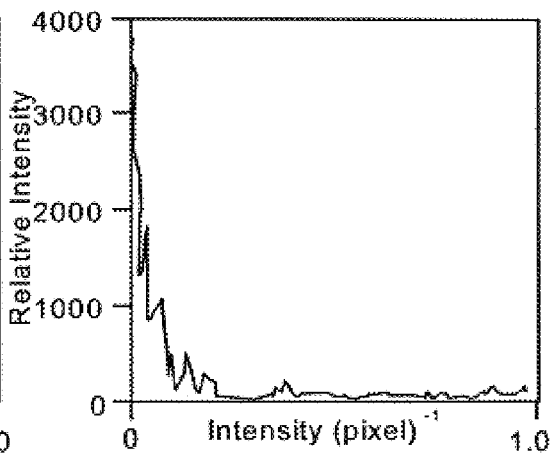
Figure 7E:
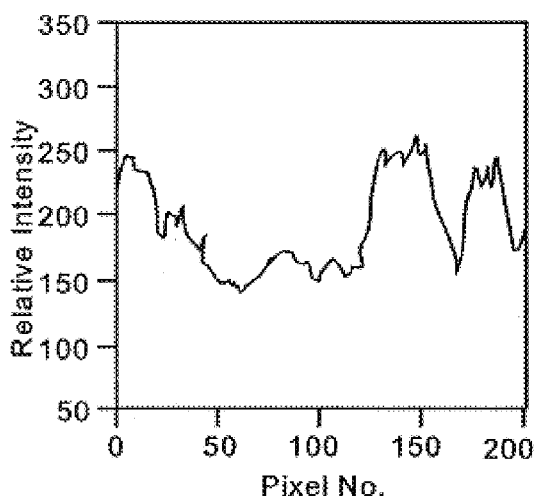
Figure 7F:
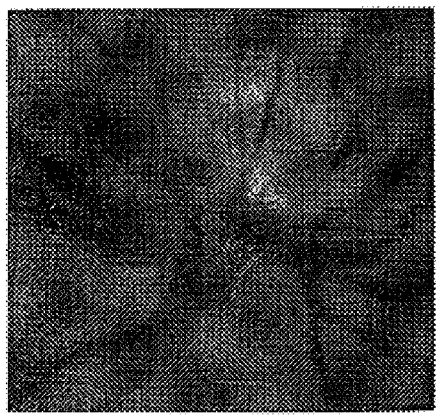

Since the fringes are almost parallel to one of the axes (say x-axis), one can divide the frame into vectors along the axis that is perpendicular to the fringes (say y-axis), each vector set of values being the intensity values of a raw or column of pixels. FIG. 7b shows the intensity values of 200 pixels of such a vector, wherein the fringes are clearly evident between the 100th pixel and the 150th pixel of this vector. As shown in FIG. 7c, each vector is thereafter transformed to the frequency domain using, for example, the fast Fourier transform algorithm (FFT), the peak ranging from ca. 0.15 to ca. 0.35 pixel$^{-1}$ contains the fringe information. As shown in FIG. 7d, for each vector the frequency region where the fringe information is located is zeroed, and, as shown in FIG. 7e, transformed back to the spatial domain using, for example, inverse fast Fourier transform algorithm (IFFT). This procedure is performed for each of the vectors of every frame grabbed by the spectral imager while scanning the interferometer and results in a fringes suppressed frame, as shown in FIG. 7f.

Should for some reason the fringes be offset angularly, i.e., not arranged in exact vertical or horizontal direction, a small decrease in the frequency of the fringe information band will result. This problem can be solved by increasing the width of the region of zeroing or interpolation of the signal in the spatial frequency domain where the fringe information lies.

As is evident from FIG. 7c, most of the frame's energy is located in the lower bands in the frequency domain. Using a band-stop filter not only preserves the information in each scanned frame but also doesn't blur the frame since the energy in the higher bands is not attenuated, and the edge information is preserved.

It will be appreciated by one ordinarily skilled in the art that using the Hough transform [Paul V. C. Hough, "Methods and means for recognizing complex patterns"; and U.S. Pat No. 3,069,654, both are incorporated by reference as if fully set forth herein], one can extract the frequency position of the fringe information and use it for the fringe suppression algorithm. The Hough transform can also find the orientation of those fringes and make the necessary adjustments.

To keep the signal real after the IFFT, the zeroing procedure is performed preferably symmetrically relative to the origin of the spatial frequency axis (Even though not shown in the Figure, the signal in the frequency domain is defined for both positive and negative values of the frequency f, and it is an even or symmetric function of f). The signal after the IFFT, as shown in FIG. 7e, has a very small imaginary residual part that is eliminated using the absolute (or the real) part of the result.

Returning to FIGS. 7b and 7e, instead of executing the FFT, zeroing and IFFT procedures as hereinabove described, one can simply interpolate the plot of FIG. 7b through the fringes region, intersecting each of the fringes intensity peaks substantially at their central relative intensity to obtain an interpolated plot, as indicated by I (for intersecting) in FIG. 7b, which is otherwise very similar to that shown in FIG. 7e.

An additional option is, for the region where the fringes information lies in the spatial frequency domain, instead of zeroing the peak (as shown in FIG. 7e), draw a straight line interpolation between the edge points of the peak.

The preferred fringe suppression algorithm according to the present invention is hereinbelow described in mathematical terms.

Let X(x,y) be the input frame (as, for example, shown in FIG. 7a), Y(x,y) the corresponding output frame (as, for example, shown in FIG. 7a), x and y are the discrete coordinates of a pixel in the frame, $f_{CF}$ the center frequency of the fringe information, $f_{LF}$ the low frequency of the fringe information, $f_{HF}$ the high frequency of the fringe information, $\Delta_f$ the width of the fringe suppression band and u(f) a step function.

By definition:

$$f_{LF} = f_{CF} - 0.5\Delta_f \quad (17)$$

$$fhd\ HF = f_{CF} + 0.5\Delta_f \quad (18)$$

A "zeroing band" function is defined as:

$$W(f)\ \{1-[u(f-f_{LF})-u(f-f_{HF})]-[u(f+f_{LF})-u(f+f_{HF})]\} \quad (19)$$

W(f) (the "zeroing band" function) is defined as a function of the frequency f such that, when multiplied by another function of the frequency f it leaves it unaltered for values off lower than $f_{LF}$ and higher than $f_{HF}$, and changes it to zero for values of f higher than $f_{LF}$ and lower than $f_{HF}$.

The output frame without fringes can then be expressed as:

$$Y(x,y) = Re\ \{IFFT\ \{W(f)*FFT\{X(:,y)\}\}\} \quad (20)$$

Using the fringe suppressed frames will assist in automatic registration procedures, which otherwise may face difficulties due to the repetitive pattern of the fringes superimposed on the frames.

EXAMPLE 4

SPECTRAL IMAGING OF SELECTED EYE TISSUES

The method described and exemplified under Example 3 above was employed to obtain spectral images of eye tissue of healthy and diseased patients as described in the following examples. It should, however, be noted that mechanical and chemical methods for eye fixation are well known in the art and are extensively employed during, for example, invasive eye procedures, such as laser operations. Such methods may also be employed for spectrally imaging eye tissues according to the present invention. Furthermore, as mentioned above, should the spectral imager of choice be a non-interferometer based imager (e.g., a filters based spectral imager), only conventional spatial registration is required for analyzing the eye. In addition eye tracking methods may be employed. Such methods are used in laser operations to track eye movement.

In the following, reflection of visible light illuminated via the iris was employed for spectrally analyzing eye tissues of healthy and diseased patients. Illumination was with white light and all the spectral data collected was between 500 and 620 nm. This is the region of hemoglobin absorption, which is the most prominent spectral feature of the retina. This spectral region, however, contains also the long wavelength tails of other absorbing structures: the eye media, the macular pigment and the melanin [Van Norren and L. F. Tiemeijer, Spectral reflectance of the human eye, Vision Res., Vol. 26 No. 2, pp.313–320, 1986].

Figure 9:
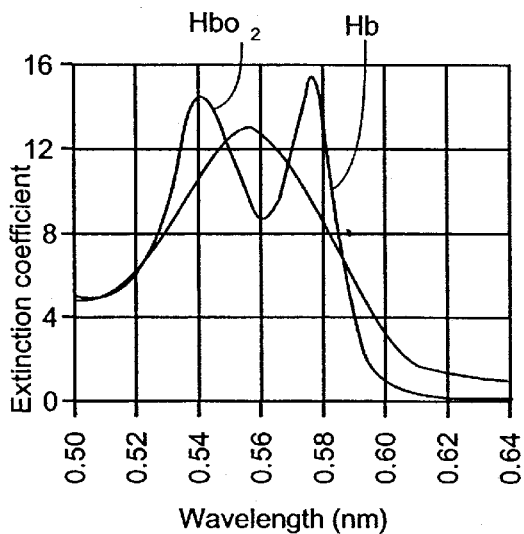
FIG. 9 presents plots of hemoglobin extinction coefficients from the literature.

The spectral variation of the specific extinction coefficients of oxygenated ($HbO_2$) and deoxygenated (Hb) hemoglobin are shown in FIG. 9 [see also Delori F. C., Noninvasive technique for oximetry of blood in retinal vessels, Applied Optics Vol. 27, pp. 1113–1125, 1988, taken from O. W. van Assendelft, Spectrophotometry of Hemoglobin Derivatives, C. C. Thomas, Springfield, Ill., 1970]. $HbO_2$ presents two peaks, at 540 and 578 nm, while Hb presents only one peak, at 558 nm. As is well known from the prior art [see for example, Delori F. C., Pfilbsen K. P., Spectral reflectance of the human ocular fundus, Applied Optics Vol. 28, pp. 1061–1077, 1989], peaks in the extinction coefficient mean dips in the reflectance spectrum. Delori [Delori F. C., Noninvasive technique for oximetry of blood in retinal vessels, Applied Optics Vol. 27, pp. 1113–1125, 1988] has shown how reflectance measurements of retinal vessels can be used to measure oxygen saturation ($O_2$Sat) and vessel diameter. Delori's work pioneered this field, but it was only related to vessels of the retina, and it had no imaging capability. As a result Delori did not present spatial maps of $O_2$Sat over the whole retina, and did not map the different regions of the ocular fundus, such as macula, disk, etc. on the basis of spectral information.

In this work the model presented by Shonat [Ross D. Shonat, Elliot S. Wachman, Wen-hua Niu, Alan P. Koretsky and Daniel Farkas, Simultaneous hemoglobin saturation and oxygen tension maps in mouse brain using an AOTF microscope, Biophysical Journal (1997), in press] was extended to fit the spectra of all retinal regions so that the data of a whole spectral image can be used to map various features, such as, but not limited to, vessels, $O_2$Sat, optical density of total hemoglobin, spectral differentiation between healthy, intermediate and degenerate macular tissue, spectral differentiation between healthy and glaucomatous optic disks and cups, etc.

a. Modeling the retina

Figure 8A:
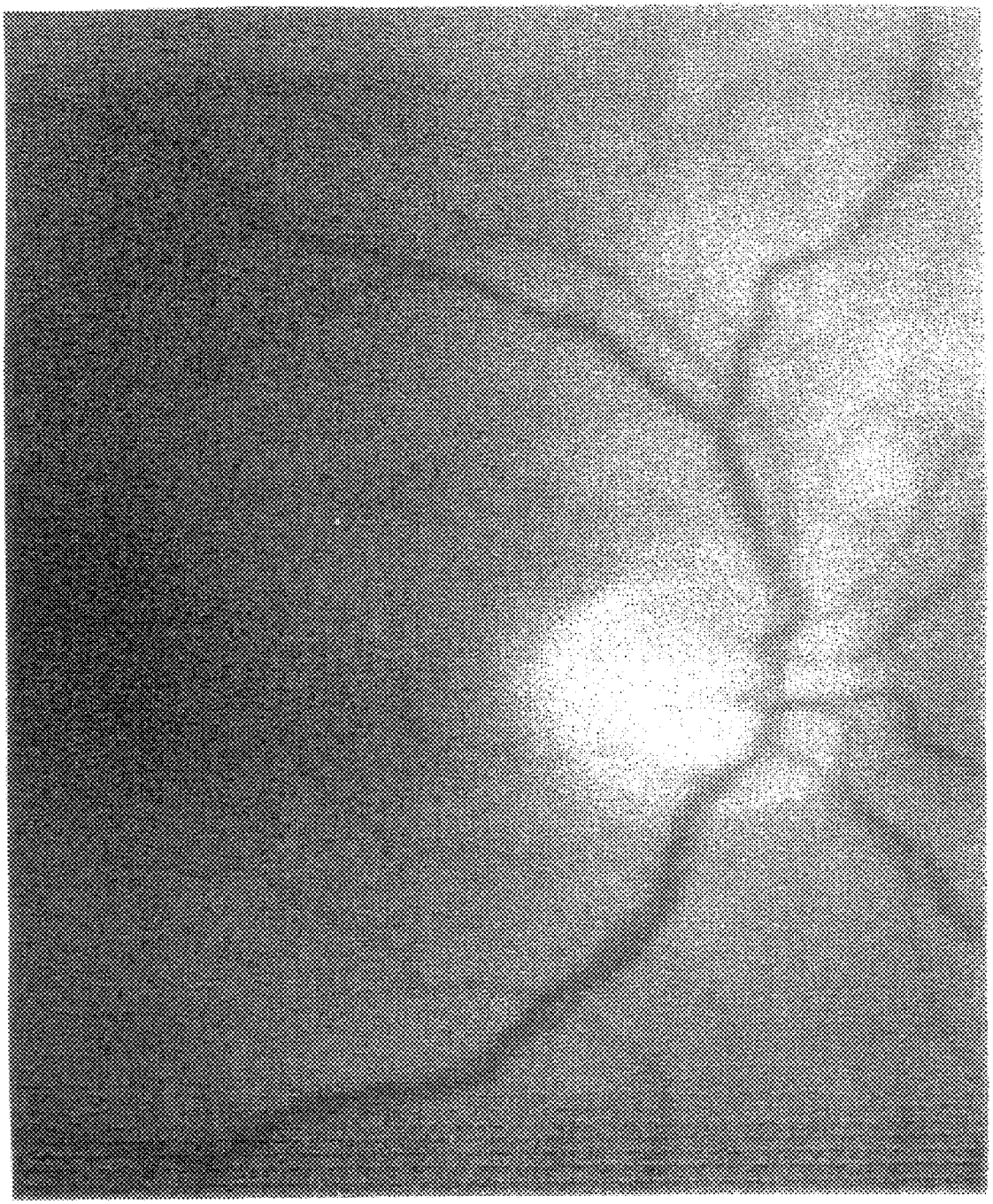
FIGS. 8a and 8b presents a spectral image of a healthy retina. Spectrally distinct regions are designated in FIG. 8b.
Figure 8B:

FIGS. 8a–b show spectral images of a retina obtained using the SPECTRACUBE spectral imager. The color presented by each pixel in the images is determined by an RGB algorithm as described under Example 2 above. The weighting functions were $w_r$(=570–620 nm), $w_g$(=530–570 nm) and $w_b$(=500–530 nm) mimicking full transmission in the selected ranges and no transmission outside the selected ranges.

Figure 10:
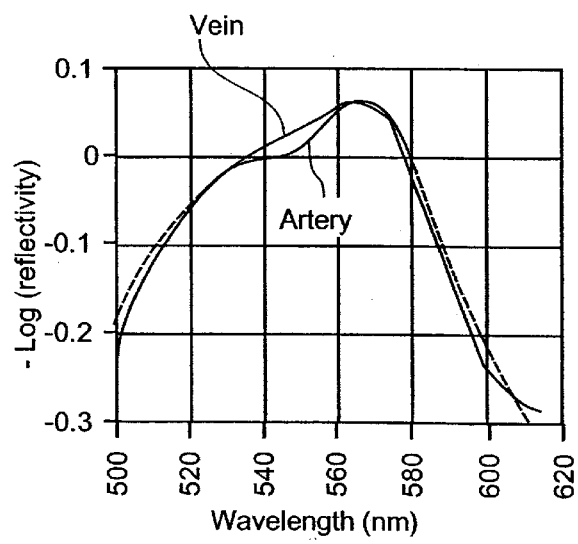
FIG. 10 presents plots of inverted log of reflectivity spectra of a vein and an artery.

FIG. 10 shows the inverted log of reflectivity spectra (proportional to extinction coefficient), as measured by the SPECTRACUBE system, of one pixel of a vein and one of an artery. It is seen that the peaks in the vein are less pronounced than in the artery, as expected from the known oxygenated and deoxygenated hemoglobin extinction spectra shown in FIG. 9.

Figure 11:
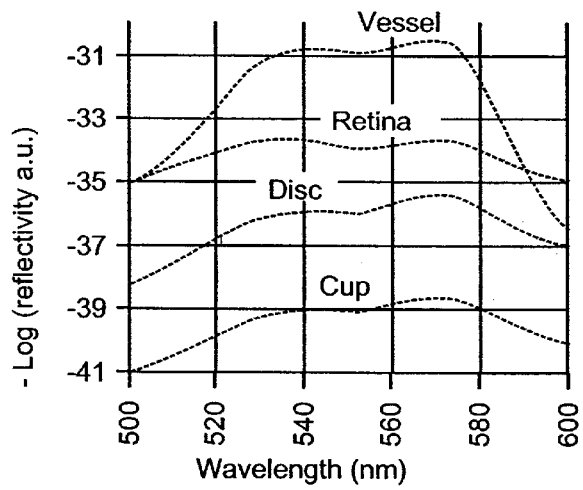
FIG. 11 presents spectra of pixels from the disk, the cup, the retina, and a retinal vessel, as measured according to the present invention.

FIG. 11 shows spectra of pixels from the disk, the cup, the retina, and from a retinal blood vessel. The spectral resolution of this measurement is low, approximately 20 nm, and this is the reason for the shallowness of the dips seen. It is well known in the literature [for example, Patrick J. Saine and Marshall E. Tyler, Ophthalmic Photography, A textbook of retinal photography, angiography, and electronic imaging, Butterworth-Heinemann, Copyright 1997, ISBN 0-7506-9793-8, p. 72] that blue light is mostly reflected by the outer layers of the retinal tissue, while as the wavelength increases, the light is reflected by deeper and deeper layers.

Figure 12:
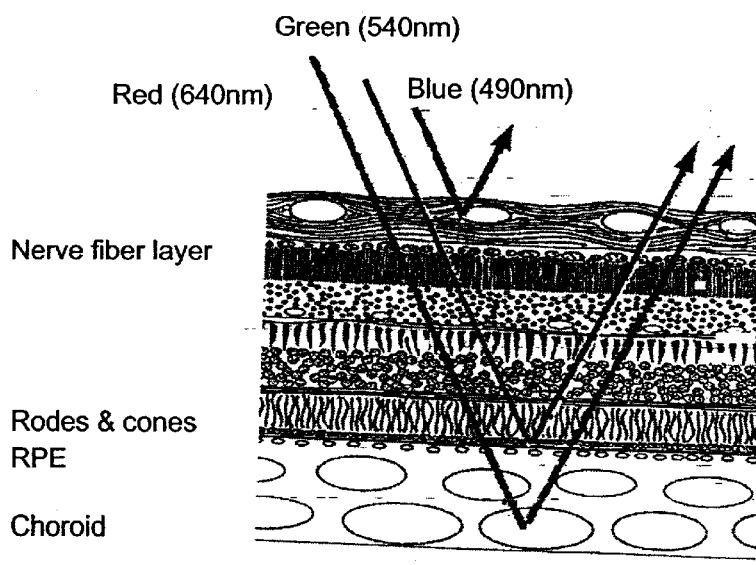
FIG. 12 is a schematic cross section of the retina, demonstrating the reflection of different wavelengths from different retinal depths.

FIG. 12 is a schematic diagram of the reflection of different wavelengths from different retinal depths. This means that monochromatic images show features characteristic of different depths.

Different models, such as, for example, the well known $O_2$Sat model used by Delori for retinal vessels, and by Shonat et al., on the surface of rat brain, [Delori F. C., Noninvasive technique for oximetry of blood in retinal vessels, Applied Optics Vol. 27, pp. 1113–1125, 1988, and Ross D. Shonat, Elliot S. Wachman, Wen-hua Niu, Alan P. Koretsky and Daniel Farkas, Simultaneous hemoglobin saturation and oxygen tension maps in mouse brain using an AOTF microscope, Biophysical Journal (1997), in press, both are incorporated by reference as if fully set forth herein], and modifications thereof, might be used to fit the spectral data in each pixel of the image separately to explain the results.

Such models, if successful, might predict the presence, absence or amount of physiologically important metabolites, such as, but not limited to, hemoglobin, cytochromes, oxidases, reductases, NAD, NADH and flavins, pixel by pixel, and, once displayed in a spatially organized way, may be the basis for highlighting regions of impaired tissue "vitality" or "viability".

Figure 13A:
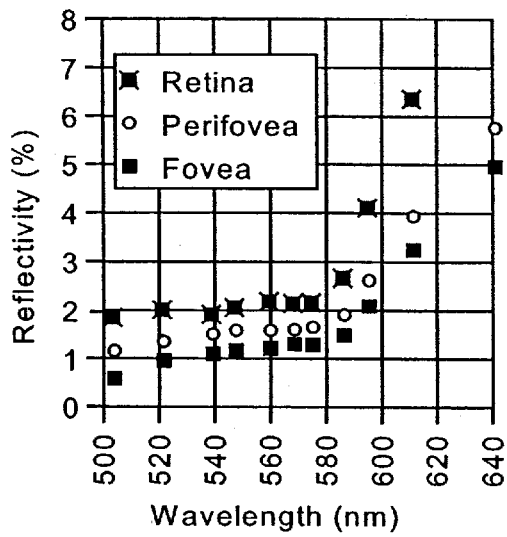
FIGS. 13a–c compares plots of spectra extracted from several eye regions reported in the prior art (13a) with spectra measured according to the present invention of the same regions (13b) and of other regions (13c).
Figure 13B:
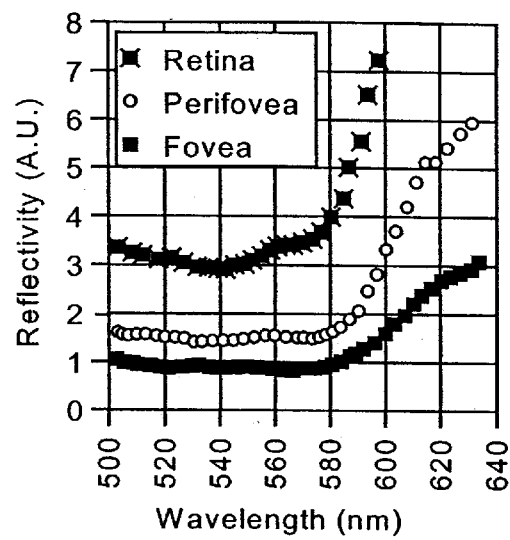
Figure 13C:
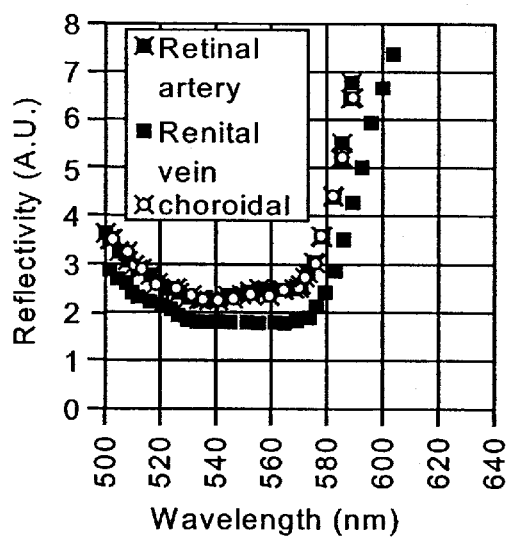

FIGS. 13a–c shows spectra extracted from several pixels of a spectral image measured with the SPECTRACUBE system, belonging to different anatomic regions of the retina (FIGS. 13b–c) as compared to spectra measured and published by Delori (FIG. 13a). FIG. 13a presents spectra described by Delori derived from the retina, perifovea and the fovea using point spectroscopy. FIGS. 13b–c presents spectra measured using the SPECTRACUBE system of the same tissues (FIG. 13b) and of a retinal artery, retinal vein and a choroidal blood vessel (FIG. 13c). Comparing FIGS. 13a and 13b, the similarity of the results is evident, although there are also some differences, which may be due to patient variability.

FIG. 13c shows the spectra of a retinal artery and a retinal vein and of a choroidal blood vessel. The peak at 560 nm is more pronounced in the artery and the choroidal vessel than in the vein, as expected from higher oxygenation of hemoglobin thereat.

Figure 14A:
FIGS. 14a–e present an RGB image, an enhanced RGB image, a 610 and 564 nm images and a hemoglobin oxygenation image of portion of a retina including retinal blood vessels of a healthy individual.

FIGS. 14a–e show a portion of retina including retinal blood vessels from a healthy individual. FIG. 14a shows an RGB image of the retina, wherein $w_r$(570–620 nm), $w_g$(530–570 nm) and $w_b$(500–530 nm).

Figure 14B:
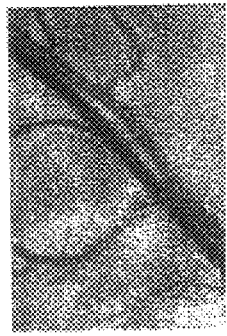

FIG. 14b shows an enhanced RGB image of the retina. The intensities of the three colors, red, green and blue, i.e., RGB, are related algebraically to the normalized intensities in the three spectral bands B1, B2 and B3, defined as follows B1=525–590 nm, B2=600–620 nm and B3 =500–650 nm. In each of these bands the integral intensity was calculated for each pixel. The intensity was then scaled so that the minimum value over the whole image was zero and the maximum value was one. The red intensity was then given by: R=B2/(1+B1); the green intensity was given by: G=B3; whereas the blue intensity was given by B=(1+B1−B2)/(1+B1). The latter RGB algorithm was employed to specifically enhance the spectral difference between retinal veins (dark red) and arteries (light red). Thus, using the present invention it is possible to strongly enhance metabolic characteristics of the retina and retinal blood vessels.

Figure 14C:
Figure 14D:

FIGS. 14c and 14d are gray level images wherein for each pixel light of the specified wavelengths (610 and 564 nm, respectively) is given a gray level according, to its intensity. Please note that only the vein is highlighted at 610 nm, whereas both arteries and the vein are highlighted at 564 nm. Thus, images at different wavelengths are shown to highlight different aspects of the retinal physiology.

Figure 14E:

FIG. 14e is a hemoglobin oxygenation map for the retinal blood vessels. The map of FIG. 14e was calculated using, for each pixel, the algorithm for $O_2$Sat developed by Shonat [Ross D. Shonat, Elliot S. Wachman, Wen-hua Niu, Alan P. Koretsky and Daniel Farkas, Simultaneous hemoglobin saturation and oxygen tension maps in mouse brain using an AOTF microscope, Biophysical Journal (1997), in press].

Deoxygenated blood has a higher extinction coefficient in the red wavelengths than oxygenated blood (FIG. 9), and therefore veins look slightly darker and with a slightly different color than arteries, because they carry blood at different levels of oxygenation (see FIG. 14a). However, the color difference is very small and in a conventional color image of the fundus, it can be hard to distinguish between them, except, in some cases, for the largest vessels. Oxygenation mapping or simple enhancing artificial RGB mapping based on spectral features may be a tool that significantly enhances the distinction between the different type of vessels.

Figure 15:
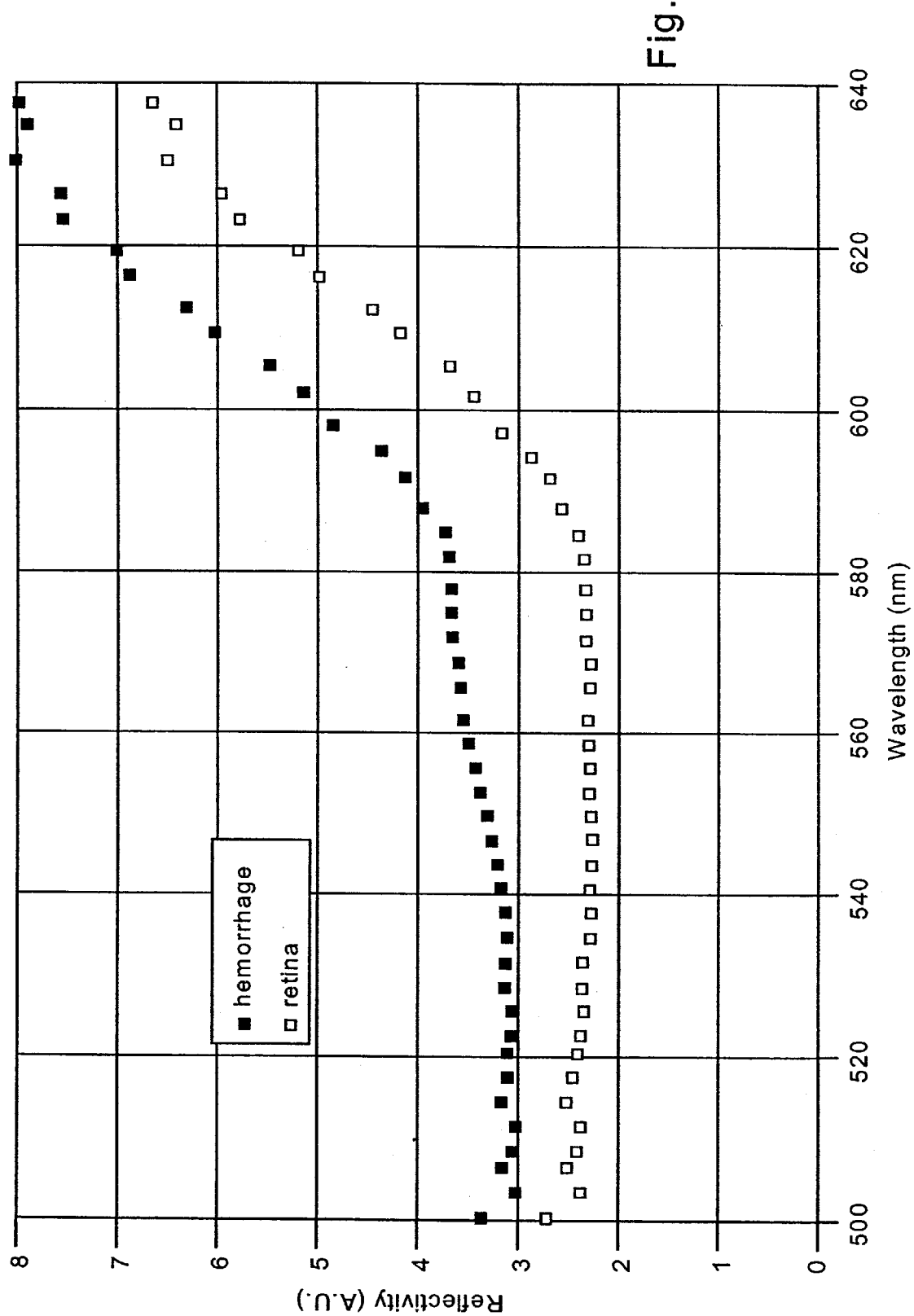
FIG. 15 presents plots of spectra derived from a hemorrhage and healthy retinal regions, according to the present invention.

FIG. 15 shows spectra derived from a hemorrhage and healthy retinal regions of a patient suffering from diabetic retinopathy. Please note that the spectra of the affected retinal region is much flatter, probably due to lower levels of oxygenated hemoglobin than the one present in healthy retina.

b. Modeling the macula

Inverted log spectra of the macula have been shown by Brindley et al. [G. S. Brindley and E. N. Willmer, The reflexion of light from the macular and peripheral fundus oculi in man, Journal of Physiology Vol. 116, pp. 350–356, 1952]. Spectral reflectance of the fovea and the log reflectance difference of the normal periphery and fovea are shown by Van Norren et al. [Van Norren and L. F. Tiemeijer, Spectral reflectance of the human eye, Vision Res., Vol. 26 No. 2, pp. 313–320, 1986].

Figure 16:
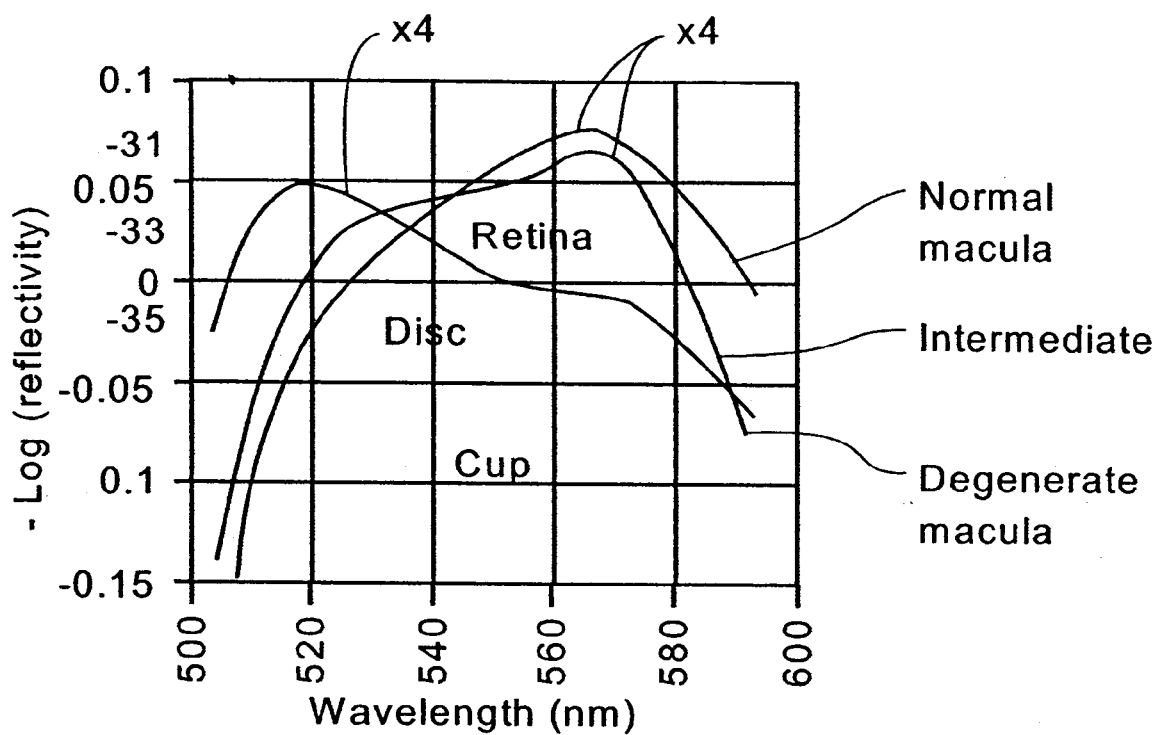
FIG. 16 presents plots of inverted log reflectivity spectra of normal, intermediate and degenerate macular tissue of a single patient suffering macular degeneration, as measured according to the method of the present invention.

FIG. 16 shows the inverted log reflectivity spectra of normal, intermediate and degenerate macular tissue of a single patient suffering macular degeneration. The spectra for the macular tissue represents average of twenty five pixels per region. The spectrum of the degenerated macula was divided by a factor of four as indicated by "x4". It is clearly evident that the spectral signature of the normal, intermediate and degenerated macular tissue are definitely different from one another. Please note that a gradual spectral change toward degeneration spectral signature is apparent in the intermediate tissue. The gradual spectral change from normal to diseased tissue may be used for early detection of the disease and for following disease progression.

Figure 17:
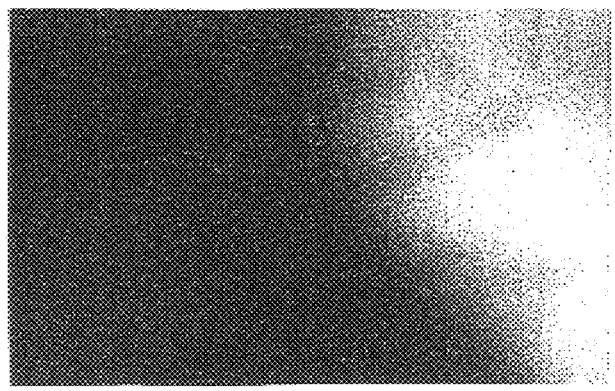
FIG. 17 presents an RGB image of a region in the macula of the patient of FIG. 16.

FIG. 17 shows a region in the macula of the above patient ranging from normal (dark) to degenerate (light). The algorithm employed to enhance the spectral signatures of the macular regions was an RGB algorithm where $w_r$(570–620 nm), $w_g$(530–570 nm) and $w_b$(500–530 nm) weighting functions were selected. Please note that while normal macular tissue absorbs most of the illuminated light (i.e., reflects a small fraction thereof) and therefore appears dark, degenerated macular tissue reflects most of the light (i.e., absorbs a small fraction thereof) and therefore appears light. This result is in good agreement with the presence of cones and rods in normal macula and their absence from degenerated macula, since the rods and cones are, by nature, excellent light absorbers.

c. Modeling the optic disk

Because of the great importance of the optic disk physiology in the diagnosis of glaucoma, results of the analysis of the spectral images as they pertain to this region of the ocular fundus are presented.

Figure 18A:
FIGS. 18a–d present an RGB image, a 610 and 564 nm images and a hemoglobin concentration image of an optic disk of a healthy individual.
Figure 18B:
Figure 18C:
Figure 18D:
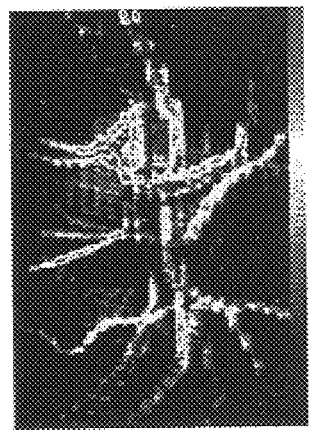

FIGS. 18a–d show the optic disk of a healthy individual. FIG. 14a shows an RGB image of the disk, wherein $w_r$(570–620 nm), $w_g$(530–570 nm) and $w_b$(500–530 nm). FIGS. 18b and 18c are gray level images wherein for each pixel light of the specified wavelengths (610 and 564 nm, respectively) is given a gray level according to its intensity. FIG. 18d is a hemoglobin concentration map of the disk blood vessels. The map of FIG. 18d was calculated using, for each pixel, an algorithm similar to that used for Hb concentration by Shonat [Ross D. Shonat, Elliot S. Wachman, Wen-hua Niu, Alan P. Koretsky and Daniel Farkas, Simultaneous hemoglobin saturation and oxygen tension maps in mouse brain using an AOTF microscope, Biophysical Journal (1997), in press].

FIGS. 19a–e show the optic disk of a glaucoma suspect. FIG. 19e is an image key, schematically presenting the location of the optic disk and cup in FIGS. 19a–d. FIG. 19a shows an RGB image of the disk, wherein $w_r$(570–620 nm), $w_g$(530–570 nm) and $w_b$(500–530 nm). FIGS. 19b and 19c are gray level images wherein for each pixel light of the specified wavelengths (610 and 564 nm, respectively) is given a gray level according to its intensity. FIG. 19d is a hemoglobin concentration map of the disk blood vessels. The map of FIG. 19d was calculated using, for each pixel, an algorithm for Hb concentration similar to that used by Shonat [Ross D. Shonat, Elliot S. Wachman, Wen-hua Niu, Alan P. Koretsky and Daniel Farkas, Simultaneous hemoglobin saturation and oxygen tension maps in mouse brain using an AOTF microscope, Biophysical Journal (1997), in press]. The plots under and to the right of FIG. 19d represent the hemoglobin concentration along the horizontal and vertical lines crossing FIG. 19d.

Please note that a striking difference in hemoglobin concentration is clearly evident comparing the images of the healthy individual (FIG. 18d) and the glaucoma patient (FIG. 19d).

EXAMPLE 5

SPECTRALLY IMAGING CHOROIDAL VESSELS AND OTHER FEATURES IN THE CHOROIDAL LAYER OF THE EYE

U.S. Pat. application No. 08/942,122 describes the use and the advantages of spectral imaging systems for mapping and measuring anatomic and physiologic features of the ocular fundus. Examples of hemoglobin and oxygen saturation maps, nerve fiber layer mapping, choroidal vessels imaging, macula, fovea and macular degeneration maps, etc., are described therein and hereinabove and shown to be distinguished by different spectra.

In the present example it is shown how to obtain enhanced images of the choroidal vessels and choroidal layer from spectral images measured with the SPECTRACUBE and in this respect also other high throughput spectral imagers.

Figure 20:
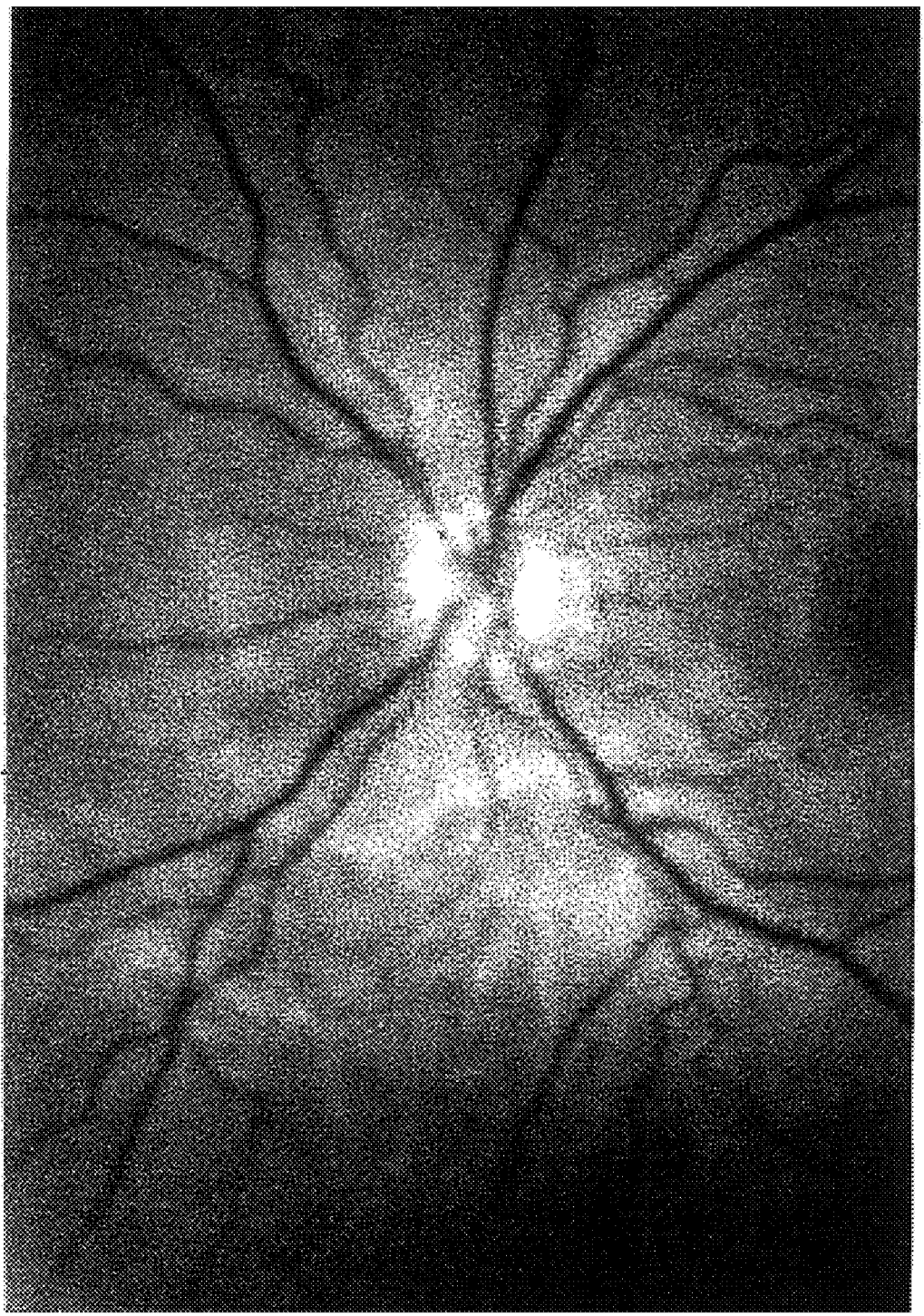
FIG. 20 presents a RGB image of the ocular fundus calculated on the basis of the spectra of each pixel as measured through a green filter by the SPECTRACUBE SD200 model attached to a fundus camera. The green filter is used to avoid saturation of the signals due to high response in the red and infrared wavelengths.

FIG. 20 shows a typical color image of a healthy retina. The image was obtained by first measuring the retina as described in U.S. Pat. application No. 08/942,122, including the interferogram corrections and spatial registration described in PCT/US97/08153, which is incorporated by reference as if fully set forth herein, and then displaying its RGB (Red, Green and Blue) image according to the method described in U.S. Pat. No. 5,784,162, namely calculating a tristimulus vector for every pixel of the image on the basis of the spectral image measured by means of the SPECTRACUBE system and then displaying the result in color. This image is very similar to a usual digital color image as obtained through a standard fundus camera.

It is easy to recognize in this image the dark macular region, the bright optic disk, various superficial vessels, and, in the background, a quite unclear and fuzzy set of vessels, which are recognized to be choroidal vessels.

According to this aspect of the present invention the spectral data thus collected is used to provide an image in which the choroidal vessels are mostly emphasized and brought out of the background in a quite sharp and clear way, never realized before, using only reflected white light.

Once this is obtained one can also present images in which the relatively sharp contrast choroidal vessels are shown superimposed on the superficial vessels and the rest of the retina.

Such superimposed images have the potential to be most useful for assessing the vitality, metabolic and pathologic state of the choroidal layer.

Figure 21:
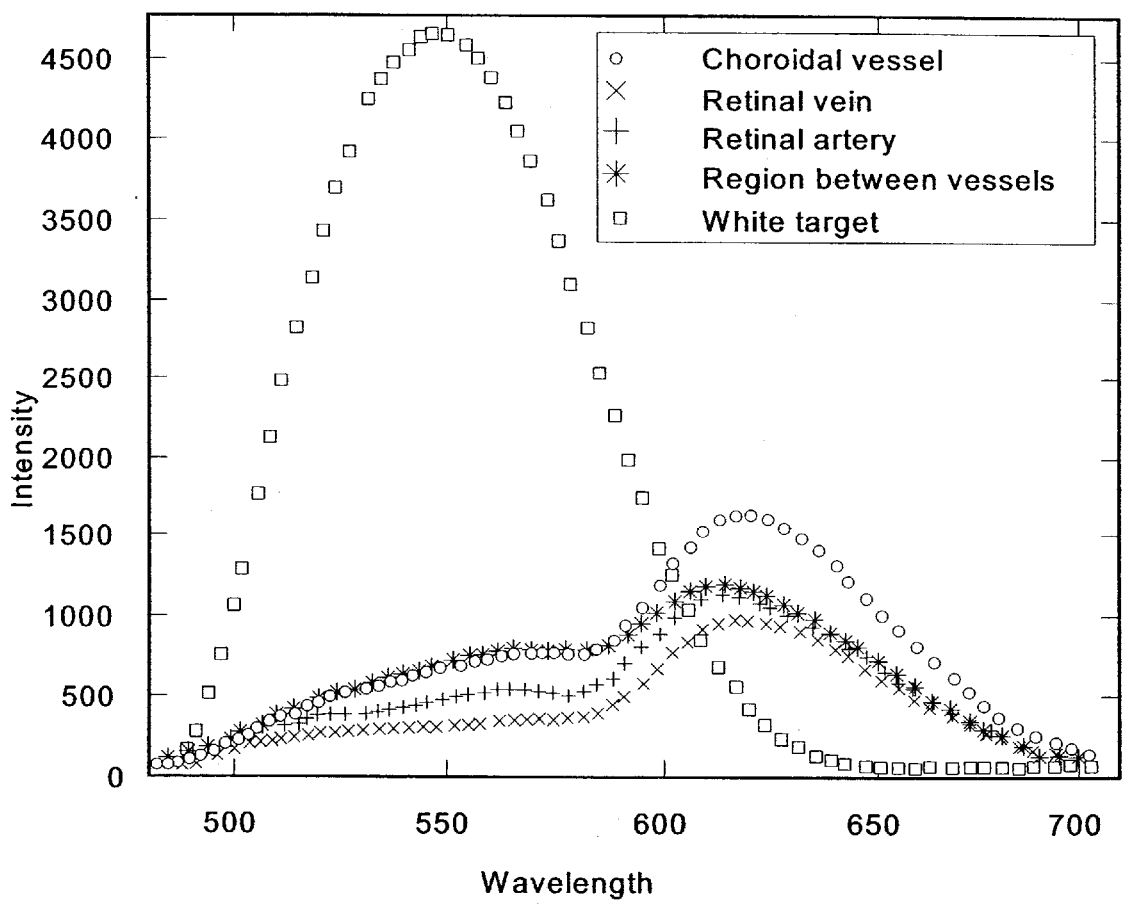
FIG. 21 shows selected spectra of different features of the ocular fundus extracted from the spectral image measurement of FIG. 20, and illumination spectrum of the source used, as measured by the SPECTRACUBE attached to a fundus camera and through the same green filter as before. Please note that the spectra of the features and the spectrum of the illumination are shown in a different scale: the features spectra are amplified in order to show more details.

For this purpose, first consider the spectra shown in FIG. 21. These are typical spectra as measured by the SPECTRACUBE, of pixels which are located respectively on a choroidal vessel (C), on a superficial vein (V), a superficial artery (A) and a region of tissue between these vessels (R). It can be seen that in the wavelength region of 500 to 600 nm, the spectra of C and R regions are very close to each other, while V and A are different than all the others. At about 585 nm the spectrum of R starts to deviate from C and approaches the spectrum of A, while at about 620 nm V starts to approach A; at about 640 nm and above, the spectra of R, V and A are almost identical while very different from C. The data above 650 nm are not reliable, because the measurement was made through a red free filter with a cutoff at approximately 650 nm.

In order to show that the results between 600 and 650 nm are not an artifact due to the signal suppression by the cutoff filter around and above 600 nm, the above spectra were normalized by dividing them, wavelength by wavelength, by the illumination spectrum which is represented by the "white target" spectrum shown in FIG. 21. This is the spectrum as measured through the instrument of a white reflector (which is highly uniform over all wavelengths), and is basically proportional to the light source spectrum multiplied by the transmission spectrum of the green filter, the transmission of the instrument optics and the spectral response of the detector. The negative logarithm of that ratio is shown in FIG. 3 for all the spectra C, V, A and R. Because of this normalization, the spectra shown in FIG. 3 are independent of instrumentation parameters.

Figure 22:
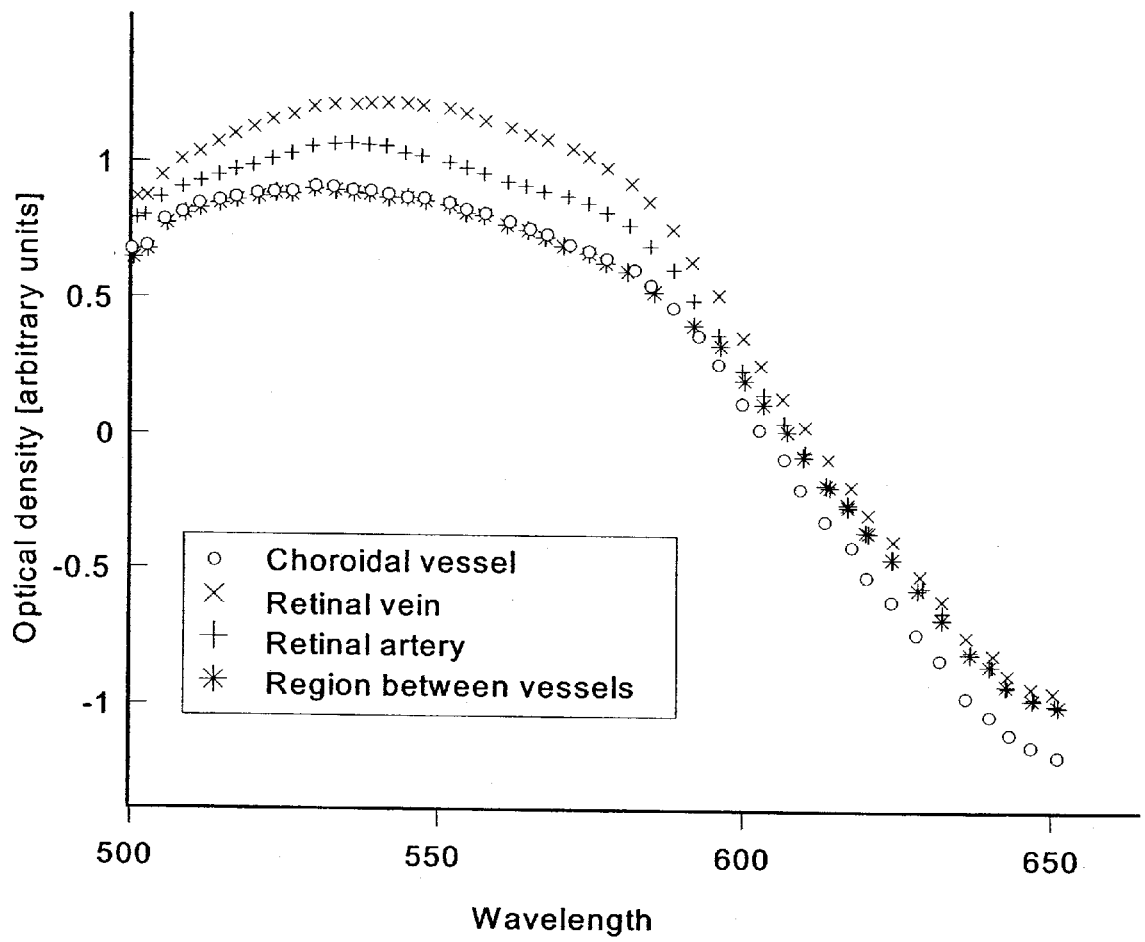
FIG. 22 shows logarithms of the inverse ratio of the spectra of the fundus features of FIG. 21 divided by the illumination spectrum of FIG. 20. These spectra do not depend on instrument response and illumination spectrum.

In order to show this more exactly, one can define $F_e(\lambda)$ as the spectrum of the radiation reflected by a retinal feature, $p(\lambda)$ as the spectral reflectivity of the retinal feature, $F(\lambda)$ as the spectrum of a retinal feature (shown in FIG. 21) as measured, $R_e(\lambda)$ as the spectrum of the illumination source as reflected by the "white target", $R(\lambda)$ as the illumination spectrum as measured (shown in FIG. 21), $K(k)$ as the spectral response of the SPECTRACUBE including the optical transmission, the green filter spectral transmission and the detector response, and $F_n(\lambda)$ as the inverse logarithm of the normalized spectrum of a retinal feature (from FIG. 22).

The following relations then take place:

$$F(\lambda)=F_e(\lambda)\times K(\lambda) \quad (21)$$

$$Fe(\lambda)=\rho(\lambda)\times R_e(\lambda) \quad (22)$$

$$R(\lambda)=R_e(\lambda)\times K(\lambda) \quad (23)$$

$$F_n(\lambda)=-\log[F(\lambda)/R(\lambda)] \quad (24)$$

It follows from Equations 21 and 22 that:

$$F(\lambda)=\rho(\lambda)\times R_e(\lambda)\times K(\lambda) \quad (25)$$

and from Equations 23–25 it follows that:

$$F_n(\lambda)=-\log[\rho(\lambda)\times R_e(\lambda)\times K(\lambda)/R_e(\lambda)\times K(\lambda)]=-\log[\rho(\lambda)] \quad (26)$$

The resulting $F_n$ spectra calculated according to Equation 26 for the different retinal features, are displayed in FIG. 22, and obviously the right hand side of Equation 26 shows that these spectra are independent of the illumination and instrumentation used for the measurement, since $\rho(\lambda)$ is a characteristic of the retinal feature in question.

It is seen that the behavior shown in FIG. 21 holds here too, namely that C and R are approximately identical between 500 and 585 nm and different from A and V, while above 620 nm V, A and R are very close to each other, while different than C.

Figure 23:
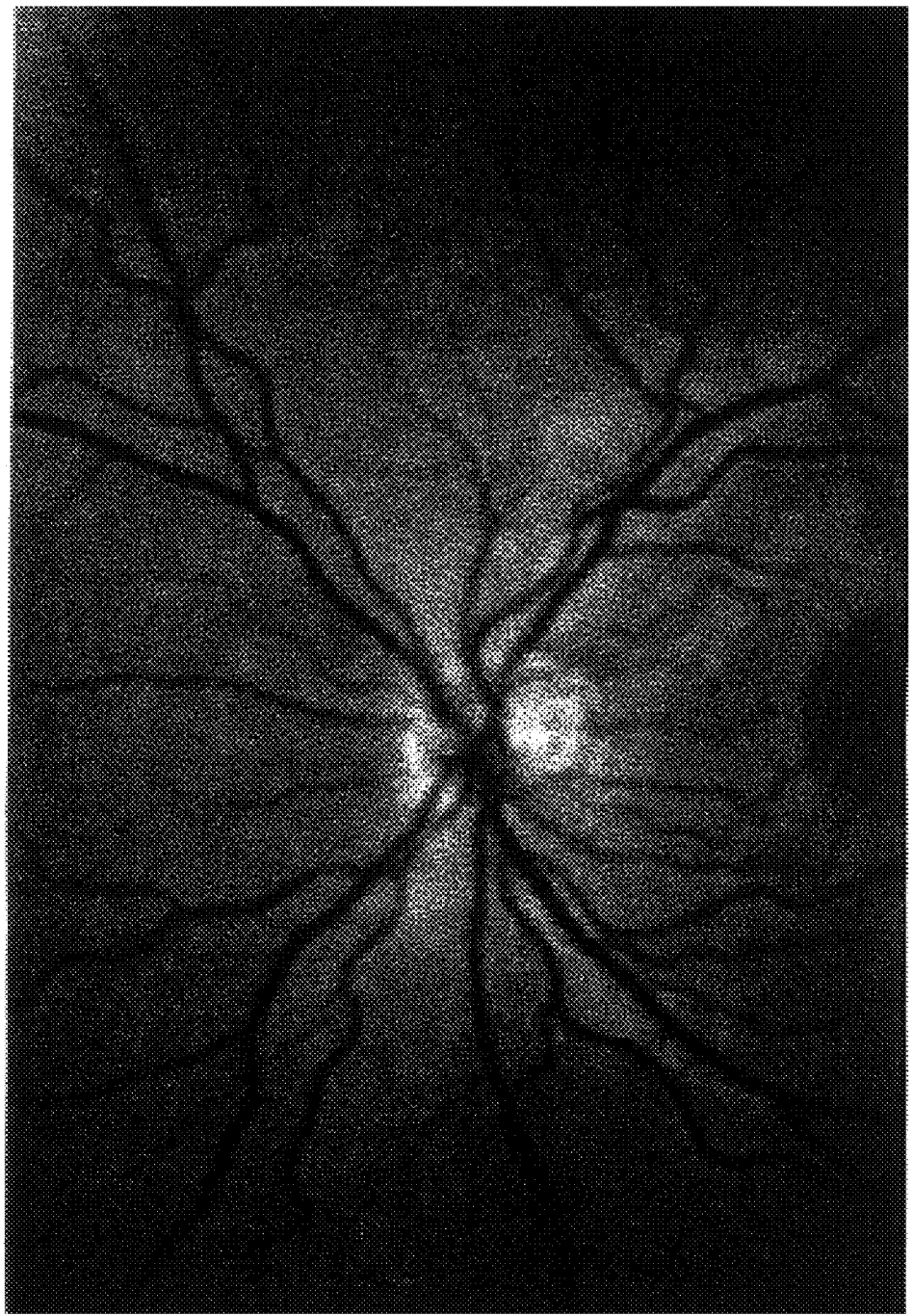
FIG. 23 shows gray scale image extracted from the spectral image measurement of FIG. 20 at 550 nm.
Figure 24:
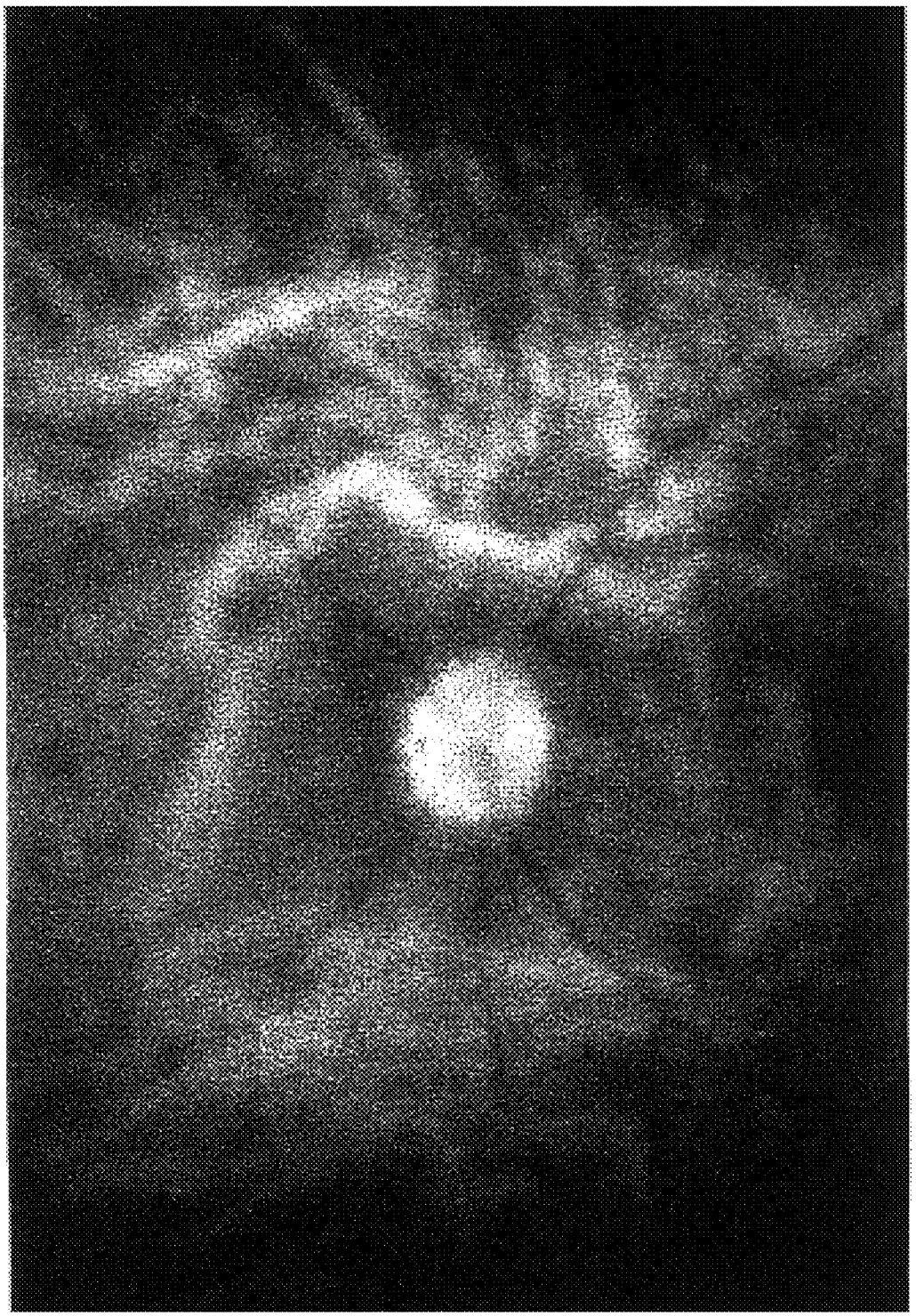
FIG. 24 shows gray scale image extracted from the spectral image measurement of FIG. 20 at 650 nm.

As a result of this spectral behavior it can be easily understood that a gray scale (level) image at a wavelength or in a wavelength range near 550 nm will show a large contrast between superficial veins, arteries and retinal tissue (dark vessels in a bright retinal background) with no contrast between choroidal vessels and retinal tissue, while a gray scale image at a wavelength or in a wavelength range around 650 nm will show high contrast of bright choroidal vessels on a darker retinal background and almost no contrast between superficial vessels themselves and between them and retinal tissue. FIGS. 23 and 24 show this behavior respectively.

Figure 25:
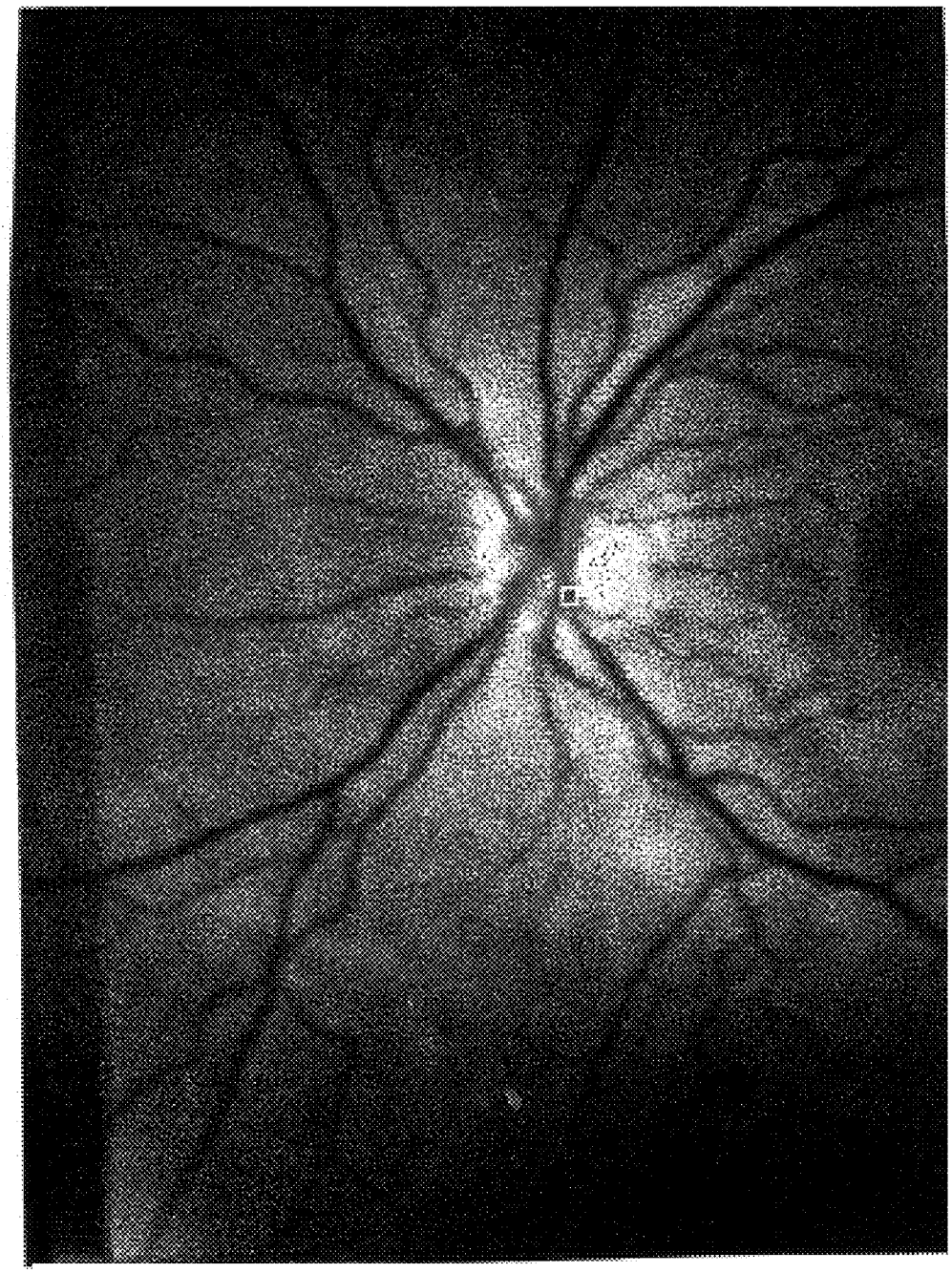
FIG. 25 is a superimposition of choroidal vessels and retinal vessel system in one image, obtained by a specially designed algorithm, using the spectral image of FIG. 20.

FIG. 25, in turn, shows superposition of the choroidal vessels analyzed as described over the image of FIG. 20 obtained by an RGB display using the spectral ranges red –578–650 nm, green –542–578 nm and blue –500–542 nm.

The following lists potential applications of this aspect of the present invention. Although not exhaustive, the following list, together with the mentioned references, will clarify and exemplify the type of medical utility this aspect of the present invention is meant for. In any case, it is recognized that the method disclosed herein may help in more timely and accurate diagnosis, more effective treatment, and treatment follow up, by basically replacing the ICG angiography method for the analysis of choroidal vessels and similar and/or related features and pathologies of the ocular fundus. The cited references also give an idea of the types of methods and modalities which are used or researched at present for the study and diagnosis of the relevant diseases and pathologic conditions.

1. Retinal pigment epithelium (RPE) detachments, see for example Disparity between fundus camera and scanning laser ophthalmoscope Indocyanine green imaging of retinal pigment epithelidetachments, by Flower R W et al., Retina. 1998; 18(3): 260–268.

2. Choroidal and ciliary body melanomas, see for example The microcirculation of choroidal and ciliary body melanomas, by Folberg R et al., Eye. 1997; 1 1( Pt 2): 227–238. Review, Imaging the microvasculature of choroidal melanomas with confocal Indocyanine green scanning laser ophthalmoscopy. By Mueller A J et al., Arch Ophthalmol. 1998 Jan; 116(1): 31–39

3. Choroidal neovascularization in age-related macular degeneration, exudative maculopathy due to age-related macular degeneration, and intrinsic tumor vasculature of choroidal malignant melanomas, see for example ICG videoangiography of occult choroidal neovascularization in age-related macular degeneration, by Atmaca L S et al., Acta Ophthalmol Scand. 1997 Feb; 75(1): 44–47, Classification of choroidal neovascularization by digital Indocyanine green videoangiography. Ophthalmology, by Guyer D R et al., Ophthalmology, 1996 Dec; 103(12): 2054–2060, and Indocyanine green videoangiography of malignant melanomas of the choroid using the scanning laser ophthalmoscope, by Schneider U et al., Ger J Ophthalmol. 1996 Jan; 5(1): 6–11, 4. Sub-retinal structures, central serous chorioretinopathy, photophysiology and treatment of diseases affecting the retinal pigment epithelium and Bruch's membrane, such as age-related macular degeneration, see, for example, Infrared imaging of central serous chorioretinopathy: a follow-up study, by Remky A et al., Acta Ophthalmol Scand. 1998 Jun; 76(3): 339–342, Infrared imaging of sub-retinal structures in the human ocular fundus, by Elsner A E et al., Vision Res. 1996 Jan; 36(1): 191–205, Imaging of chorioretinal anastomoses in vascularized retinal pigment epithelium detachments, by Kuhn D et al., Arch Ophthalmol. 1995 Nov; 113(11): 1392–1398.

5. Retinal hemorrhages, retinal circulation and late leakage sites, choroidal circulation, posterior uveal tumors abnormal vessels in such tumors, see Indocyanine green angiography in retinal hemorrhage of uncertain origin, by Schneider U et al., Klin Monatsbl Augenheilkd. 1995 Dec; 207(6): 372–376, The value of medical imaging techniques in the diagnosis of extra-ocular extension of malign melanoma of the choroid: a case report, by Sallet G et al., Bull Soc Belge Ophtalmol. 1993; 248: 53–58.

All of the above references are incorporated by reference as if fully set forth herein.

EXAMPLE 6

NON-INVASIVE OPHTHALMIC ANGIOGRAPHY BY SPECTRAL IMAGING

In today's medical practice, the major source of contrast in retinal angiographic images is the fluorescent emission from either fluorescein sodium or indocyanine green dye which attach as molecules to blood plasma proteins (albumins in particular). Fluorescein sodium is absorbed by hemoglobin as well. In this way, retinal angiography allows the ophthalmologist to study the entire vasculature, not just the major arteries and veins within the retina or choroid, as the dye perfuses through the smaller vessels and capillaries.

In contrast, this example of the present invention relies on the spectrally dependent absorption of intrinsic hemoglobin. This acts as the source of contrast within the spectral image of the retina providing the same visualization of the entire vasculature, in the absence of any dye being injected into the circulatory system of the patient.

The theoretical basis for the following hemoglobin concentration based contrast enhancement algorithm is as follows.

A simple model to describe the spectrum obtained by reflection of white light from the retina is based on the assumption that the spectrum $I(\lambda)$ (Equation 27) is made up of a signal transmitted through a partially absorbing layer (retina or blood vessel) and reflected off a white substrate (sclera). The reverse optical path, i.e., reflected off the sclera to then traverse the partially absorbing layer is of course equivalent. This signal is multiplied by the "white calibrator" function $W(\lambda)$ which contains the spectral characteristics of the system response, i.e., light source, detector sensitivity etc.

$$I(\lambda) = W(\lambda) \cdot I_0 e^{-\mu(\lambda)t - S} \tag{27}$$

In Equation 27, the term $u(A)$ represents a generic spectrally dependent absorption coefficient of all the intervening pigments in layer of thickness t between the surface of the retina and the sclera. In the spectral bandpass between 500 to 650 nm, $\lambda(\lambda)$ is dominated by oxyhemoglobin and deoxyhemoglobin.

An additional source of attenuation is scattering, however it is assumed that the scattering parameter S is wavelength independent. Given this simple model one is in search of a data reduction procedure which will "distill" the data, so as to reduce effects related to intensity variations and enhance spatial contrast between reduce effects related to intensity variations and enhance spatial contrast between regions differing spectrally as a result of differing concentrations of hemoglobin. Define the white calibrated reflectance spectrum $R(\lambda)$ by the following relation (Equation 28):

$$R(\lambda) = \frac{I(\lambda)}{W_m(\lambda)} \tag{28}$$

where $W_m(\lambda)$ is the white target spectrum, i.e., the measured spectrum from a white target placed in the position of the patient's eye. The white normalized differential $I_{nd}(\lambda)$, may then be defined as follows (Equation 29):

$$I_{nd}(\lambda) = \left[\frac{dR(\lambda)}{d\lambda}\right] \cdot R^{-1}(\lambda) \tag{29}$$

It is straight forward to show that for the model described by Equation 27 above, assuming $W(\lambda) = W_m(\lambda)$, the white normalized differential $I_{nd}(\lambda)$ yields (Equation 30):

$$I_{nd}(\lambda) = \frac{I_0 \mu'(\lambda) t \cdot e^{-\mu(\lambda)t + S}}{I_0 \cdot e^{-\mu(\lambda)t + S}} = \mu'(\lambda) t \tag{30}$$

The significance of Equation 30 above is that the white normalized differential is proportional to the thickness (or concentration) of the absorbing medium multiplied by the derivative of the absorption spectrum of the absorbing medium $\mu'(\lambda)$. Since both oxy- and deoxyhemoglobin have strongly modulated absorption spectra in the spectral regime of interest compared with virtually all other pigment species to be found in the ocular fundus, these two species act as the major sources of contrast in the image.

In order to create an image, the absolute value of $I_{nd}(\lambda)$ is summed over the wavelength $\lambda$ from each pixel, i.e., $I_{xy}$, the intensity at pixel x,y in the angiogram image is calculated as follows (Equation 31):

$$I_{xy} = \sum_{\lambda=\lambda_1}^{\lambda_2} |I_{nd}(\lambda)| \tag{31}$$

The spectral bounds $\lambda_2$ and $\lambda_1$ over which the sum is carried out may be varied in order to emphasize oxy- over deoxyhemoglobin or to select a spectral range in which other pigments in the fundus dominate. Further processing tools may also be used in order to eliminate periodic artifacts in the image related to the acquisition process.

Figure 26:
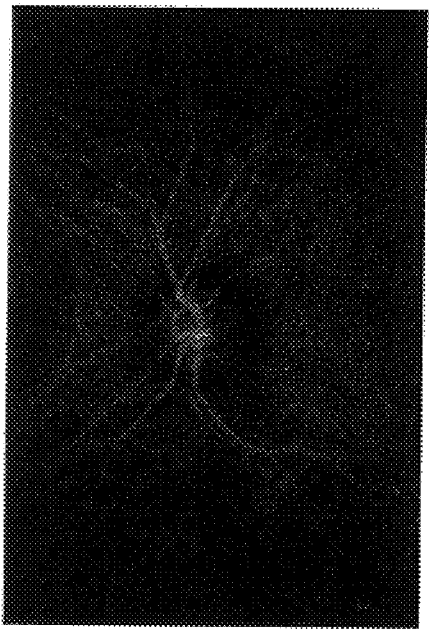
FIG. 26 shows a retinal angiographic image of an optical disc and surrounding retinal tissue of a healthy individual in which blood vessels are contrasted due to injection of indocyanine green dye to the examined individual.
Figure 27:
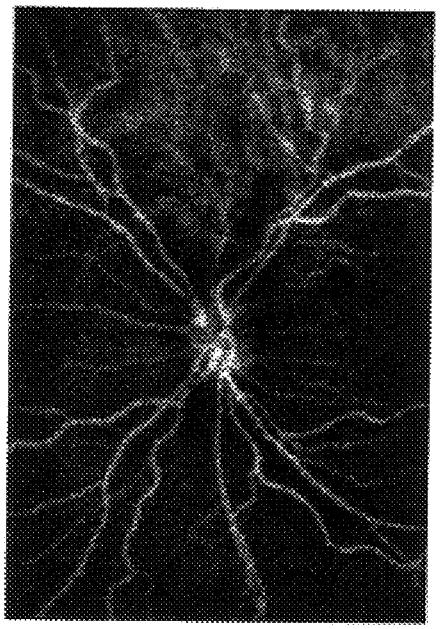
FIG. 27 shows a retinal angiographic image of an optical disc and surrounding retinal tissue of another healthy individual in which blood vessels are contrasted non-invasively using the absorption of intrinsic hemoglobin according to the present invention.

FIG. 26 shows a retinal angiographic image of an optical disc and surrounding retinal tissue of a healthy individual in which blood vessels are contrasted due to injection of indocyanine green dye to the examined individual, whereas FIG. 27 shows a retinal angiographic image of an optical disc and surrounding retinal tissue of another healthy individual in which blood vessels are contrasted non-invasively using the absorption of intrinsic hemoglobin using the algorithm described herein. It is clearly evident that the latter image includes more information relating to the distribution of blood vessels within the examined retina and that the contrast achieved using the algorithm herein described is higher.

Figure 28:
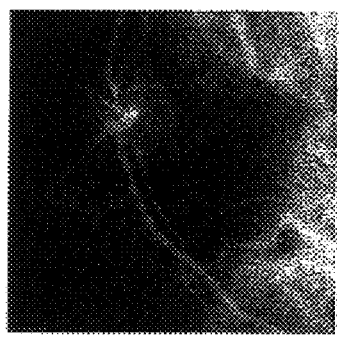
FIG. 28 shows a retinal angiographic image of an optical disc and surrounding retinal tissue of a patient suffering from age related macular degeneration in which blood vessels are contrasted due to injection of indocyanine green dye to the examined individual.
Figure 29:
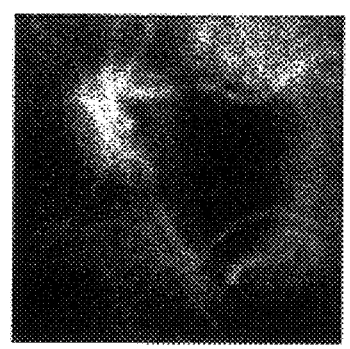
FIG. 29 shows a retinal angiographic image of an optical disc and surrounding retinal tissue of the patient of FIG. 28 in which blood vessels are contrasted non-invasively using the absorption of intrinsic hemoglobin according to the present invention.

Similarly, FIG. 28 shows a retinal angiographic image of an optical disc and surrounding retinal tissue of a patient suffering from age related macular degeneration in which blood vessels are contrasted due to injection of indocyanine green dye to the examined individual, whereas, FIG. 29 shows a retinal angiographic image of the same patient in which blood vessels are contrasted non-invasively using the absorption of intrinsic hemoglobin according to the present invention. It is clearly evident that the latter image includes all the information relating to the distribution of blood vessels within the examined retina, yet achieved non-invasively. The above demonstrates the efficiency of the spectrally resolved images using the algorithm herein described which are comparable and superior to conventional ICG images, yet is performed non-invasively. The spectral data analysis algorithm according to this aspect of the present invention is improved, in that it allows additional choroidal vessels to appear on the final image that were not brought forth before, using the procedures described hereinabove with respect to other embodiments of the invention. The spectral data analysis algorithm according to this aspect of the present invention is improved, in that it presents a sharper image and therefore it is a more meaningful tool for the eye of the ophthalmologist.

The spectral data analysis algorithm according to this aspect of the present invention is improved, in that it is faster and simpler, because it alone allows the simultaneous display of the retinal and choroidal vessels superimposed on the same image, just as in the composite images described above in which an algorithm brings forth separately the retinal and choroidal vessels, and then an additional computational step must be performed in order to display the superimposed images.

EXAMPLE 7

OXYGEN SATURATION MAPPING OF A TISSUE

One of the objects of the present invention is to provide an efficient optical imaging method to map the oxygen saturation state of a blood column in a tissue and in a blood vessel, in vivo. This method is suitable, in particular, for mapping the oxygen saturation in tissue and blood vessels of the ocular fundus, both in arteries and veins. This method, like the methods disclosed in the former examples, is based on spectral imaging combined with suitable data analysis algorithms.

The difficulty in implementing a method of mapping the oxygen saturation state of a blood column in, for example, a blood vessel, lies in the fact that for most applications, e.g., in the ocular fundus of a living human being, the blood vessels are embedded in a multilayer tissue structure and do not exist as stand alone objects, to be analyzed.

A spectral image cube or any other spectral data derived from the ocular fundus measured by reflected white light in vivo carries information on all the layers of which the fundus is composed. Thus, such spectral data carries information pertaining, for example, to the nerve fiber layer, the retinal pigment epithelium and to the choroid. In spectral images of the ocular fundus a clear vascular network that consists of the retinal vessels is observed on top of another network that consists of the choroidal vessels. Thus, there is a need for a tool or a method of extracting the spectral imaging information related only to the vessels under study.

It is evident that a method of mapping the oxygen saturation state of a blood column will find uses not only for eye inspection, but in numerous other applications in which there is a need to measure the spatial and spectral optical density map of an object which is located on top, behind or sandwiched between a number of other objects of different optical density, and the measurement is performed (similarly to the ocular fundus) from a direction nearly perpendicular to the planes of the layer structure. The reason is that in all such cases the incident light rays used for illumination go through all the layers of the structure, and are partly reflected, partly scattered, before they reach the spectral imaging sensor.

The ability to extract the absorption spectrum or optical density of a given object (or layer) from the spectrum of the multilayer structure, inside which it is embedded, is important when attempting to analyze specific material or composition properties of this object. The case of the blood hemoglobin saturation within the ocular fundus provides a particularly interesting and useful example, because it is related to the health and viability of the surrounding tissue. Within the ocular fundus the blood flows in different rates and directions within two different tissue layers, the retina and the choroid, that are spatially organized on top of each other and are related to the metabolism of two different metabolic states of the human eye. The oxygen saturation state of different arteries and veins of the retinal tissue is a clear indicator of its viability, as well as a possible indicator of certain pathologies. As further explained and exemplified hereunder, the present invention enables mapping of the oxygen saturation in retinal vessels in any chosen region of a digital fundus image, with a spatial resolution which is limited by the signal to noise ratio achieved in each analyzed region.

Oxygen saturation measurements of the retinal vessels have been carried out in the past, but mostly in small regions near or across a vessel separately. One exception is a 4-wavelength imaging method by a Company named Optical Insights (see J M Beach, J S Tiedeman, M Hopkins, Y Sabharwal, (1999) "Multi-spectral fundus imaging for early detection of diabetic retinopathy", SPIE Proceedings, Vol. 3603; however, the fundamental limitation of the Optical Insights instrument is that for each spectral band one must sacrifice the number of pixels. In practice, for a 256×256 image one cannot go beyond 4 bands. An analysis shows that the complexity of deconvolving the spectrum of retinal tissue is such that 4 bands will simply not be sufficient. Almost all the algorithms presented herein and exploited by the present invention rely on continous spectral data (of at least 20–100 data point resolution) to compensate for various biological diversity from point to point or patient to patient. A theoretical analysis of hemoglobin spectra shows that there is no benefit in improving spectral resolution to better than 9 nm for hemoglobin (Hb) oxygen saturation (OS) measurements. Another system is one being developed by Zeiss, which can only provide the data on a short line and cannot be extended to an image See also (i) FC Delori, "Noninvasive technique for oximetry of blood in retinal vessels", Applied Optics 27:1113–1125, 1988; (ii) F C Delori and K P Pflibsen, "Spectral reflectance of the ocular fundus", Applied Optics 28:1061–1077, 1989; (iii) J Sebag, F C Delori, G T Feke, J J Weiter, "Effects of Optic Atrophy on Retinal Blood Flow and Oxygen Saturation in Humans", Arch. Ophthalmol. 107:222–226, 1989; (iv) H A Bruining, G J M Pierik, C Ince, and F Ashruf, "Optical spectroscopic imaging for non-invasive evaluation of tissue oxygenation", Chirurgie 118:317–323, 1992; (v) M Hammer, D Schweitzer, L Leistritz, M Scibor, K-H Donnerhacke, and J Strobel, "Imaging Spectroscopy in Human Ocular Fundus In Vivo", J. Biomed. Optics 2:418–425, 1997; (vi) MH Smith, K R Denninghoff, L W Hillman, and R A Chipman, "Oxygen saturation measurements of blood in retinal vessels during blood loss", J Biomedical Optics 3:296–303, 1998; (vii) J S Tiedeman, S E Kirk, S Srinivas, J M Beach, "Retinal Oxygen Consumption during Hyperglycemia in Patients with Diabetes without Retinopathy", Ophthalmology, 105 (1):31–36, 1998; and (viii) D Schweitzer, L Leistritz, M Hammmer, M Scibor, U Bartsch and J Strobel, "Calibration-free measurements of the oxygen saturation in retinal vessels of men" SPIE 2393:210–218, 1995. In general, the prior art fails to measure or acquire spectral images, and is therefore limited to either selected small regions on the analyzed tissue or a small number of wavelengths.

The following summarizes the main differences between the prior art and what is covered by this embodiment of the present invention:

(i) Prior art instruments do not produce a spectral cube, so they cannot be applied to an image. Therefore, the points being measured should be chosen apriori. Thus, the prior art do not provide a tool for examining the retina as a whole.

(ii) In sharp contrast to the prior art and as further detailed hereunder, the present invention employs a special "local background compensation method" which takes into account the variability of the background tissue and the signal's quality. By applying smart averaging on regions with similar background tissue while taking into account the spectral variability of the tissue, the noise level is reduced and a robust measurement of the oxygen saturation in the blood vessel is obtained. It turns out that this reduces noise and increases the robustness of the results with respect to biological variability. In the prior art a background compensation method has been used to measure two spots next to each other, one on the vessel and one close to it. As an example of the superiority of the method of the present invention it should be noted that in the prior art method the background point is chosen by the eye of the user which may mistakenly and wrongfully select a background point which contains a choroidal vessel, while the analyzed point does not include one, thereby distorting the result.

(iii) In the prior art, results are shown only based on a few wavelengths (typically 2, 3 or 4). Ocassionally, the prior art is somewhat superior in spectral resolution, but, as further explained below, cannot be used to carry out a differential fit and is therefore much more disturbed by scattering. Moreover, in general, by basing the calculations on a larger number of wavelengths, as done in the presented invention, the number of equations upon which the oxygen saturation data are fitted to the model is increased, thus increasing the reliability of the results obtained.

A simple model that describes the reflection $I_N(\lambda)$ of white light from the retina is obtained by assuming that the illumination signal is transmitted through N partially absorbing and partially scattering layers and reflected back from a white substrate (the sclera) through the same layers. The attenuation of the signal by each layer is described by the Beer-Lambert law, and the measured signal is thus given by:

$$I_N(\lambda) = W(\lambda) \cdot \exp\left[-\left(\sum_i^N a_i(\lambda) \cdot 2l_i\right)\right], \quad (32)$$

where $W(\lambda)$ is the intensity of the incident light; $i=1, \ldots, N$ is the index of the layers; $a_i(\lambda)$, which is a function of the wavelength $\lambda$, is the corresponding attenuation coefficient; $l_i$ is the thickness of the layer i, where it is assumed that the light is reflected back and forth through the same layers to give the factor 2.

Removing the Nth layer (the vessel) gives rise to:

$$I_{N-1}(\lambda) = W(\lambda) \cdot \exp\left[-\left(\sum_i^{N-1} a_i(\lambda) \cdot 2l_i\right)\right] \quad (33)$$

Dividing Equation 32 by Equation 33 yields:

$$I_N/I_{N-1} = \exp[-\alpha_N \cdot 2l_N] \quad (34)$$

$$I_N/I_{N-1} = \exp[-\alpha_N(\lambda) \cdot I_N] \quad (35)$$

Within the framework of the Beer—Lambert law, one assumes two contributions to $\alpha_N(\lambda)$, the first due to absorption, $\lambda_N(\lambda)$, and the second due to scattering, $s_N(\lambda)$. When the Nth layer is a blood vessel, its attenuation characteristics are dominated by the absorption coeficient of hemoglobin, which varies strongly with $\lambda$ in the region between 500 nm and 650 nm, while the scattering coefficient, $S_N(\lambda)$, is weakly dependent on the wavelength $\lambda$.

Thus, in the wavelength region of 500 nm–650 nm one assumes that the following holds approximately:

$$d a_N(\lambda)/d\lambda = d\mu_N(\lambda)/d\lambda \quad (36)$$

For $\mu(\lambda)$ in the case of hemoglobin (see, for example, FC Delori, "Noninvasive technique for oximetry of blood in retinal vessels", Applied Optics 27:1113–1125, 1988), one applies the effective medium approximation:

$$\lambda(\lambda) = {}^\epsilon HbO_2(\lambda) \cdot [HbO_2] + \epsilon_{Hb}(\lambda) \cdot [Hb] \quad (37)$$

where $[HbO_2]$ and $[Hb]$ are the concentration of the oxygenated and deoxygenated hemoglobin, respectively, and ${}^\epsilon HbO_2(\lambda)$ and ${}^\epsilon Hb(\lambda)$ are the oxygenated and deoxygenated hemoglobin absorption coefficients, respectively. The oxygen saturation, OS, is measured in percent and is defined as:

$$OS = 100 \times [HbO_2]/([HbO_2] + [Hb]) \quad (38).$$

Combining Equations 34, 36, and 37 one obtains:

$$-\frac{d}{d\lambda}\ln(I_N/I_{N-1}) \cong 2l_N \times \left(\frac{d\varepsilon_{HbO_2}}{d\lambda}[HbO_2] + \frac{d\varepsilon_{Hb}}{d\lambda}[Hb]\right) \quad (39)$$

The fact that typically the hemoglobin concentration, c, in human blood is constant is exploited, i.e.:

$$c = [HbO_2] + [Hb] = \text{const.} = 8.98 \, \mu\text{mole/ml} \quad (40)$$

and therefore:

$$-\frac{d}{d\lambda}\ln(I_N/I_{N-1}) \cong \quad (41)$$

$$\frac{2l_N c}{100}\left[OS\left(\frac{d\varepsilon_{HbO_2}(\lambda)}{d\lambda} - \frac{d\varepsilon_{Hb}(\lambda)}{d\lambda}\right) + 100\frac{d\varepsilon_{Hb}(\lambda)}{d\lambda}\right]$$

Equation 41 is the basic expression of the oxygen saturation model according to the present invention for an object in the ocular fundus or in any other similar layered structure. The left hand side of Equation 41 contains only measured quantities ($I_N$, $I_{N-1}$), while the right hand side contains the known quantities ${}^\epsilon HbO_2(\lambda)$ and ${}^\epsilon Hb(\lambda)$, and the unknown quantities $l_N$ and OS.

It will be appreciated that melanin and other pigments present in living tissue, and important in the characterization of the tissue in question, may also be measured in a similar way.

It should be noted that when the oxygenation state of a general tissue is measured, whether in the ocular fundus or in other regions of the body, one can use Equation 41 with the following changes:

$I_N$ is now the signal from the tissue (between vessels), and as reference signal, $I_{N-1}$, one now employs the reflected light from a white target positioned in place of the tissue to be measured. An ideal white target is defined as a target which reflects 100% of the light incident on it at all wavelengths. The ideal white target is a physical abstraction, but practical plates which approach the ideal white target are available commercially from several companies, such as Labsphere Inc. and others.

Equation 41 is the basis for calculating the oxygen saturation in a specific object such as a retinal or choroidal blood vessel, using spectral data derived, for example, from a spectral cube of data.

For purpose of illustration only, the following descriptions focus mainly on retinal vessels, unless otherwise specified.

Thus, $I_N$ is defined as the reflected spectral intensity from a retinal vessel, and $I_{N-1}$ is a reference spectral intensity representing the reflection from all the other layers. In order to measure $I_N(A)$ and $I_{N-1}(\lambda)$ a special algorithm and user interface have been developed for the SPECTRACUBE™ instrument to enable the definition of a region of interest, e.g., a blood vessel (see, for example, region 1 in FIGS. 30a–b) and its surroundings on the ocular fundus (region 3 in FIGS. 30a–b).

Two assumptions are now made: (i) the oxygen saturation level in the vessel is not a strong function of the location within the region of interest, which allows one to improve the signal to noise ratio of the measured $I_N$ by averaging it over many pixels along the vessel; and (ii) the close surroundings of the region of interest on the vessel represents the layers underneath the region of interest on the vessel when its spectrum $I_{N-1}(\lambda)$ is averaged over several pixels in the same region as further explained below.

The values of $I_N(\lambda)$ and $I_{N-1}(\lambda)$ so obtained are substituted in the left-hand side of Equation 41, while $\epsilon_{HbO_2}(\lambda)$ and $\epsilon_{Hb}(\lambda)$ from the literature are substituted in the right hand side of Equation 41. In order to compensate for the spectral resolution of the measuring system, which is lower than the spectral resolution upon which $\epsilon_{HbO_2}(2)$ and $\epsilon_{Hb}(\lambda)$ were obtained in the literature, the functions $\epsilon_{HbO_2}(2)$ and $\epsilon_{Hb}(\lambda)$ are preferably convolved with a broadening window. $I_N$ and OS are then calculated by best fitting the two sides of Equation 41 using a minimal squares technique under the restriction that c, which is the typical hemoglobin concentration in human blood (see above), is a constant. Upon fitting, one allows a spectral shift of a few nanometers in order to account for residual scattering effects. The difference between the measured and the calculated values in Equation 41, which is indicative of the quality of the fit, is then used in order evaluate the applicability of the model in every specific case. The value of c that is used is preferably 8.98 $\mu$mole/ml. This is a standard value for the total hemoglobin concentration in humans. It does vary from person to person and according to Equation 41 it also influences the estimated value for the thickness $I_N$. See, van Assendelft OW, *Spectrophotometry haemoglobin derivatives,* Charles C Thomas, Springfield Ill., 1970.

Figure 32:
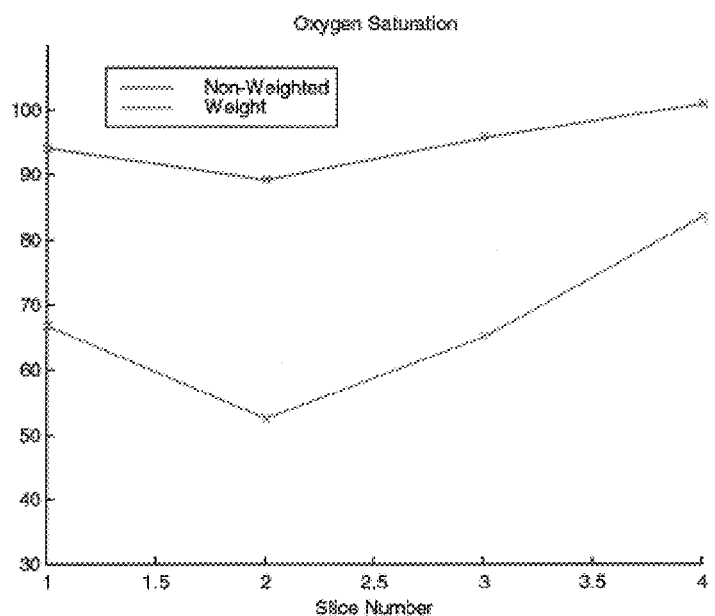
FIG. 32 show estimates of oxygen saturation in the different four slices (red curve) and the corresponding reliability weight in arbitrary units (blue curve).
Figure 33A:
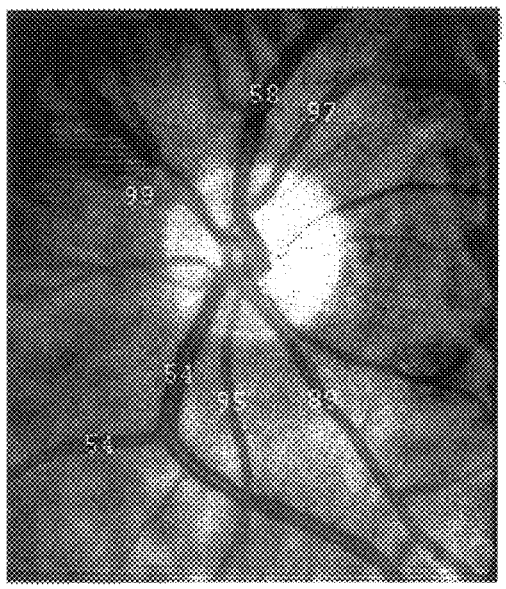
FIGS. 33a–b display oxygen saturation on retinal vessels of healthy eyes.
Figure 33B:
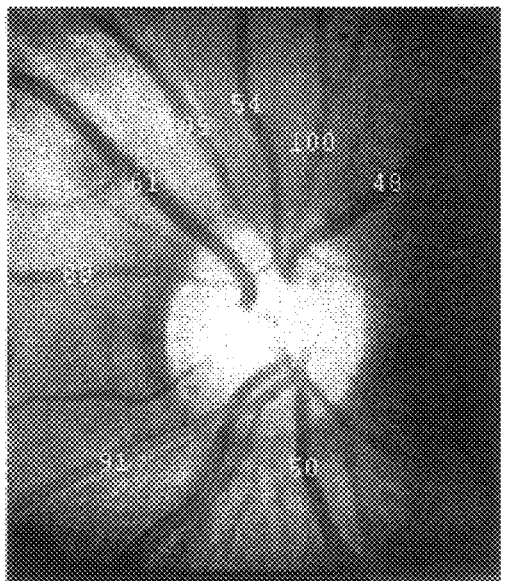
Figure 34A:
FIGS. 34a–c display oxygen saturation on retinal vessels of eyes with pathologies.
Figure 34B:
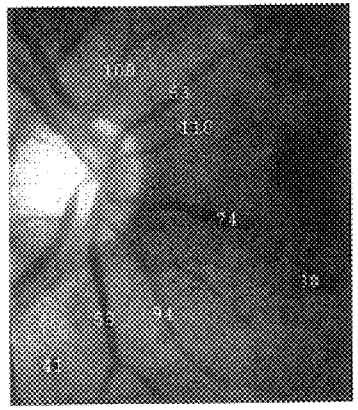
Figure 34C:
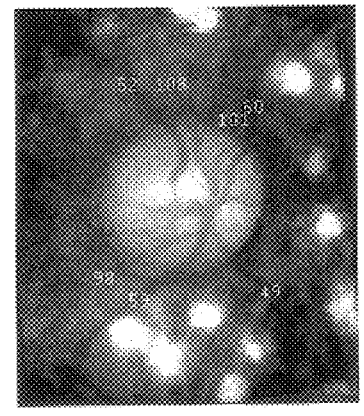

In order to reduce errors that may result from local variability of the tissue surrounding the region of interest on the vessel, a method of local background averaging has been developed (FIG. 31). The region of interest on the vessel together with its surrounding background region are sliced along their curved equator (the curvature arising from the shape of the vessel); accordingly, the vessel is sliced across its length, as indicated by the black, pink, green and red colors of the central image of FIG. 31. The size of the slices is determined by the desired signal to noise ratio. The slices should be large enough to reduce noise, but not too large in order not to introduce distortions of the local background spectrum. Equation 41 is then applied to each slice separately, and the final result for the specific vessel is obtained by a weighted average of the results from all the slices (FIG. 32).

The weight of each slice is defined in this example by the product of the signal to noise ratio of the slice, the number of pixels used and the fit quality of the slice. Clearly, different definitions may be used.

The result of the weighted average of the oxygen saturation along various retinal vessels in the image is displayed as a % saturation value shown on each corresponding vessel (see FIGS. 4*a*-and 5*a*-*c*).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A spectral bio-imaging method for enhancing spectral signatures of an eye tissue, the method comprising the steps of:
    (a) providing an optical device for eye inspection being optically connected to a spectral imager;
    (b) illuminating the eye tissue with light via the iris, viewing the eye tissue through said optical device and spectral imager and obtaining a spectrum of light for each pixel of the eye tissue; and
    (c) attributing each of said pixels a color or intensity according to its spectral signature, thereby providing an image enhancing the spectral signatures of the eye tissue.

2. The method of claim 1, wherein said spectral imager is selected from the group consisting of a filters based spectral imager, a monochromator based spectral imager and an interferometer based spectral imager.

3. The method of claim 2, wherein step (b) includes
    (i) collecting incident light simultaneously from all pixels of said eye using collimating optics;
    (ii) passing said incident collimated light through an interferometer system having a number of elements, so that said light is first split into two coherent beams which travel in different directions inside said interferometer and then said two coherent beams recombine to interfere with each other to form an exiting light beam;
    (iii) passing said exiting light beam through a focusing optical system which focuses said exiting light beam on a detector having a two-dimensional array of detector elements;
    (iv) rotating or translating one or more of said elements of said interferometer system, so that an optical path difference between said two coherent beams generated by said interferometer system is scanned simultaneously for all said pixels; and
    (v) recording signals of each of said detector elements as function of time using a recording device to form a spectral cube of data.

4. The method of claim 3, wherein said two-dimensional array is selected from the group consisting of a video rate CCD, a cooled high dynamic range CCD, an intensified CCD and a time gated intensified CCD.

5. The method of claim 3, further comprising the step of correcting spatial and spectral information for movements of the eye tissue via a spatial registration and spectral correction procedures.

6. The method of claim 1, wherein said optical device is selected from the group consisting of a fundus camera and a funduscope.

7. The method of claim 1, wherein said spectrum of light represents light selected from the group consisting of, light reflected from the eye tissue, light scattered from the eye tissue and light emitted from the eye tissue.

8. The method of claim 7, wherein said light emitted from said eye tissue is selected from the group consisting of administered probe fluorescence, administered probe induced fluorescence and auto-fluorescence.

9. The method of claim 1, wherein said light used for illuminating the eye tissue is selected from the group consisting of coherent light, white light, filtered light, ultraviolet light, infrared light and a light having a small wavelength range.

10. The method of claim 1, wherein said eye tissue is selected from the group consisting of eye retina, a retinal blood vessel an optic disk, an optic cup, eye macula, fovea, cornea, iris, lens, nerve fiber layer, choroid, choroidal layer, choroidal blood vessel, pigment epithelium and Bruch's membrane.

11. The method of claim 1, wherein the eye tissue includes a blood vessel the method is for detecting and mapping the oxygenation level of hemoglobin along the blood vessel.

12. The method of claim 1, wherein step (c) is effected using a mathematical algorithm which computes a Red-Green-Blue color image using predefined wavelength ranges.

13. The method of claim 1, wherein said spectral signature and, as a result, said color is affected by a substance selected from the group consisting of hemoglobin, cytochromes, oxidases, reductases, flavins, nicotinamide adenine dinucleotide, nicotinamide adenine dinucleotide phosphate, collagen, elastin, xanthophyll and melanin.

14. The method of claim 1, wherein enhancing the spectral signatures of the eye tissue includes an enhancement selected from the group consisting of enhancing arteries, enhancing veins, enhancing hemoglobin concentration, enhancing hemoglobin oxygen saturation level, enhancing melanoma lesions and enhancing hemangioma lesions.

15. The method of claim 1, wherein said spectral imager is selected from the group consisting of a filters based spectral imager, a monochromator based spectral imager and an interferometer based spectral imager.

16. The method of claim 15, wherein step (b) includes:
   (i) collecting incident light simultaneously from all pixels of said object using collimating optics;
   (ii) passing said incident collimated light through an interferometer system having a number of elements, so that said light is first split into two coherent beams which travel in different directions inside said interferometer and then said two coherent beams recombine to interfere with each other to form an exiting light beam;
   (iii) passing said exiting light beam through a focusing optical system which focuses said exiting light beam on a detector having a two-dimensional array of detector elements;
   (iv) rotating or translating one or more of said elements of said interferometer system, so that an optical path difference between said two coherent beams generated by said interferometer system is scanned simultaneously for all said pixels; and
   (v) recording signals of each of said detector elements as function of time using a recording device to form a spectral cube of data.

17. The method of claim 16, wherein said two-dimensional array is selected from the group consisting of a video rate CCD, a cooled high dynamic range CCD, an intensified CCD and a time gated intensified CCD.

18. The method of claim 16, further comprising the step of correcting spatial and spectral information for movements of the eye tissue via a spatial registration and spectral correction procedures.

19. A method of evaluating a medical condition of a patient comprising the step of enhancing spectral signatures of an eye tissue of the patient by:
   (a) providing an optical device for eye inspection being optically connected to a spectral imager;
   (b) illuminating the eye tissue of the patient with light via the iris, viewing the eye tissue through said optical device and spectral imager and obtaining a light spectrum for each pixel of the eye tissue;
   (c) attributing each of said pixels a color or intensity according to its spectral signature, thereby providing an image enhancing the spectral signatures of the eye tissue; and
   (d) using said image to evaluate the medical condition of the patient.

20. The method of claim 19, wherein said medical condition is selected from the group consisting of diabetic retinopathy, ischemia of the eye, glaucoma, macular degeneration, CMV eye infection, melanoma lesions, hemangioma lesions, retinitis, choroidal ischemia, acute sectorial choroidal ischemia, ischemic optic neuropathy, and corneal and iris problems.

21. An apparatus for providing a display of an image presenting an eye tissue, wherein each pixel in said image is assigned a color or intensity according to a spectral signature of a tissue element from which it is derived, thereby enhancing the spectral signature of the eye tissue comprising:
   (a) an optical device for eye inspection being optically connected to a spectral imager;
   (b) an illumination source for illuminating the eye tissue with light via the iris; and
   (c) an image display device for displaying the image; wherein the image is realized by viewing the eye tissue through said optical device and spectral imager and obtaining a spectrum of light for each pixel of the eye tissue; and further by attributing each of said pixels a color or intensity according to its spectral signature, thereby providing the image enhancing the spectral signatures of the eye tissue.

22. A spectral bio-imaging method for obtaining a spectrum of a region of an eye tissue, the method comprising the steps of:
   (a) providing an optical device for eye inspection being optically connected to a spectral imager;
   (b) illuminating the eye tissue with light via the iris, viewing the eye tissue through said optical device and spectral imager and obtaining a spectrum of light for each pixel of the eye tissue; and
   (c) displaying a spectrum associated with said region.

23. A spectral bio-imaging method for enhancing spectral signatures of an eye tissue, the method comprising the steps of:
   (a) providing an optical device for eye inspection being optically connected to a high throughput spectral imager;
   (b) illuminating the eye tissue with light via the iris, viewing the eye tissue through said optical device and spectral imager and obtaining a spectrum of light for each pixel of the eye tissue; and
   (c) attributing each of said pixels a color or intensity according to its spectral signature in a predefined spectral range, thereby providing an image enhancing the spectral signatures of the eye tissue.

24. The method of claim 23, wherein said spectral imager is selected from the group consisting of a wideband filters based spectral imager, decorrelation matched filters based spectral imager, a successively monochromatic illumination based spectral imager and an interferometer based spectral imager.

25. The method of claim 24, wherein step (b) includes:
   (i) collecting incident light simultaneously from all pixels of said eye using collimating optics;
   (ii) passing said incident collimated light through an interferometer system having a number of elements, so that said light is first split into two coherent beams which travel in different directions inside said interferometer and then said two coherent beams recombine to interfere with each other to form an exiting light beam;
   (iii) passing said exiting light beam through a focusing optical system which focuses said exiting light beam on a detector having a two-dimensional array of detector elements;
   (iv) rotating or translating one or more of said elements of said interferometer system, so that an optical path difference between said two coherent beams generated by said interferometer system is scanned simultaneously for all said pixels; and
   (v) recording signals of each of said detector elements as function of time using a recording device to form a spectral cube of data.

26. The method of claim 25, wherein said two-dimensional array is selected from the group consisting of a video rate CCD, a cooled high dynamic range CCD, an intensified CCD and a time gated intensified CCD.

27. The method of claim 25, further comprising the step of correcting spatial and spectral information for movements of the eye tissue via a spatial registration and spectral correction procedures.

28. The method of claim 23, wherein said optical device is selected from the group consisting of a fundus camera and a funduscope.

29. The method of claim 23, wherein said spectrum of light represents light selected from the group consisting of, light reflected from the eye tissue, light scattered from the eye tissue and light emitted from the eye tissue.

30. The method of claim 29, wherein said light emitted from said eye tissue is selected from the group consisting of administered probe fluorescence, administered probe induced fluorescence and auto-fluorescence.

31. The method of claim 23, wherein said light used for illuminating the eye tissue is selected from the group consisting of coherent light, white light, filtered light, ultraviolet light and a light having a small wavelength range.

32. The method of claim 23, wherein said eye tissue is selected from the group consisting of eye retina, a retinal blood vessel an optic disk, an optic cup, eye macula, fovea, cornea, iris, lens, nerve fiber layer, choroid, choroidal layer, choroidal blood vessel, pigment epithelium and Bruch's membrane.

33. The method of claim 23, wherein the eye tissue includes a blood vessel the method is for detecting and mapping the oxygenation level of hemoglobin along the blood vessel.

34. The method of claim 23, wherein step (c) is effected using a mathematical algorithm which computes a Red-Green-Blue color image using predefined wavelength ranges.

35. The method of claim 23, wherein step (c) is effected using a mathematical algorithm which computes a gray scale image using predefined wavelength ranges.

36. The method of claim 23, wherein said spectral signature and, as a result, said color is affected by a substance selected from the group consisting of hemoglobin, cytochromes, oxidases, reductases, flavins, nicotinamide adenine dinucleotide, nicotinamide adenine dinucleotide phosphate, collagen, elastin, xanthophyll and melanin.

37. The method of claim 25, wherein enhancing the spectral signatures of the eye tissue includes an enhancement selected from the group consisting of enhancing arteries, enhancing veins, enhancing hemoglobin concentration, enhancing hemoglobin oxygen saturation level, enhancing melanoma lesions and enhancing hemangioma lesions.

38. A method of evaluating a medical condition of a patient comprising the step of enhancing spectral signatures of an eye tissue of the patient by:
  (a) providing an optical device for eye inspection being optically connected to a high throughput spectral imager;
  (b) illuminating the eye tissue of the patient with light via the iris, viewing the eye tissue through said optical device and spectral imager and obtaining a light spectrum for each pixel of the eye tissue;
  (c) attributing each of said pixels a color or intensity according to its spectral signature in a predefined spectral range, thereby providing an image enhancing the spectral signatures of the eye tissue; and
  (d) using said image to evaluate the medical condition of the patient.

39. The method of claim 38, wherein said medical condition is selected from the group consisting of diabetic retinopathy, ischemia of the eye, glaucoma, macular degeneration, CMV eye infection, retinitis, choroidal ischemia, acute sectorial choroidal ischemia, ischemic optic neuropathy, and corneal and iris problems.

40. An apparatus for providing a display of an image presenting an eye tissue, wherein each pixel in said image is assigned a color or intensity according to a spectral signature of a tissue element from which it is derived, thereby enhancing the spectral signature of the eye tissue comprising:
  (a) an optical device for eye inspection being optically connected to a spectral imager;
  (b) an illumination source for illuminating the eye tissue with light via the iris; and
  (c) an image display device for displaying the image; wherein the image is realized by viewing the eye tissue through said optical device and spectral imager and obtaining a spectrum of light for each pixel of the eye tissue and further by attributing each of said pixels a color or intensity according to its spectral signature in a predefined spectral range, thereby providing the image enhancing the spectral signatures of the eye tissue.

41. A spectral bio-imaging method for enhancing spectral signatures of at least two eye tissues, each of a different spectral signature, the method comprising the steps of:
  (a) providing an optical device for eye inspection being optically connected to a spectral imager;
  (b) illuminating the eye tissues with light via the iris, viewing the eye tissues through said optical device and spectral imager and obtaining a spectrum of light for each pixel of the eye tissues;
  (c) selecting spectral ranges highlighting the different spectral signatures of each of the at least two eye tissues; and
  (d) generating an image enhancing the different spectral signatures of the at least two eye tissues.

42. A spectral bio-imaging method for enhancing blood vessels of an eye tissue, the method comprising the steps of:
  (a) providing an optical device for eye inspection being optically connected to a spectral imager;
  (b) illuminating the eye tissues with light via the iris, viewing the eye tissue through said optical device and spectral imager and obtaining a spectrum of light for each pixel of the eye tissue;
  (c) employing an algorithm highlighting a spectral signature of blood vessels; and
  (d) generating an image enhancing the blood vessels.

43. An apparatus for providing a display of an image presenting an eye tissue in which blood vessels are enhanced by a color or intensity according to a spectral signature specific thereto, the apparatus comprising:
  (a) an optical device for eye inspection being optically connected to a spectral imager;
  (b) an illumination source for illuminating the eye tissue with light via the iris; and
  (c) an image display device for displaying the image; wherein the image is realized by viewing the eye tissue through said optical device and spectral imager and obtaining a spectrum of light for each pixel of the eye tissue; and further by attributing each of said pixels a color or intensity according to its spectral signature, thereby enhancing the spectral signature of blood vessels in the eye tissue.

44. A spectral bio-imaging method for extracting a spectral signature of a first portion of a layer of an object including at least two layers, each of said at least two layers has different spectral characteristics, the method comprising the steps of:

(a) providing an optical device being optically connected to a spectral imager;

(b) illuminating the object with light, viewing the object through said optical device and spectral imager and obtaining a continuous spectrum of light for each pixel of the object;

(c) using said continuous spectrum of light of each pixel of the object for generating a spectral image of the object in which the first portion is identifiable;

(c) identifying in said spectral image the first portion of the layer and a second portion being adjacent said first portion; and (d) accounting for spectral characteristics of said second layer, extracting the spectral signature of the first portion.

45. The method of claim 44, wherein said object is an ocular fundus, said at least two layers include a retinal layer and a choroidal layer and said first portion is selected from the group consisting of a retinal blood vessel and a choroidal blood vessel.

46. The method of claim 45, wherein said spectral signature is indicative of an oxygenation state of said first portion.

47. The method of claim 46, further comprising the step of marking a mark indicative of said oxygenation state of said first portion on said spectral image in context of said first portion.

48. The method of claim 47, wherein said mark is a numerical value.

49. The method of claim 44, wherein said spectral signature is indicative of an oxygenation state of said first portion.

50. The method of claim 44, wherein said step of extracting the spectral signature of the first portion includes averaging over a plurality of said pixels.

51. The method of claim 44, wherein said optical device is selected from the group consisting of a fundus camera and a funduscope.

52. The method of claim 44, wherein said continuous spectrum of light represents light selected from the group consisting of, light reflected from the object and light scattered from the object.

53. The method of claim 44, wherein said light used for illuminating the object is selected from the group consisting of coherent light, white light, filtered light, ultraviolet light and a light having a small wavelength range.

54. A method of evaluating a medical condition of a patient comprising the step of extracting a spectral signature of a retinal or choroidal blood vessel of a retina or choroid of an eye by:

(a) providing an optical device being optically connected to a spectral imager;

(b) illuminating the eye with light, viewing the eye through said optical device and spectral imager and obtaining a continuous spectrum of light for each pixel of the eye;

(c) using said continuous spectrum of light of each pixel of the eye for generating a spectral image of the eye in which the retinal or choroidal blood vessel is identifiable;

(c) identifying in said spectral image the retinal or choroidal blood vessel and a tissue being adjacent to the retinal or choroidal blood vessel;

(d) accounting for spectral characteristics of said tissue, extracting the spectral signature of the retinal or choroidal blood vessel; and (e) using said spectral signature to evaluate the medical condition of the patient.

55. The method of claim 54, wherein said medical condition is selected from the group consisting of diabetic retinopathy, ischemia of the eye, glaucoma, macular degeneration, CMV eye infection, melanoma lesions, hemangioma lesions, retinitis, choroidal ischemia, acute sectorial choroidal ischemia, ischemic optic neuropathy, and corneal and iris problems.

56. An apparatus for providing a display of an image presenting an eye tissue and a marking of an oxygenation state of at least one blood vessel therein, the apparatus comprising:

(a) an optical device for eye inspection being optically connected to a spectral imager;

(b) an illumination source for illuminating the eye tissue with light via the iris; and (c) an image display device for displaying the image; wherein the image is realized by viewing the eye tissue through said optical device and spectral imager and obtaining a spectrum of light for each pixel of the eye tissue; by attributing each of said pixels a color or intensity according to its spectral signature, thereby providing the image enhancing the spectral signatures of the eye tissue; and further by marking in context of the at least one blood vessel the oxygenation state thereof.

* * * * *